(12) United States Patent
Manel et al.

(10) Patent No.: US 8,404,482 B2
(45) Date of Patent: Mar. 26, 2013

(54) METHODS FOR IN VITRO DIFFERENTIATION OF TH-17+ CELLS

(75) Inventors: Nicolas Manel, New York, NY (US); Dan R. Littman, New York, NY (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 13/473,980

(22) Filed: May 17, 2012

(65) Prior Publication Data

US 2012/0244543 A1 Sep. 27, 2012

Related U.S. Application Data

(62) Division of application No. 12/386,355, filed on Apr. 15, 2009, now Pat. No. 8,183,040.

(60) Provisional application No. 61/124,242, filed on Apr. 15, 2008.

(51) Int. Cl.
*C12N 5/08* (2006.01)
*C12N 5/02* (2006.01)
*C12N 5/00* (2006.01)

(52) U.S. Cl. ......... 435/372; 435/375; 435/377; 435/405

(58) Field of Classification Search .................. None
See application file for complete search history.

(56) References Cited

PUBLICATIONS

Acosta-Rodriguez et al., "Interleukins 1beta and 6 but not transforming growth factor-beta are essential for the differentiation of interleukin 17-producing human T helper cells", Nature Immunology, 2007, pp. 942-949, vol. 8, No. 9.
Acosta-Rodriguez et al., "Surface phenotype and antigenic specificity of human interleukin 17-producing T helper memory cells", Nature Immunology, 2007, pp. 639-646, vol. 8, No. 6.
Bettelli et al., "Reciprocal developmental pathways for the generation of pathogenic effector TH17 and regulatory T cells", Nature, 2006, pp. 235-238, vol. 441.
Chen et al., "Distinct regulation of interleukin-17 in human T helper lymphocytes", Arthritis & Rheumatism, 2007, pp. 2936-2946, vol. 56, No. 9.
De Rosa et al., "11-color, 13-parameter flow cytometry: Identification of human naive T cells by phenotype, function, and T-cell receptor diversity", Nature Medicine, 2001, pp. 245-248, vol. 7, No. 2.

Evans et al., "Optimal induction of T helper 17 cells in humans requires T cell receptor ligation in the context of Toll-like receptor-activated monocytes", Proc Natl Acad Sci, 2007, pp. 17034-17039, vol. 104, No. 43.
Ivanov et al., "The orphan nuclear receptor RORgammat directs the differentiation program of proinflammatory IL-17+T helper cells", Cell, 2006, pp. 1121-1133, vol. 126.
Korn et al., "IL-21 initiates an alternative pathway to induce proinflammatory TH17 cells", Nature, 2007, pp. 484-487, vol. 448.
Laurence et al., "TH-17 differentiation: of mice and men", Nature Immunology, 2007, pp. 903-905, vol. 8, No. 9.
Mangan et al., "Transforming growth factor-beta induces development of TH17 lineage", 2006, Nature, pp. 231-234, vol. 441.
McGeachy et al., "TGF-beta and IL-6 drive the production of IL-17 and IL-10 by T cells and restrain Th-17 cell-mediated pathology", Nature Immunology, 2007, pp. 1390-1397, vol. 8, No. 12.
Mucida et al., "Reciprocal TH17 and regulatory T cell differentialtion mediated by retinoic acid", Science, 2007, pp. 256-260, vol. 317.
Nurieva et al., "Essential autocrine regulation by IL-21 in the generation of inflammatory T cells", Nature, 2007, pp. 480-483, vol. 448.
Stockinger et al., "Th17 T cells: Linking innate and adaptive immunity", Seminars in Immunology, 2007, pp. 353-361, vol. 19.
Van Beelen et al., "Stimulation of the intracellular bacterial sensor NOD2 programs dendritic cells to promote interleukin-17 production in human memory T cells", Immunity, 2007, pp. 660-669, vol. 27.
Veldhoen et al., "TGFbeta in the context of an inflammatory cytokine milieu supports de novo differentiation of IL-17-producing T cells", Immunity, 2006, pp. 179-189, vol. 24.
Wilson et al., "Development, cytokine profile and function of human interleukin 17-producing helper T cells", Nature Immunology, 2007, pp. 950-957, vol. 8, No. 9.
Zheng et al., "Interleukin-22, a TH17 cytokine, mediates IL-23-induced dermal inflammation and acanthosis", Nature, 2007, pp. 648-651, vol. 445.
Zhou et al., "IL-6 prorams TH-17 cell differentiation by promoting sequential engagement of the IL-21 and IL-23 pathways", Nature Immunology, 2007, pp. 967-974, vol. 8, No. 9.

*Primary Examiner* — Michail Belyavskyi
(74) *Attorney, Agent, or Firm* — Klauber & Jackson LLC

(57) ABSTRACT

The present invention is directed to an in vitro method for promoting differentiation and proliferation of human T helper lymphocytes that express IL17 (Th-IL17+ cells). The instant method may be used to generate a population of human T helper lymphocytes that express IL17 (Th-IL17+ cells) in vitro. Methods for screening to identify agents capable of modulating Th-IL17+ cell differentiation are also encompassed by the present invention. Isolated, pure populations of homogeneous Th-IL17+ cells that do not express cellular markers characteristic of Th1, Th2, or Treg cells are also encompassed herein.

5 Claims, 11 Drawing Sheets

METHODS FOR IN VITRO DIFFERENTIATION OF TH-17+ CELLS

CROSS REFERENCE TO RELATED APPLICATIONS

The present application is a Divisional Application of U.S. application Ser. No. 12/386,355, filed Apr. 15, 2009 now U.S. Pat. No. 8,183,040, which in turn claims priority under 35 USC §119(e) from U.S. Provisional Application Ser. No. 61/124,242, filed Apr. 15, 2008, each of which applications is herein specifically incorporated by reference in its entirety.

The research leading to the present invention was funded in part by NIH grants 5 R37 AI033303 and R01 AI065303. The United States government may have certain rights in the invention.

FIELD OF THE INVENTION

The present invention pertains to the fields of cell culture, immunology, and T lymphocytes. More specifically, the invention relates to in vitro methods directed to promoting differentiation and proliferation of human Th-17+ cells and to in vitro screening methods directed to identifying agents capable of modulating human Th-17+ cells differentiation. Homogenous populations of Th-17+ cells generated using the methods of the invention are also described herein.

BACKGROUND OF THE INVENTION

Several publications and patent documents are referenced in this application in order to more fully describe the state of the art to which this invention pertains. The disclosure of each of these publications and documents is incorporated by reference herein.

Th17 cells, the T helper cells that produce IL-17 and other pro-inflammatory cytokines, have been shown to have key functions in a wide variety of autoimmune disease models in mice and are thought to be similarly involved in human disease (reviewed[1-3]). In healthy humans, IL-17-secreting cells are present in the CD45RO+CCR6+ populations of T cells from peripheral blood[4,5] and gut[5]. Th17 cells or their products have been associated with the pathology of multiple inflammatory or autoimmune disorders in humans. IL-17 protein and Th17 CD4+ T cells are found in lesions from multiple sclerosis patients[6-8] where they are thought to contribute to the disruption of the blood-brain barrier[9]. IL-17 is produced by CD4+ T cells of rheumatoid synovium[10] and is thought to contribute to inflammation in rheumatoid arthritis[11, 12]. In psoriasis, products associated with Th17 cells, including IL-17, IL-17F, IL-22, and CCR6 are induced[13-15]. IL-17 is induced in the gut mucosa from Crohn's disease and ulcerative colitis patients and Th17 cells are detected[13, 16]. IL-23, which is produced by dendritic cells in the intestine[17], contributes significantly to Th17 cell differentiation[18]. Strikingly, polymorphisms in the IL23R gene are associated with Crohn's disease, further implicating the Th17 cell pathway in the pathogenesis of this disease[19].

The mechanisms leading to differentiation of Th17 cells have been well established in mice but they are still poorly understood in humans. In mice, differentiation of Th17 cells that secrete IL-17 (also referred to as IL-17A) and IL-17F requires the expression of the transcription factors Rorγt, an orphan nuclear hormone receptor, STAT3 and IRF4 (reviewed in[20]). Rorγt is sufficient to direct expression of IL-17 in activated mouse T cells[21] and is thus considered to be the effector transcription factor that establishes the Th17 differentiation lineage. Conditions that induce Th17 cell differentiation from naive murine T cells, including expression of Rorγt, have been established. Combinations of TGF-β and IL-6[22-24] or TGF-β and IL-21[25-27] are sufficient to initiate IL-17 and IL-17F expression. Expression of IL-22, considered to be another Th17 cytokine, is induced by IL-6 and inhibited by high concentrations of TGF-β[14]. IL-23 is required in vivo for the generation of pathogenic Th17 cells, but it is not required in vitro for the induction of IL-17, IL-17F or IL-22[18].

In contrast to murine T cells, human T cells with a naive surface phenotype fail to produce IL-17 in the presence of TGF-β and IL-6[28-31]. Increased expression of IL-17 was, however, observed by some groups in response to IL-1β alone[29] or with IL-23[15]. Others have failed to observe such a response[30]. These disparate findings reveal that the identities of the exogenous factors required to induce the differentiation of human Th17 cells remain unknown. The difference between the requirements for mouse and human Th17 cell differentiation have been ascribed to divergent differentiation processes, although it remains possible that T cells purified from adult peripheral blood on the basis of CD45RA expression alone are not equivalent to naive murine T cells[32-34].

SUMMARY OF INVENTION

Th17 cells are IL-17-secreting CD4+ T cells involved in autoimmune disease and mucosal immunity. In naive CD4+ T cells from mice, IL-17 is expressed in response to a combination of IL-6 or IL-21 and TGF-β and requires induction of the transcription factor Rorγt. It has been suggested that human Th17 cell differentiation is independent of TGF-β and thus differs fundamentally from mouse. The present inventors demonstrate here that, in serum-free conditions, a combination of TGF-β with IL-1β and any one of IL-6, IL-21 or IL-23 is necessary and sufficient to induce IL-17 expression in naive human CD4+ T cells isolated from cord blood.

In one aspect, the present invention is directed to a method for promoting differentiation and proliferation of human T helper lymphocytes that express IL17 (Th-IL17+ cells) in vitro, the method comprising the steps of: isolating a population of naive CD4+T cells from a human; and incubating the population of naive CD4+T cells in serum-free culture medium comprising TGF-β, IL-1β, and any one of IL-6, IL-21 or IL-23, wherein the incubating promotes differentiation of human Th-IL17+ cells. Detecting an increase in expression of any cellular marker of human Th-IL17+ differentiation, such as IL17, IL17F, IL23R, RORC or IL26, after incubating in human Th-IL17+ promoting conditions may be used as a positive indicator of Th-IL17+ cell differentiation.

In another aspect, the invention is directed to a method for generating a population of human T helper lymphocytes that express IL17 (Th-IL17+ cells) in vitro, the method comprising the steps of: isolating a population of naive CD4+T cells from a human; and incubating the population of naive CD4+T cells in serum-free culture medium comprising TGF-β, IL-1β, and any one of IL-6, IL-21 or IL-23, wherein the incubating promotes differentiation and proliferation of human Th-IL17+ cells and thereby generates a population of human Th-IL17+ cells.

The naive CD4+T cells used in the present method may be isolated from cord blood, buffy coats of adult humans, cell cultures comprising cells that express CD34 (CD34+ cells), or human embryonic stem cells. CD34+ cells may be isolated from fetal liver, cord blood, or mobilized adult blood and further expanded in vitro to generate cell cultures comprising CD34+ cells.

In an embodiment of the invention, the concentration of TGF-β in the serum-free culture medium is at least 0.1 ng/ml. In a more particular embodiment, the concentration of TGF-β in the serum-free culture medium is about 10 ng/ml or is 10 ng/ml.

In an embodiment of the invention, the concentration of IL-1β in the serum-free culture medium is at least 0.1 ng/ml. In a more particular embodiment, the concentration of IL-1β in the serum-free culture medium is about 10 ng/ml or is 10 ng/ml.

In an embodiment of the invention, the concentration of IL-6 in the serum-free culture medium is at least 0.1 ng/ml. In a more particular embodiment, the concentration of IL-6 in the serum-free culture medium is about 10 ng/ml or is 10 ng/ml.

In an embodiment of the invention, the concentration of IL-21 in the serum-free culture medium is at least 0.1 ng/ml. In a more particular embodiment, the concentration of IL-21 in the serum-free culture medium is about 10 ng/ml or is 10 ng/ml.

In an embodiment of the invention, the concentration of IL-23 in the serum-free culture medium is at least 0.1 ng/ml. In a more particular embodiment, the concentration of IL-23 in the serum-free culture medium is about 10 ng/ml or is 10 ng/ml.

In yet another embodiment of the invention, the serum-free culture medium further comprises IL-2. More particularly, the concentration of IL-2 in the serum-free culture medium is at least 1 U/ml. Even more particularly, the concentration of IL-2 in the serum-free culture medium is about 10 U/ml or is 10 U/ml.

In an aspect of the invention, the population of CD4+T cells is activated with anti-CD3 and anti-CD28 antibodies prior to or concomitant with the incubating step.

In another aspect of the invention, the incubating step is at least three days. More particularly, the incubating step is about six days or is six days.

The invention also encompasses a method wherein the population of CD4+T cells is transduced with a lentiviral vector comprising a nucleic acid sequence encoding an exogenous polypeptide RORγT before or during the incubating step. More particularly, the lentiviral vector comprises a nucleic acid sequence encoding RORγT or RORγ. The nucleic and amino acid sequences of human and mouse RORγT and RORγ are presented herein. As understood in the art, the gene RORC encodes RORγ and RORγT, which are isoform a and b, respectively, of RORC. In another embodiment of the invention, the lentiviral vector comprises a nucleic acid sequence encoding human RORα or human RORβ, which can also drive IL-17 expression in human CD4+ cells. Nucleic acid sequences encoding human RORα or human RORβ are presented herein.

The invention also encompasses a method wherein the population of CD4+T cells is isolated based on positive cell surface staining for cell surface antigens or receptors. Exemplary cell surface antigens or receptors include putative homing receptors: CCR7, CCR6, CCR5, CXCR4, CD62L, CD44, CD11a, CD27, CD57, and CD49f.

The invention also encompasses a method wherein the population of CD4+T cells is isolated based on positive cell surface staining for a particular T cell receptor. In an embodiment of the invention, the T cell receptor is specific for a particular tumor cell antigen.

The method of the present invention may further comprise an enrichment step, whereby post-incubation cells (i.e., cells that have been incubated in accordance with the invention) are selected for expression of a cell surface marker or cell surface antigen expressed on human Th-IL17+ cells. More particularly, the cell surface marker or cell surface antigen expressed on human Th-IL17+ cells is CCR6, CCR7, CCR5, and CXCR4.

The present invention also encompasses a method for screening to identify an agent that modulates human Th-IL17+ cell differentiation in vitro, the method comprising the steps of:

a) isolating a population of CD4+T cells from a human and dividing the population into at least a first and second sub-population of CD4+ T cells;

b) incubating a first sub-population of CD4+T cells in serum-free culture medium comprising TGF-β, IL-1β, and any one of IL-6, IL-21 or IL-23, wherein the incubating promotes differentiation of human Th-IL17+ cells;

c) incubating a second sub-population of CD4+T cells in serum-free culture medium comprising TGF-β, IL-1β, and any one of IL-6, IL-21 or IL-23, and an agent;

d) detecting expression of IL17, IL17F, IL23R, RORC or IL26 in each of said first and second sub-populations of CD4+T cells incubated without or with the agent;

e) comparing the expression of IL17, IL17F, IL23R, RORC, IL26, or FOXP3 in each of said first and second sub-populations of CD4+T cells generated following incubation without or with the agent, wherein a change in expression of IL17, IL17F, IL23R, RORC, IL26, or FOXP3 following incubation with the agent relative to the expression of IL17, IL17F, IL23R, RORC, IL26, or FOXP3 following incubation without the agent indicates that the agent is a modulator of human Th-IL17+ cell differentiation in vitro.

In another embodiment of the invention, the serum-free culture medium of the screening method further comprises IL-2. More particularly, the concentration of IL-2 in the serum-free culture medium is at least 1 U/ml. Even more particularly, the concentration of IL-2 in the serum-free culture medium is about 10 U/ml or is 10 U/ml.

In an aspect of the screening method, the change in expression of IL17, IL17F, IL23R, RORC or IL26 is a decrease in expression of IL17, IL17F, IL23R, RORC or IL26 following incubation with the agent, wherein the decrease indicates that the agent is an inhibitor of human Th-IL17+ cell differentiation in vitro.

In another aspect of the screening method, the change in expression of IL17, IL17F, IL23R, RORC or IL26 is an increase in expression of IL17, IL17F, IL23R, RORC or IL26 following incubation with the agent, wherein the increase indicates that the agent is a promoter or inducer of human Th-IL17+ cell differentiation in vitro.

In yet another aspect of the invention, expression of FOXP3 is used as a target for readout of the methods described herein. FOXP3 is a negative regulator of human Th-IL17+ cell differentiation. Thus, in a screening method of the invention, a practitioner could screen for an inhibitor of Th17 that could increase FOXP3 expression and an inducer of Th17 that could inhibit FOXP3 expression. Given the role of FOXP3 in autoimmunity, the identification of such inhibitors and inducers would provide promising therapeutics.

With respect to the screening method, therefore, a decrease in expression of FOXP3 following incubation with an agent indicates that the agent is a promoter of human Th-IL17+ cell differentiation in vitro. In contrast, an increase in expression of FOXP3 following incubation with an agent indicates that the agent is an inhibitor of human Th-IL17+ cell differentiation in vitro.

As described herein, the agent used in the screening method of the invention may be a small molecule; polypeptide; azole-containing compounds; cholesterol derivative compounds; retinoid derivative compounds; shRNA/siRNA; neutralizing/blocking antibodies; tryptophan derivative compounds; Vitamin D derivatives; or molecules known to inhibit of fever, inflammation, or regulatory T (Treg) cell differentiation.

An agent tested in a screening method of the invention may be added to the culture medium before, during, or after addition of TGF-β, IL-1β, and any one of IL-6, IL-21 or IL-23.

In an aspect of the screening method, expression of IL17, IL17F, IL23R, RORC or IL26 is determined by polymerase chain reaction amplification using primer pairs specific for IL17, IL17F, IL23R, RORC or IL26.

The present invention further encompasses an isolated homogeneous population of human Th-IL17+ cells, wherein the isolated homogeneous population comprises at least $1 \times 10^9$ human Th-IL17+ cells, wherein the human Th-IL17+ cells do not express cellular markers of other differentiated Th cells. In accordance with the present invention, the isolated homogeneous population of human Th-IL17+ cells generated from naive CD4+ cells do not express cellular markers characteristic of Th1 (e.g., IFNγ), Th2 (e.g., IL4 or IL13), or Treg cells (e.g., FoxP3). It is understood that cellular markers characteristic of Th1, Th2, or Treg cells would be present in any population of Th-IL17+ cells generated from memory Th cells. The isolated population of human Th-IL17+ cells generated from naive CD4+ cells as described herein is, therefore, homogeneous with respect to the expression of only those cellular markers characteristic of Th17+ cells. Exemplary markers of human Th-IL17 cells are IL-17, IL-17F, IL-26, and IL23R.

Other features and advantages of the invention will be apparent from the following description of the particular embodiments thereof, and from the claims.

GenBank accession numbers and amino acid identity to human IL-26 are indicated. Human IL-22 is shown for comparison.

Figure 8:
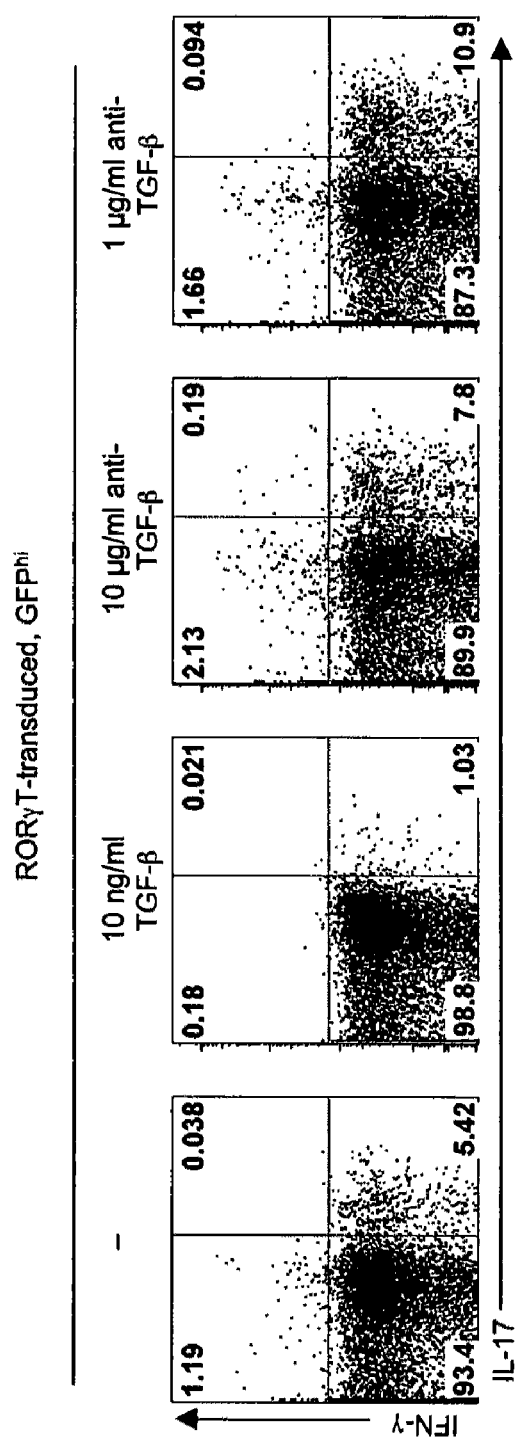

FIG. 8: TGF-β anti-TGF-β effect on IL-17 expression following RORγT transduction. Naive cord blood CD4+ T cells were transduced with RORγT in RPMI-10% FBS alone, with recombinant TGF-β or with an anti-TGF-β antibody. IL-17 and IFNγ expression was analyzed at day 6 in GFP$^{hi}$ cells.

Figure 9:
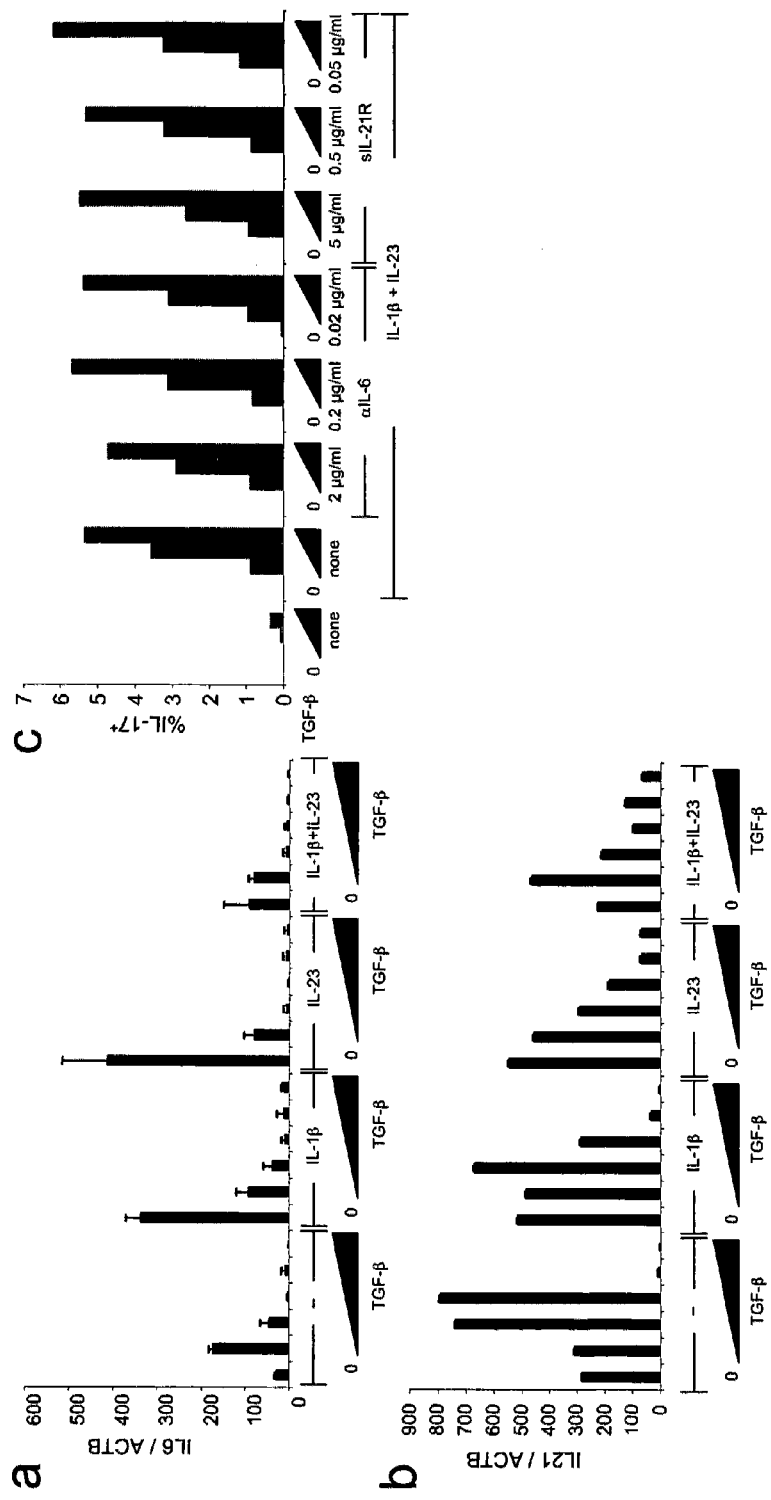

FIG. 9*a-c*: Expression and neutralization of IL-6 and IL-21. (a, b) Naive cord blood CD4+ T cells were cultivated in IL-2 alone or, IL-1β+IL-2, IL-23+IL-2, or IL-23+IL-2 with increasing concentrations of TGF-β. mRNA levels of β-actin, IL6 (a) and IL21 (b) was analyzed on day 6 following restimulation with PMA and ionomycin. (c) Naive cord blood CD4+ T cells were cultivated in IL-2 alone or, IL-23+IL-1β+IL-2 with increasing concentrations of TGF-β. Increasing concentrations of neutralizing anti-IL-6 antibody and soluble IL-21 receptor were also added. IL-17 expression was analyzed at day 6.

Figure 10:
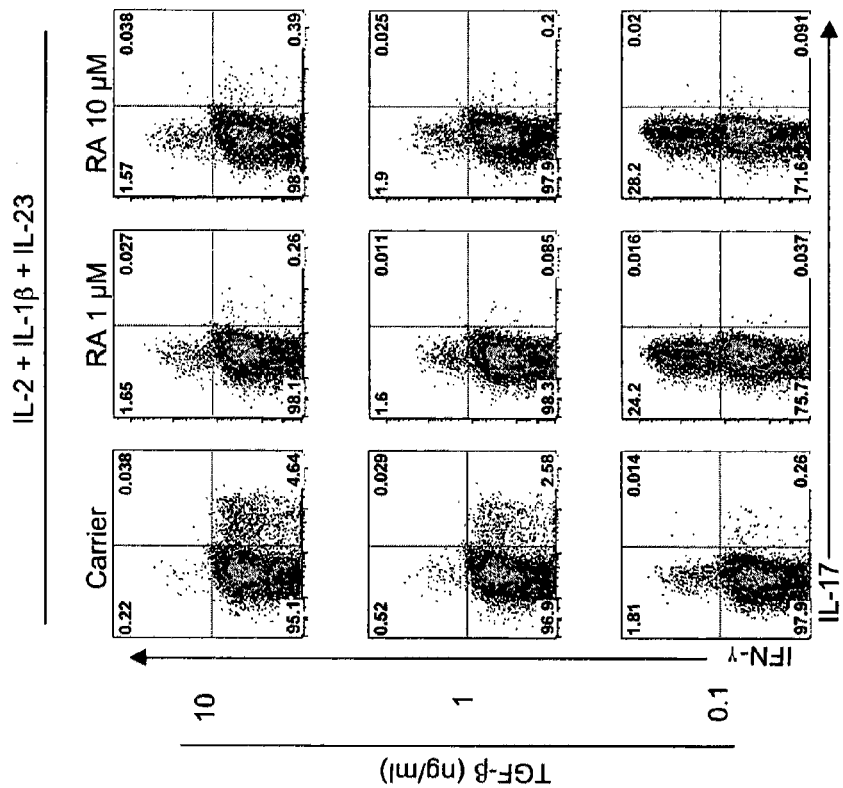

FIG. 10: Retinoic acid inhibits IL-17 induction. Naive cord blood CD4+ T cells were activated with a combination of IL-2+IL-1β+IL-23+TGF-β (0.1, 1 and 10 ng/ml), with or without retinoic acid (10 and 100 nM). IL-17 and IFNγ expression was analyzed at day 6.

Figure 11:
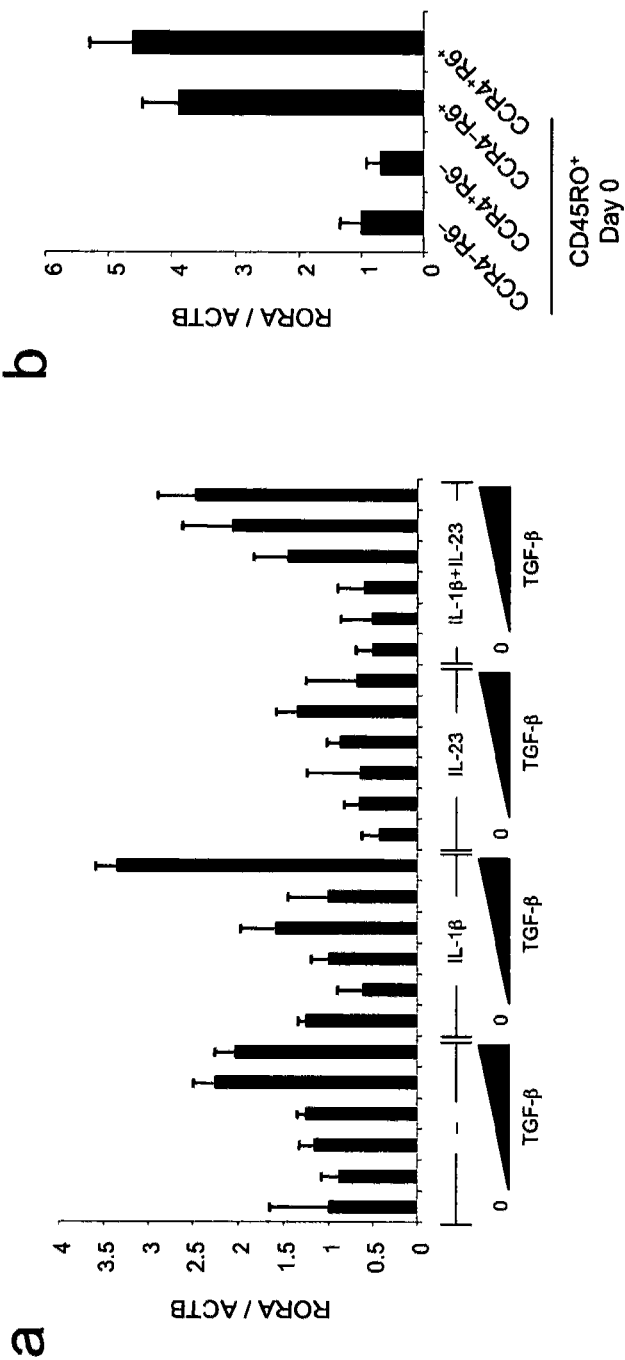

FIG. 11*a-b*: Expression of RORA. (a) Naive cord blood CD4+ T cells were cultivated in IL-2 alone or, IL-1β+IL-2, IL-23+IL-2, or IL-23+IL-1β+IL-2 with increasing concentrations of TGF-β. mRNA levels of β-actin and RORA were analyzed on day 6. (b) RORA and β-actin expression was measured in freshly sorted CCR4$^{-/+}$CCR6$^{-/+}$ adult memory CD4+ T cells.

DETAILED DESCRIPTION OF THE INVENTION

In order to more clearly set forth the parameters of the present invention, the following definitions are used:

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

The term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction.

With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID No. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the term "operably linked" refers to a regulatory sequence capable of mediating the expression of a coding sequence and which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Primers may be labeled fluorescently with 6-carboxyfluorescein (6-FAM). Alternatively primers may be labeled with 4,7,2',7'-Tetrachloro-6-carboxyfluorescein (TET). Other alternative DNA labeling methods are known in the art and are contemplated to be within the scope of the invention.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More particularly, the preparation comprises at least 75% by weight, and most particularly 90-95% by weight of the given compound. Purity is measured by methods appropriate for the given compound (e.g. chromatographic methods, agarose or polyacrylamide gel electrophoresis, HPLC analysis, and the like). "Mature protein" or "mature polypeptide" shall mean a polypeptide possessing the sequence of the polypeptide after any processing events that normally occur to the polypeptide during the course of its genesis, such as proteolytic processing from a polypeptide precursor. In designating the sequence or boundaries of a mature protein, the first amino acid of the mature protein sequence is designated as amino acid residue 1.

The term "tag", "tag sequence" or "protein tag" refers to a chemical moiety, either a nucleotide, oligonucleotide, polynucleotide or an amino acid, peptide or protein or other chemical, that when added to another sequence, provides additional utility or confers useful properties to the sequence, particularly with regard to methods relating to the detection or isolation of the sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

The terms "transform", "transfect", "transduce", shall refer to any method or means by which a nucleic acid is introduced into a cell or host organism and may be used interchangeably to convey the same meaning. Such methods include, but are not limited to, viral transduction, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunloglobulin molecule such as those portions known in the art as Fab, Fab', F(ab')2 and F(v).

The term "about" as used herein refers to a variation in a stated value or indicated amount of up to 10%, 9%, 8%, 7%, 6%, 5%, 4%, 3%, 2%, 1%, 0.75%, 0.5%, 0.25% or 0.1%, wherein the variation can be either an increase or a decrease in the stated value or indicated amount. Use of the term may, therefore, be used to establish a range of values or amounts.

As used herein, the term "naive CD4+ T cells" refers to a CD4+ T cell that is functionally defined by the expression of cell surface markers of naivety that include CD45RA+CD25-HLA-DR-.

As used herein, the term "serum-free culture medium" is defined as serum-free cell culture medium that has a defined chemical composition and supports proliferation of human lymphocytes. A list of serum-free culture medium useful in the present invention would include, without limitation, LONZA XVIVO-5, XVIVO-10, XVIVO-20, Sigma StemLine I, StemLine II, Yssel's media and AimV media.

Exemplary serum-free medium is described in the Example section presented herein. An exemplary serum-free medium is serum-free XVIVO-20 (Lonza), which may optionally be supplemented with penicillin-streptomycin.

MEM and RPMI are protein-free basal media that do not contain growth factors required for lymphocytes. A skilled practitioner would appreciate that a protein-free basal media can, however, be converted to serum-free media capable of supporting lymphocyte proliferation following addition of required growth factors. Such serum-free media contain specific and defined growth factors (e.g., insulin) that are required for lymphocyte proliferation.

In Vitro Methods

As described herein, the present invention is directed to a method for promoting differentiation and proliferation of human T helper lymphocytes that express IL17 (Th-IL17+ cells) in vitro, the method comprising the steps of: isolating a population of naive CD4+T cells from a human; and incubating the population of naive CD4+T cells in serum-free culture medium comprising TGF-1β, IL-1β, and any one of IL-6, IL-21 or IL-23, wherein the incubating promotes differentiation of human Th-IL17+ cells.

As also described herein, the invention is directed to a method for generating a population of human T helper lymphocytes that express IL17 (Th-IL17+ cells) in vitro, the method comprising the steps of: isolating a population of naive CD4+T cells from a human; and incubating the population of naive CD4+T cells in serum-free culture medium comprising TGF-β, IL-1β, and any one of IL-6, IL-21 or IL-23, wherein the incubating promotes differentiation and proliferation of human Th-IL17+ cells and thereby generates a population of human Th-IL17+ cells.

The in vitro methods of the invention are based on the novel and surprising discoveries of the present inventors. In short, the present inventors have devised an in vitro method for promoting human Th-IL17+ cell differentiation and proliferation, which also provides a method for generating in vitro a population of human Th-IL17+ cells. The method calls for incubation of naive CD4+ T cells in serum-free media supplemented with TGF-β, IL-1β, and any one of IL-6, IL-21 or IL-23. As described herein, "serum-free media comprising TGF-β, IL-1β, and any one of IL-6, IL-21 or IL-23", refers to serum-free media comprising TGF-β, IL-1β, and any one of IL-6, IL-21 or IL-23 in amounts effective for promoting human Th-IL17+ cell differentiation. Conditions wherein naive CD4+ cells are incubated in serum-free media comprising TGF-β, IL-1β, and any one of IL-6, IL-21 or IL-23 may also be referred to herein as human Th-IL17+ cell promoting conditions. A negative control for human Th-IL17+ cell promoting conditions is a matched serum-free media without cytokine supplementation (i.e., without TGF-β, IL-1β, and any one of IL-6, IL-21 or IL-23). An exemplary negative control for human Th-IL17+ cell promoting conditions is a matched serum-free media alone. It is to be understood that supplementation with standard media additives for prevention of bacterial or fungal infection (such as, e.g., penicillin-streptomycin) is not precluded from the method of the present invention. Indeed, in a particular embodiment of the present invention, the method calls for serum-free media comprising TGF-β, IL-1β, and any one of IL-6, IL-21 or IL-23, which is supplemented with penicillin-streptomycin. It is to be further understood that human Th-IL17+ cell promoting conditions may also include additional cytokine supplementation as described herein.

As taught herein, in vitro differentiation of human Th-IL17+ cells may be evaluated or measured by detecting an increase in the expression of a human Th-IL17+ cell marker, such as IL17, IL17F, IL23R, RORC or IL26, in a population of CD4+T cells incubated in accordance with the present method. Each of these cellular molecules (IL17, IL17F, IL23R, RORC or IL26) serves as a positive marker indicative of human Th-IL17+ cell differentiation. Indeed, expression of IL17, IL17F, IL23R, RORC or IL26 is induced by 10- to about 100-fold in CD4+ cells incubated in human Th-IL17+ cell promoting conditions relative to those treated under negative control conditions. Accordingly, a change in the expression of at least one of these markers reflects a differential in human Th-IL17+ cell differentiation. More particularly, a change in the expression of at least one of these markers reflects a differential in human Th-IL17+ cell differentiation in a population of CD4+ cells incubated in human Th-IL17+ promoting conditions. A change in expression of any of these markers may be determined using a variety of experimental protocols, including, but not limited to, real-time PCR using appropriate primers. Experimental protocols that can be used to determine expression of such markers and relative expression levels are described in detail herein and are understood in the art.

In serum-free conditions in the absence of TGF-β, IL-1β, and any one of IL-6, IL-21 or IL-23, Th17 markers do not increase. The present inventors were, however, the first to define intermediate conditions, such as, e.g., that TGFβ alone induces RORγT expression and CCR6 expression, but not IL-17. Such intermediate conditions represent those conditions necessary to achieve a partial progression along the pathway of Th-17+ cell differentiation.

Agents

As used herein, an "agent", "candidate compound", or "test compound" may be used to refer to, for example, nucleic acids (e.g., DNA and RNA), carbohydrates, lipids, proteins, peptides, peptidomimetics, small molecules and other drugs. More particularly an agent may refer to azole-containing compounds, cholesterol derivative compounds, retinoid derivative compounds, short hairpin RNA (shRNA), small interfering RNA (siRNA), neutralizing and/or blocking antibodies, tryptophan derivative compounds, Vitamin D derivatives, or molecules known to inhibit fever, inflammation, or regulatory T (Treg) cell differentiation.

A short hairpin RNA (shRNA) is a sequence of RNA that makes a tight hairpin turn that can be used to silence gene expression via RNA interference. shRNA is generally expressed using a vector introduced into cells, wherein the vector utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA to which it is bound.

Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway whereby the siRNA interferes with the expression of a specific gene.

Azole-containing compounds are chemical compounds that contain at least an azole group. Azole groups are five-membered nitrogen heterocyclic ring compounds containing at least one other noncarbon atom, nitrogen, sulfur or oxygen. Azole groups are aromatic and have two double bonds. Azole-containing compounds comprise the family of Imidazole and triazole antifungals (e.g. Clotrimazole).

Sterol derivative compounds are compounds that are, for instance, intermediate in the pathway of cholesterol synthesis (mevalonate pathway). That includes lanosterol, FF-MAS (follicular fluid-meiosis-activating sterol).

Retinoid derivatives are compounds structurally related to Vitamin A and include, without limitation, retinoic acid.

Tryptophan derivative compounds are compounds that are generated from the degradation of tryptophan, through the action of, for instance, metabolism (Action of the IDO enzyme) or UVB radiation.

Vitamin D derivatives are compounds that are structurally related to Vitamin D and that include 1-25VitaminD3.

As described herein, an agent identified using the method of the present invention that is a "modulator of human Th-IL17+ cell differentiation" is defined as an agent that is capable of modulating (e.g., increasing or decreasing) in vitro differentiation of human Th-IL17+ cells. Such an agent may be identified by its ability to effect a change in the expression of a human Th-IL17+ cell marker, such as IL17, IL17F, IL23R, RORC or IL26, in a population of CD4+ T cells incubated in human Th-IL17+ cell promoting conditions. As described herein, each of these cellular molecules (IL17, IL17F, IL23R, RORC or IL26) serves as a positive marker indicative of human Th-IL17+ cell differentiation. Expression of IL17, IL17F, IL23R, RORC or IL26 can be induced by 10- to 100-fold in CD4+ T cells treated to promote Th-IL17+ cell differentiation relative to those treated under negative control conditions in accordance with the method of the present invention. In contrast, FOXP3 expression is inversely correlated with human Th-IL17+ cell differentiation. FOXP3, therefore, serves as a negative marker of human Th-IL17+ cell differentiation. Accordingly, a change in the expression of at least one of these markers (positive or negative) responsive to the presence of an agent reflects a differential in human Th-IL17+ cell differentiation. More particularly, a change in the expression of at least one of these markers reflects a differential in human Th-IL17+ cell differentiation in a population of cells incubated in human Th-IL17+ cell promoting conditions, wherein the change is dependent on incubation in the presence of a particular agent. As detailed below, experimental protocols of utility in determining expression of such markers and relative expression levels are described in detail herein and are understood in the art. Such experimental protocols, include, but are not limited to, real-time PCR using appropriate primers.

As taught herein, the change effected by an agent that is a modulator of human Th-IL17+ cell differentiation is determined relative to that of a population of CD4+T cells incubated in parallel in the absence of the agent or in the presence of a control agent (as described below), either of which is analogous to a negative control condition.

In accordance with the present invention, the method described herein may be used to achieve an increase in the number of human Th17+ cells in a cell population incubated in human Th-IL17+ cell promoting conditions, as described herein. An increase in the number of human Th17+ cells in such a cell population may be expressed as the percent (%) of human Th17+ cells present in such a cell population relative to the total number of cells. In accordance with the present invention, the method described herein typically achieves 1% to 15% human Th17+ cells in a cell population. It will be appreciated, however, that the present method may be used to achieve a higher relative percent human Th17+ cells in a cell population. Accordingly, the present invention is not in any way limited to achieving 1% to 15% human Th17+ cells in a treated cell population.

In light of the above, it will be appreciated that an agent identified using the method of the present invention that is a "modulator of human Th-IL17+ cell differentiation" may be identified by its ability to effect a change in the percent of human Th17+ cells in a population of CD4+ T cells incubated in human Th-IL17+ cell promoting conditions. As taught herein, a change in the percent of human Th17+ cells in a population of CD4+ T cells incubated in the presence of an agent is determined relative to the percent of human Th17+ cells in a population of CD4+T cells incubated in the absence of the agent or in the presence of a control agent (negative control condition).

The term "control substance", "control agent", or "control compound" as used herein refers a molecule that is inert or has no activity relating to an ability to modulate a biological activity. With respect to the present invention, such control substances are inert with respect to an ability to modulate human Th-IL17+ cell differentiation in vitro. Exemplary controls include, but are not limited to, solutions comprising physiological salt concentrations.

In accordance with the present invention, incubation in the presence of an agent that results in a decrease in expression of a human Th-IL17+ cell marker, such as IL17, IL17F, IL23R, RORC or IL26, indicates that the agent is an inhibitor of human Th-IL17+ cell differentiation in vitro. An agent that results in a decrease in expression of a human Th-IL17+ cell marker, such as IL17, IL17F, IL23R, RORC or IL26, is referred to herein as an inhibitor of human Th-IL17+ cell differentiation. An inhibitor of human Th-IL17+ cell differentiation is an agent that effects at least a 2-fold decrease in the expression of a human Th-IL17+ cell marker, such as IL17, IL17F, IL23R, RORC or IL26. More particularly, an inhibitor of human Th-IL17+ cell differentiation is an agent that effects at least a 3-fold decrease in the expression of a human Th-IL17+ cell marker, such as IL17, IL17F, IL23R, RORC or IL26. The above fold decreases may be determined relative to human Th-IL17+ cell marker expression levels induced by incubation in human Th-IL17+ cell promoting conditions in the absence of the agent.

In accordance with the present invention, incubation in the presence of an agent that results in an increase in expression of a human Th-IL17+ cell marker, such as IL17, IL17F, IL23R, RORC or IL26, indicates that the agent is a promoter of human Th-IL17+ cell differentiation in vitro. An agent that results in an increase in expression of a human Th-IL17+ cell marker, such as IL17, IL17F, IL23R, RORC or IL26, is referred to herein as a promoter of human Th-IL17+ cell differentiation. A promoter of human Th-IL17+ cell differentiation is an agent that effects at least a 2-fold increase in the expression of a human Th-IL17+ cell marker, such as IL17, IL17F, IL23R, RORC or IL26. More particularly, a promoter of human Th-IL17+ cell differentiation is an agent that effects at least a 3-fold increase in the expression of a human Th-IL17+ cell marker, such as IL17, IL17F, IL23R, RORC or IL26. The above fold increases may be determined relative to human Th-IL17+ cell marker expression levels induced by incubation in human Th-IL17+ cell promoting conditions in the absence of the agent.

Also in accordance with the present invention, incubation in the presence of an agent that results in a decrease in expression of FOXP3 (expression of which is inversely correlated with human Th-IL17+ cell differentiation) indicates that the agent is a promoter or inducer of human Th-IL17+ cell differentiation in vitro. An agent that results in a decrease in expression of FOXP3 is, therefore, referred to herein as a promoter or inducer of human Th-IL17+ cell differentiation. A promoter or inducer of human Th-IL17+ cell differentiation is an agent that effects at least a 2-fold decrease in the expression of FOXP3. More particularly, a promoter or inducer of human Th-IL17+ cell differentiation is an agent that effects at least a 3-fold decrease in the expression of FOXP3. The above fold decreases are determined relative to FOXP3 expression levels observed under matched control conditions, but in the absence of the agent.

Also in accordance with the present invention, incubation in the presence of an agent that results in an increase in expression of FOXP3 (expression of which is inversely correlated with human Th-IL17+ cell differentiation) indicates that the agent is an inhibitor of human Th-IL17+ cell differentiation in vitro. An agent that results in an increase in expression of FOXP3 is, therefore, referred to herein as an inhibitor of human Th-IL17+ cell differentiation. An inhibitor of human Th-IL17+ cell differentiation is an agent that effects at least a 2-fold increase in the expression of FOXP3. More particularly, an inhibitor of human Th-IL17+ cell differentiation is an agent that effects at least a 3-fold increase in the expression of FOXP3. The above fold increases are determined relative to FOXP3 expression levels observed under matched control conditions, but in the absence of the agent.

In accordance with the present invention, incubation in the presence of an agent that results in a decrease in the percent of human Th17+ cells generated indicates that the agent inhibits human Th-IL17+ cell differentiation in vitro. Such an agent is referred to herein as an inhibitor of human Th-IL17+ cell differentiation. An inhibitor of human Th-IL17+ cell differentiation is an agent that effects at least a 2-fold decrease in the percent of human Th17+ cells generated. More particularly, an inhibitor of human Th-IL17+ cell differentiation is an agent that effects at least a 3-fold decrease in the percent of human Th17+ cells generated. The above fold decreases may be determined relative to the percent of human Th17+ cells generated by incubation in human Th-IL17+ cell promoting conditions in the absence of the agent.

In accordance with the present invention, incubation in the presence of an agent that results in an increase in the percent of human Th17+ cells generated indicates that the agent promotes human Th-IL17+ cell differentiation in vitro. Such an agent is referred to herein as a promoter/inducer of human Th-IL17+ cell differentiation. A promoter or inducer of human Th-IL17+ cell differentiation is an agent that effects at least a 2-fold increase in the percent of human Th17+ cells generated. More particularly, a promoter/inducer of human Th-IL17+ cell differentiation is an agent that effects at least a 3-fold increase in the percent of human Th17+ cells generated. The above fold increases may be determined relative to the percent of human Th17+ cells generated by incubation in human Th-IL17+ cell promoting conditions in the absence of the agent.

It is to be understood that agents capable of modulating human Th-IL17+ cell differentiation, as determined using the in vitro method described herein, are likely to exhibit similar modulatory capacity in applications in vivo.

Modulatory agents identified using the screening methods of the present invention and compositions thereof can thus be administered for therapeutic treatments. In therapeutic applications, modulatory agents that inhibit Th17+ T cell differentiation (i.e., inhibitors of Th17+ T cell differentiation) and compositions thereof are administered to a patient suffering from an inflammatory or autoimmune disorder in an amount sufficient to at least partially arrest a symptom or symptoms of the disease and its complications. An amount adequate to accomplish this is defined as a "therapeutically effective amount or dose." Amounts effective for this use will depend on the severity of the disease and the weight and general state of the patient.

Examples of inflammatory or autoimmune disorders that may be treated using inhibitors of Th17+ T cell differentiation include, without limitation, multiple sclerosis, rheumatoid arthritis, Crohn's disease, and ulcerative colitis.

Methods for Determining Expression Levels of Human Th-IL17+ Cell Markers

Based on the guidance presented herein and knowledge in the relevant scientific fields, the expression level of a cellular marker of human Th-IL17+ cells can be determined using a variety of techniques. Exemplary markers of human Th-IL17+ cell differentiation include, but are not limited to, IL17, IL17F, IL23R, RORC and IL26. Expression of FOXP3, on the other hand, is negatively correlated with human Th-IL17+ cell differentiation. FOXP3 is, therefore, a negative marker of human Th-IL17+ cell differentiation. Expression levels of such markers (either a positive or a negative marker) may be assessed with respect to expressed nucleic acid corresponding to a cell marker (e.g., mRNA, total RNA) or with respect to polypeptides encoded by same. A variety of standard protocols may be used to determine, for example, RNA level, including, but not limited to: polymerase chain amplification and detection of amplified products therefrom, ribonuclease protection (RNase protection) assay, and Northern blot analysis. The principles and general procedures of each of these methods are described in, for example, Dvorak et al. (Biomed Papers 147:131, 2003), which is incorporated herein in its entirety. The principles and general procedures of each of these methods are, moreover, known in the art. In a particular embodiment of the invention, real-time PCR is used to detect gene expression of human Th-IL17+ cell markers.

Real-Time PCR

As taught herein, detection of IL-17, IL17F, IL23R, RORC or IL26 gene expression may be used as a means to assess human Th-IL17+ differentiation. Detection of these markers of human Th-IL17+ differentiation, therefore, provides positive indicators or readouts for the present method for promoting differentiation and proliferation of human Th-IL17+ differentiation. The induction of these genes in Th17 promoting conditions is at least 10-fold, and can achieve about 100-fold relative to the levels of these genes in non-promoting conditions. Particulars relating to real-time PCR analysis are presented in the Examples, as are primers for amplification of the above-indicated Th-IL17 markers. See Table 2.

In non-Th17 promoting conditions, there are detectable levels of the Th-IL17 marker genes at the level of RNA, but there is no detectable protein. The absence of detectable protein, therefore, presents a relevant baseline against which to compare Th-IL17 marker protein levels.

Detection of FOXP3 gene expression may also be used as a means to assess human Th-IL17+ differentiation. Detection of this negative marker of human Th-IL17+ differentiation provides a negative indicator or readout for the present method for promoting differentiation and proliferation of human Th-IL17+ differentiation. A reduction in FOXP3 gene expression, however, provides a positive indicator or readout for the present method for promoting differentiation and proliferation of human Th-IL17+ differentiation. The reduction of FOXP3 expression in Th17 promoting conditions is at least two-fold, and can achieve about ten-fold relative to the levels of this gene in non-promoting conditions.

A variety of protocols are available for measuring and/or detecting expression levels of polypeptides. Protocols for detecting polypeptide expression, such as, for example, immunohistochemistry and immunoblotting, are known in the art. These protocols are generally applicable to detecting IL17, IL17F, IL23R, RORC, IL26, or FOXP3 polypeptides. Particular methods for detecting IL17, IL17F, IL23R, RORC, IL26, or FOXP3 polypeptides are described in the Examples presented herein, as are reagents for performing such methods.

In general, immunoassays for polypeptides typically comprise contacting a sample, such as a population of cells (e.g., incubated in Th17 promoting conditions or lysates thereof) in the presence of an antibody that specifically or selectively binds to a polypeptide in question, e.g., a detectably labeled antibody capable of identifying, the particular polypeptide (e.g., IL-17), and detecting the bound antibody by any of a number of techniques well-known in the art (e.g., Western blot, ELISA, FACS).

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled antibody that selectively or specifically binds to the particular polypeptide (e.g., a Th17 cell marker). The solid phase support may then be washed with the buffer a second time to remove unbound antibody. The amount of bound label on a solid support may then be detected by conventional means.

More particularly, Th-IL17 marker protein levels can be assessed by cell surface staining for CCR6 and IL23R; ELISA for IL-17, IL-17F, and IL-26; intracellular staining for IL17, IL17F, IL26, FOXP3 (negative marker), and RORC; and Western Blot for IL-17, IL-17F, IL23R, RORC, IL26, FOXP3 (negative marker).

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Particular supports include polystyrene beads. Those skilled in the art will know many other suitable carriers for binding antibody or antigen, or will be able to ascertain the same by use of routine experimentation.

An antibody can be detectably labeled by linking same to an enzyme and using the labeled antibody in an enzyme immunoassay (EIA) (Voller, A., "The Enzyme Linked Immunosorbent Assay (ELISA)", 1978, *Diagnostic Horizons* 2:1, Microbiological Associates Quarterly Publication, Walkersville, Md.); Voller, A. et al., 1978, *J. Clin. Pathol.* 31: 507-520; Butler, J. E., 1981, *Meth. Enzymol.* 73:482; Maggio, E. (ed.), 1980, *Enzyme Immunoassay*, CRC Press, Boca Raton, Fla.; Ishikawa, E. et al., (eds.), 1981, *Enzyme Immunoassay*, Kgaku Shoin, Tokyo). The enzyme that is bound to the antibody reacts with an appropriate substrate, particularly a chromogenic substrate, in such a manner as to produce a chemical moiety detectable, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect a polypeptide through the use of a radioimmunoassay (RIA). The radioactive isotope can be detected by such means as the use of a gamma counter or a scintillation counter or by autoradiography.

An antibody may also be labeled with a fluorescent compound. When the fluorescently labeled antibody is exposed to light of the proper wavelength, its presence can be detected due to fluorescence emission. Among the most commonly used fluorescent labeling compounds are fluorescein isothiocyanate, rhodamine, phycoerythrin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

An antibody can also be detectably labeled by coupling it to a chemiluminescent compound. The presence of the chemiluminescent-tagged antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label an antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The basic molecular biology techniques used to practice the methods of the invention are well known in the art, and are described for example in Sambrook et al., 1989, *Molecular Cloning: A Laboratory Manual*, Cold Spring Harbor Laboratory, New York; Ausubel et al., 1988, *Current Protocols in Molecular Biology*, John Wiley & Sons, New York; and Ausubel et al., 2002, *Short Protocols in Molecular Biology*, John Wiley & Sons, New York).

Agents Identified by the Screening Methods of the Invention

The invention provides methods for identifying agents (e.g., candidate compounds or test compounds) that modulate (inhibit or promote) human Th-IL17+ differentiation. Agents that are capable of inhibiting human Th-IL17+ differentiation, as identified by the screening method of the invention, are useful as candidate anti-inflammatory or anti-autoimmune disorder therapeutics.

A list of inflammatory or anti-autoimmune disorders that may be treated using an agent identified using a method of the invention includes, without limitation: arthritis, diabetes, multiple sclerosis, uveitis, rheumatoid arthritis, psoriasis, osteoporosis, asthma, bronchitis, allergic rhinitis, chronic obstructive pulmonary disease, atherosclerosis, *H. pylori* infections and ulcers resulting from such infection, graft versus host disease following bone marrow transplantation, and inflammatory bowel diseases. Inflammatory bowel diseases treatable using agents identified by the present methods include Crohn's disease, ulcerative colitis, sprue and food allergies. An inflammatory disease or condition may involve any organ or tissue in which the presence of $T_H17$ cells has been demonstrated and/or implicated in disease etiology. Other diseases known to produce immunopathological damage in the host, which may benefit from treatment with an agent identified using a method of the invention, may be selected from the group consisting of Hepatitis C virus, Influenza, SARS, and respiratory syncytial virus. The involvement of $T_H17$ related genes autotoxin and maspin also suggests that prostate and breast cancers may be treated using an agent identified using a method of the invention. Evidence that the balance of $T_H17$ and Treg cells is specifically altered in human immunodeficiency virus (HIV) infections also suggests that immunodeficiencies and HIV infection may be treated using an agent identified using a method of the invention.

Examples of agents, candidate compounds or test compounds include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145; U.S. Pat. No. 5,738,996; and U.S. Pat. No. 5,807,683, each of which is incorporated herein in its entirety by reference).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233, each of which is incorporated herein in its entirety by reference.

Libraries of compounds may be presented, e.g., presented in solution (e.g., Houghten (1992) Bio/Techniques 13:412-421), or on beads (Lam (1991) Nature 354:82-84), chips (Fodor (1993) Nature 364:555-556), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865-1869) or phage (Scott and Smith (19900 Science 249:386-390; Devlin (1990) Science 249:404-406; Cwirla et al. (1990) Proc. Natl. Acad. Sci. USA 87:6378-6382; and Felici (1991) J. Mol. Biol. 222:301-310), each of which is incorporated herein in its entirety by reference.

Therapeutic Uses of Agents Identified

The invention provides for treatment of inflammatory and/or autoimmune disorders by administration of a therapeutic agent identified using the above-described methods. Such agents include, but are not limited to proteins, peptides, protein or peptide derivatives or analogs, antibodies, nucleic acids, and small molecules.

The invention provides methods for treating patients afflicted with an inflammatory and/or autoimmune disorder comprising administering to a subject an effective amount of a compound identified by the method of the invention. In a particular aspect, the compound is substantially purified (e.g., substantially free from substances that limit its effect or produce undesired side-effects). The subject is particularly an animal, including but not limited to animals such as cows, pigs, horses, chickens, cats, dogs, etc., and is more particularly a mammal, and most particularly a human. In a specific embodiment, a non-human mammal is the subject.

Formulations and methods of administration that can be employed when the compound comprises a nucleic acid are described above; additional appropriate formulations and routes of administration are described below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu (1987) J. Biol. Chem. 262:4429-4432), and construction of a nucleic acid as part of a retroviral or other vector. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally, e.g., by local infusion during surgery, topical application, e.g., by injection, by means of a catheter, or by means of an implant, said implant being of a porous, non-porous, or gelatinous material, including membranes, such as sialastic membranes, or fibers.

In another embodiment, the compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, e.g., an inflammatory site, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, Science 249:1527-1533).

Pharmaceutical Compositions

The present invention also provides pharmaceutical compositions. Such compositions comprise a therapeutically effective amount of an agent and a pharmaceutically acceptable carrier. In a particular embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, incorporated in its entirety by reference herein. Such compositions will contain a therapeutically effective amount of the compound, preferably in purified form, together with a suitable amount of carrier so as to provide the form for proper administration to the subject. The formulation should suit the mode of administration.

In a particular embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment of an inflammatory or autoimmune disorder (e.g., Crohn's disease) can be determined by standard clinical techniques based on the present description. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Suppositories generally contain active ingredient in the range of 0.5% to 10% by weight; oral formulations preferably contain 10% to 95% active ingredient. Effective doses may be extrapolated from dose-response curves derived from in vitro or animal model test systems.

Nucleic Acids

The invention provides methods of identifying agents capable of modulating human Th-IL17+ cell differentiation. Accordingly, the invention encompasses administration of a nucleic acid encoding a peptide or protein capable of modulating human Th-IL17+ cell differentiation, as well as antisense sequences or catalytic RNAs capable of interfering with human Th-IL17+ cell differentiation.

Any suitable methods for administering a nucleic acid sequence available in the art can be used according to the present invention.

Methods for administering and expressing a nucleic acid sequence are generally known in the area of gene therapy. For general reviews of the methods of gene therapy, see Goldspiel et al. (1993) Clinical Pharmacy 12:488-505; Wu and Wu (1991) Biotherapy 3:87-95; Tolstoshev (1993) Ann. Rev. Pharmacol. Toxicol. 32:573-596; Mulligan (1993) Science 260:926-932; and Morgan and Anderson (1993) Ann. Rev. Biochem. 62:191-217; May (1993) TIBTECH 11(5): 155-215. Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

In a particular aspect, the compound comprises a nucleic acid encoding a peptide or protein capable of modulating human Th-IL17+ cell differentiation, such nucleic acid being part of an expression vector that expresses the peptide or protein in a suitable host. In particular, such a nucleic acid has a promoter operably linked to the coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller and Smithies (1989) Proc. Natl. Acad. Sci. USA 86:8932-8935; Zijlstra et al. (1989) Nature 342: 435-438).

Delivery of the nucleic acid into a subject may be direct, in which case the subject is directly exposed to the nucleic acid or nucleic acid-carrying vector; this approach is known as in vivo gene therapy. Alternatively, delivery of the nucleic acid into the subject may be indirect, in which case cells are first transformed with the nucleic acid in vitro and then transplanted into the subject, known as "ex vivo gene therapy".

In another embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286); by direct injection of naked DNA; by use of microparticle bombardment (e.g., a gene gun; Biolistic, Dupont); by coating with lipids, cell-surface receptors or transfecting agents; by encapsulation in liposomes, microparticles or microcapsules; by administering it in linkage to a peptide which is known to enter the nucleus; or by administering it in linkage to a ligand subject to receptor-mediated endocytosis (see, e.g., Wu and Wu, 1987, J. Biol. Chem. 262:4429-4432), which can be used to target cell types specifically expressing the receptors.

In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al. (1989) Nature 342:435-438).

In a further embodiment, a retroviral vector can be used (see Miller et al. (1993) Meth. Enzymol. 217:581-599). These retroviral vectors have been modified to delete retroviral sequences that are not necessary for packaging of the viral genome and integration into host cell DNA. The nucleic acid encoding a desired polypeptide to be used in gene therapy is cloned into the vector, which facilitates delivery of the gene into a subject. More detail about retroviral vectors can be found in Boesen et al. (1994) Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al. (1994) J. Clin. Invest. 93:644-651; Kiem et al. (1994) Blood 83:1467-1473; Salmons and Gunzberg (1993) Human Gene Therapy 4:129-141; and Grossman and Wilson (1993) Curr. Opin. in Genetics and Devel. 3:110-114.

Adenoviruses may also be used effectively in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993) Current Opinion in Genetics and Development 3:499-503 present a review of adenovirus-based gene therapy. Bout et al. (1994) Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al. (1991) Science 252:431-434; Rosenfeld et al. (1992) Cell 68:143-155; Mastrangeli et al. (1993) J. Clin. Invest. 91:225-234; PCT Publication WO94/12649; and Wang, et al. (1995) Gene Therapy 2:775-783. Adeno-associated virus (AAV) has also been proposed for use in gene therapy (Walsh et al. (1993) Proc. Soc. Exp. Biol. Med. 204:289-300; U.S. Pat. No. 5,436,146).

Another suitable approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr (1993) Meth. Enzymol. 217:599-618; Cohen et al. (1993) Meth. Enzymol. 217:618-644; Cline (1985) Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. In a particular embodiment, epithelial cells are injected, e.g., subcutaneously. In another embodiment, recombinant skin cells may be applied as a skin graft onto the subject; recombinant blood cells (e.g., hematopoietic stem or progenitor cells) are preferably administered intravenously. The amount of cells envisioned for use depends on the desired effect, the condition of the subject, etc., and can be determined by one skilled in the art.

Cells into which a nucleic acid can be introduced for purposes of gene therapy encompass any desired, available cell type, and include but are not limited to neuronal cells, glial cells (e.g., oligodendrocytes or astrocytes), epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood or fetal liver. In a particular embodiment, the cell used for gene therapy is autologous to the subject that is treated.

In another embodiment, the nucleic acid to be introduced for purposes of gene therapy may comprise an inducible promoter operably linked to the coding region, such that expression of the nucleic acid is controllable by adjusting the concentration of an appropriate inducer of transcription.

Direct injection of a DNA coding for a peptide or protein capable of modulating human Th-IL17+ cell differentiation may also be performed according to, for example, the techniques described in U.S. Pat. No. 5,589,466. These techniques involve the injection of "naked DNA", i.e., isolated DNA molecules in the absence of liposomes, cells, or any other material besides a suitable carrier. The injection of DNA encoding a protein and operably linked to a suitable promoter results in the production of the protein in cells near the site of injection.

Homogeneous Populations of Human Th-IL17+ Cells

The novel methods of the present invention facilitate the generation of a homogeneous population of human Th-IL17+ cells comprising about or at least $10^9$ homogeneous human Th-IL17+ cells, wherein the human Th-IL17+ cells do not express cellular markers of other differentiated Th (non-Th-IL17+) cells. More specifically, the isolated homogeneous population of human Th-IL17+ cells generated from naive CD4+ cells do not express cellular markers characteristic of Th1, Th2, or Treg cells. It is understood that cellular markers characteristic of Th1, Th2, or Treg cells would be present in any population of Th-IL17+ cells generated from memory Th cells. Cellular markers characteristic of Th1 cells include, for example, IFN-γ; cellular markers of Th2 cells include, for example, IL4 or IL13; and cellular markers of Treg cells include, for example, FoxP3. Accordingly, a homogeneous population of human Th-IL17+ cells of the present invention does not include cells that express IFN-γ, IL4, IL13 or FoxP3.

The isolated population of about or at least $10^9$ human Th-IL17+ cells generated from naive CD4+ cells as described herein is, therefore, homogeneous with respect to the expression of only those cellular markers characteristic of Th-IL17+ cells. Exemplary markers of human Th-IL17 cells are IL-17, IL-17F, IL-26, and IL23R.

Prior to the present method, an isolated, homogeneous population of about or at least about $10^9$ human Th-IL17+ cells, wherein the human Th-IL17+ cells do not express cellular markers of other differentiated Th (non-Th-IL17+) cells, had not been generated.

It is noteworthy in this regard that Th-IL17+ cells generated from memory T cells are not homogenous because they also contain Th1/Th2/Treg cells, as well as cells expressing various combinations of the cytokines, including Th1/Th17 combinations As used herein and understood in the art, a human T helper type 1 (Th1) cell is a human cell of the CD4 T cell lineage (CD3+CD4+) that expresses at least one marker of differentiation into a Th1 cell, such as IFNγ.

As used herein and understood in the art, a human T helper type 2 (Th2) cell is a human cell of the CD4 T cell lineage (CD3+CD4+) that expresses at least one marker of differentiation into a Th2 cell, such as IL-4 or IL-13.

As used herein and understood in the art, a human T regulatory (Treg) cell is a human cell of the CD4 T cell lineage (CD3+CD4+) that expresses at least one marker of differentiation into a Treg cell, such as FoxP3.

Unless defined otherwise, all technical and scientific terms used herein have the same meaning as commonly understood by one of ordinary skill in the art to which this invention belongs.

It is to be understood that this invention is not limited to particular assay methods, or test agents and experimental conditions described, as such methods and agents may vary. It is also to be understood that the terminology used herein is for the purpose of describing particular embodiments only, and is not intended to be limiting, since the scope of the present invention will be limited only the appended claims.

EXAMPLE I

To avoid having antigen-experienced cells and serum-derived TGF-β in the Th17 differentiation cultures, the present inventors used human cord blood CD4$^+$ T cells and serum-free medium. Under these conditions, induction of IL-17 and other Th17 gene products was observed only if TGF-β was added to the culture medium. In contrast to requirements in mouse T cell cultures, human Th17 cell differentiation was not observed when IL-6 or IL-21 was combined with TGF-β. Instead, IL-1β and any one of IL-6, IL-21 or IL-23 were required in combination with TGF-β for induction of IL-17 expression. As in mouse, RORγT was induced by TGF-β and was required and sufficient for expression of Th17 cell products, suggesting that the basic mechanism of Th17 cell differentiation is evolutionarily conserved.

In accordance with the novel and surprising results presented herein, the present inventors have developed a new method for promoting differentiation and proliferation of human T helper lymphocytes that express IL17 (Th-IL17+ cells) in vitro. The instant method is also well suited to screening methods whereby modulators (inhibitors or promoters/inducers) of human Th-IL17+ cell differentiation are identified. The present method is also useful for generating homogeneous populations of human Th-IL17+ cells.

Material and Methods

Cell Purification

Blood samples were obtained from the New York Blood Center. Mononuclear cells were prepared from buffy coats of healthy adult donors or from cord blood on FicollPAQUE gradients. CD4$^+$ T cells were isolated on an autoMACS Pro using Miltenyi bead depletion of CD14$^+$ and CD25$^+$ cells followed by positive selection of CD4$^+$ cells. Cord blood CD4+ T cells were >97% pure and 100% CD45RA+ and were used as such for initial transduction experiments. Adult CD4+ T cell subsets and naive cord blood CD4+ T cells were further purified respectively as CD3+CD4+CD25−CD45RO−/+ and CD3+CD4+CD25−HLA-DR−CD45RA+ by cell sorting on a FACSAria.

Cell Culture and Lentiviral Transduction

Cells were cultivated in either RPMI1640 (Invitrogen) supplemented with 10% fetal bovine serum (Hyclone), penicillin-streptomycin, 2 mM glutamine, 10 mM HEPES, 1 mM pyruvate and 0.1 mM non-essential amino acids or serum-free XVIVO-20 (Lonza) supplemented with penicillin-streptomycin in a 37° C. 5% $CO_2$ incubator. CD4+ T cells were stimulated by addition of anti-mouse IgG magnetic beads (Pierce) previously coated with purified anti-CD3 and anti-CD28 at final concentrations of 1 bead/cell and 1 µg/ml of each antibody. For transduction experiments, cells were seeded at a concentration of $10^6$ cells/ml in 24 well plates with anti-CD3/CD28 coated beads, 10 µg/ml polybrene and 10 U/ml IL-2 at day 0. Lentiviral supernatants were added at an MOI ranging from 1 to 10. Cells were washed at day 1 and split as needed in the presence of IL-2. For the shRNA experiment, puromycin was added at day 2 at 2 µg/ml. For polarization experiments, cells were seeded at a concentration of $5 \times 10^5$ to $10^6$ cells/ml in U-bottom 96 well plates with anti-CD3/CD28 coated beads. IL-2 at 10 U/ml was either added at day 0 or day 3. Media was replaced at day 3 and cells were split in the presence of IL-2. For long-term experiments, cells were split as needed. In some cases, 10 ng/ml IL-1β (eBioscience), 10 ng/ml IL-6 (eBioscience), 10 ng/ml IL-21 (Cell Sciences), 10 ng/ml IL-23 (eBioscience), various concentrations of TGF-β1 (PeproTech), neutralizing soluble IL-21R (R&D) and neutralizing antibodies against IL-2, IL-4, IL-6, IFNγ or TGF-β (1 µg/ml except noted otherwise; see Table 1 for details) were added at day 0 and maintained throughout the experiment. Cells were harvested at day 6 for intracellular staining and real-time PCR analysis except where specified otherwise.

TABLE 1

Antibodies used.

| Antigen | Clone/Catalog number | Company |
|---|---|---|
| CCR6-FITC | FAB196F | R&D |
| CCR6-biotin | 11A9 | BD |
| CD3-Alexa750Cy7 | UCHT1 | eBioscience |
| CD4-PacBlue | OKT4 | eBioscience |
| CD25-APC | 555434 | BD |
| CD45RA-PE | HI100 | eBioscience |
| CD45RO-APC | UCHL1 | eBioscience |
| IL-17-APC | eBio64CAP17 | eBioscience |
| IL-17-FITC | eBio64DEC17 | eBioscience |
| IL-22-PE | IC7621P | R&D |
| IFNγ-PECy7 | 45.B3 | eBioscience |
| HLA-DR-FITC | 555558 | BD |
| HSA-PE (mCD24) | 553262 | eBioscience |
| CD3 purified | UCHT1 | eBioscience |
| CD28 purified | CD28.2 | eBioscience |
| TGF-β purified | 1D11 | R&D |
| IL-2 purified | 5334.21 | R&D |
| IL-4 purified | MP425D2 | eBioscience |
| IL-6 purified | MQ2-13A5 | eBioscience |
| IFNγ purified | NIB42 | eBioscience |

Surface and Intracellular Staining

For intracellular cytokine staining, cells were incubated for 5 hours with 50 ng/ml PMA (Sigma), 500 ng/ml Ionomycin (Sigma), and GolgiStop (BD). Surface staining was performed by incubation with the corresponding fluorescently labeled antibodies for 15 min on ice. Intracellular staining was performed using the Cytofix/Cytoperm buffer set (BD). Briefly, cells were fixed and permeabilized for 30 min at room temperature and stained in permeabilization buffer for 30 min at room temperature. Flow cytometric measures were performed on a LSR II (BD Biosciences) instrument and analyzed using FlowJo software (Tree Star Inc.). Antibodies are detailed in Table 1. FOXP3 was stained using FOXP3 staining buffers (eBioscience). The present inventors used the FJK-16s antibody, which was originally reported as an anti-mouse/rat FoxP3 antibody. Indeed, the present inventors have observed that, unlike most anti-human FOXP3 antibodies available, this antibody robustly stains endogenous and over-expressed human full-length FOXP3.

Plasmids and Lentiviral Production

Human RORγT was cloned from human thymus. A double FLAG tag (DFTC) was added at the N-terminus. Human RORα isoform d was cloned from peripheral CD4+ T cells. Human RORβ was cloned from U937 cells. cDNAs were cloned in an HIV-derived vector HDV-IRES-HSA or HDV-IRES-GFP[65]. Human GATA-3 and T-bet lentiviral vectors have been previously described[57]. shRNA vectors were obtained from OpenBiosystem. shRNA-1 is TRCN33657 (target sequence TCTGCAAGACTCATCGCCAAA; SEQ ID NO: 1) and shRNA-2 is TRCN33658 (target sequence CGAGGATGAGATTGCCCTCTA; SEQ ID NO: 2), and pLKO.1puro was used as control. Viral supernatants were produced by transient transfection of 293T cells with vector DNA, a VSV-G expression plasmid and the pCMVΔR8.9 GagPol expression vectors for the shRNA vectors. Viral particles were concentrated by ultracentrifugation at 25,000 rpm for 2 h at 4° C., resuspended in PBS containing 1% BSA, aliquoted and frozen.

Real-Time PCR

RNA was extracted by TRIZOL (Invitrogen) and cDNA was synthesized with Superscript II (Invitrogen) and random primers. cDNA was analyzed by real-time quantitative PCR in triplicates by using iQ CYBR Green Supermix (Bio-Rad) or QuantiTect Multiplex PCR mix (Qiagen) in the iCycler Sequence Detection System (Bio-Rad). The starting quantity (SQ) of the initial cDNA sample was calculated from primer-specific standard curves by using the iCycler Data Analysis Software. The expression level of each gene was normalized to beta-actin expression level using the standard curve method. Fold changes were calculated by normalizing to the first sample of each set. Error bars were calculated based on triplicate measurements of each gene. The primer sets for real-time PCR are detailed in Table 2.

TABLE 2

Primers used.

| Gene | Orientation | Sequence |
|---|---|---|
| ACTB | F | GGACTTCGAGCAAGAGATGG; SEQ ID NO: 3 |
| ACTB | R | AGCACTGTGTTGGCGTACAG; SEQ ID NO: 4 |
| ACTB | Probe | CTCTTCCAGCCTTCCTTCCT; SEQ ID NO: 5 |
| RORA | F | CGGTGCCTTTGACTCTCAGAACAACACCG; SEQ ID NO: 6 |
| RORA | R | TCTTTCCAAATTCAAACACAAAGC; SEQ ID NO: 7 |

TABLE 2-continued

Primers used.

| Gene | Orientation | Sequence |
|---|---|---|
| RORA | Probe | TTGATGGGAAGTATGCCAGC; SEQ ID NO: 8 |
| RORC | F | TTTTCCGAGGATGAGATTGC; SEQ ID NO: 9 |
| RORC | R | CTTTCCACATGCTGGCTACA; SEQ ID NO: 10 |
| RORC | Probe | AAGACTCATCGCCAAAGCAT; SEQ ID NO: 11 |
| IL23R | F | CATGACTTGCACCTGGAATG; SEQ ID NO: 12 |
| IL23R | R | GCTTGGACCCAAACCAAGTA; SEQ ID NO: 13 |
| IL23R | Probe | TGATTCATTACAAGGTGGCAA; SEQ ID NO: 14 |
| IL17F | F | TGAAGCTTGACATTGGCATC; SEQ ID NO: 15 |
| IL17F | R | TTCCTTGAGCATTGATGCAG; SEQ ID NO: 16 |
| IL17F | Probe | ACCTCCCCCTGGAATTACAC; SEQ ID NO: 17 |
| IL17 | F | ACCAATCCCAAAAGGTCCTC; SEQ ID NO: 18 |
| IL17 | R | GGGGACAGAGTTCATGTGGT; SEQ ID NO: 19 |
| IL17 | Probe | GCAATGAGGACCCTGAGAGA; SEQ ID NO: 20 |
| IL26 | F | TGCAAGGCTGCAAGAAAATA; SEQ ID NO: 21 |
| IL26 | R | CCAGTTCACTGATGGCTTTG; SEQ ID NO: 22 |
| IL26 | Probe | GGCAGAAATTGAGCCACTGT; SEQ ID NO: 23 |
| IL6 | F | AAAGAGGCACTGGCAGAAAA; SEQ ID NO: 24 |
| IL6 | R | TTTCACCAGGCAAGTCTCCT; SEQ ID NO: 25 |
| IL21 | F | TTCTGCCAGCTCCAGAAGAT; SEQ ID NO: 26 |
| IL21 | R | TTGTGGAAGGTGGTTTCCTC; SEQ ID NO: 27 |
| IL21 | Probe | TGGTCAGCTTTTTCCTGCTT; SEQ ID NO: 28 |

Results

RORγt-Dependent IL-17 Expression in Human Memory CD4+ T Cells

Figure 1:
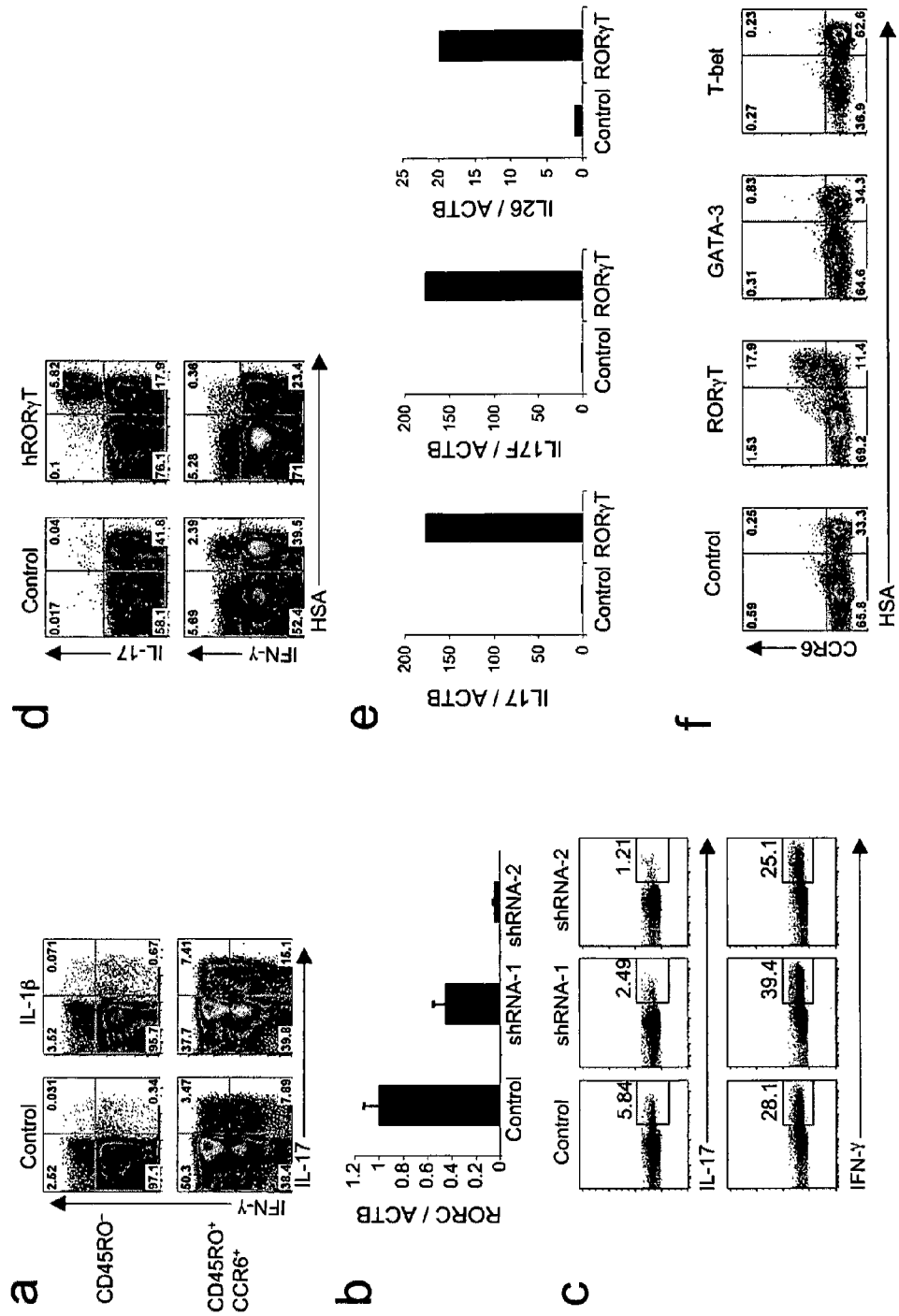
FIG. 1a-f. RORγT is necessary and sufficient for the expression of IL-17 in human CD4+ T cells. (a) Sorted CD45RO− and CD45RO+CCR6+ were activated and expanded in the presence of IL-2 with or without IL-1β. IL-17 and IFNγ production was analyzed at day 6. (b, c) Sorted CD45RO+CCR6+ were transduced with an empty vector or vector encoding RORγT-specific shRNA (shRNA-1 and shRNA-2). Cells were selected in puromycin at day 2. RORC and β-actin mRNA expression (b) and IL-17 and IFNγ production (c) were analyzed at day 6 (representative experiment, n=4). (d) Naive cord blood CD4+ T cells were activated, transduced by vectors encoding IRES-HSA or RORγT-IRES-HSA and expanded for 6 days in the presence of IL-2. IL-17 and IFNγ production was analyzed at day 6. (e) Naive cord blood CD4+ T cells were transduced with vectors encoding IRES-GFP or RORγT-IRES-GFP. GFP+ cells were sorted at day 6 and mRNA levels of β-actin, IL-17, IL-17F and IL-26 were analyzed. (f) Naive cord blood CD4+ T cells were transduced with vectors encoding IRES-HSA, RORγT-IRES-HSA, GATA-3-IRES-HSA or T-bet-IRES-HSA. CCR6 cell surface expression was measured at day 12.

To evaluate the effect of IL-1β on IL-17 production, the present inventors sorted naive CD45RO−CD25−CCR7+ and Th17-containing memory CD45RO+CD25−CCR6+ CD4+ T cells from adult peripheral blood and cultured them in serum-containing media in the presence or absence of IL-1β. IL-1β induced a two-fold increase of IL-17 production in CCR6+ memory cells, but had no effect on CD45RO− cells (FIG. 1a). Similar results were observed with CD45RA+ sorted cells. With the goal of identifying requirements for Th17 cell differentiation in humans, the present inventors initially wished to evaluate whether RORγT was necessary in pre-committed Th17 cells to maintain effector function. To ablate RORγT expression, two shRNAs that demonstrated potent knockdown of RORγT by transient transfection were utilized. Sorted CD45RO+CCR6+ memory CD4+ T cells isolated from adult blood were transduced with the shRNA vectors. After 6 days, shRNA-1 and shRNA-2 reduced RORγT expression by 50% and 90%, respectively (FIG. 1b). Correspondingly, the present inventors observed on average 2-fold and 3.2-fold decreases in IL-17+ cells with shRNA-1 and shRNA-2, respectively (FIG. 1c). The proportion of IFNγ+ cells remained high in all samples. Thus, RORγT is required for maintenance of IL-17 expression in differentiated T cells.

RORγT Induces Expression of IL-17, IL-17F, IL-26 and CCR6 in Human Naive Cord Blood CD4+ T Cells.

Figure 6:
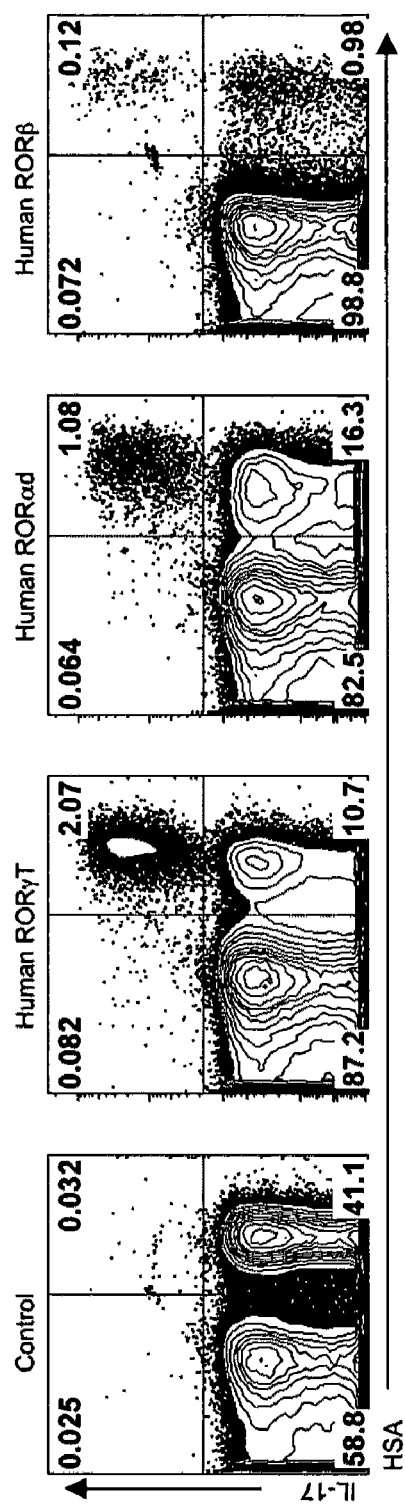
FIG. 6: IL-17 expression following RORγT, RORαd and RORβ transduction. Naive cord blood CD4+ T cells were transduced with RORγT, RORαd and RORβ in RPMI-10% FBS alone. IL-17 was analyzed at day 6.

The present inventors next asked whether overexpression of RORγT, that would bypass any requirement of its induction by cytokines, would be sufficient to obtain IL-17 expression in naive CD4+ human T cells. CD4+ T cells were isolated from human cord blood to ensure a naive phenotype, activated with anti-CD3 and anti-CD28, and transduced with control or human RORγT-encoding lentivirus. IL-17 expression was readily detected, peaking at 6 days in cells transduced with the RORγT vector (FIG. 1d). The proportion of interferon-γ-expressing cells was substantially reduced by the expression of RORγT (FIG. 1d). RORαd and RORβ, two other ROR-family members, also induced IL-17 expression when overexpressed in primary human T cells (FIG. 6).

Figure 7:
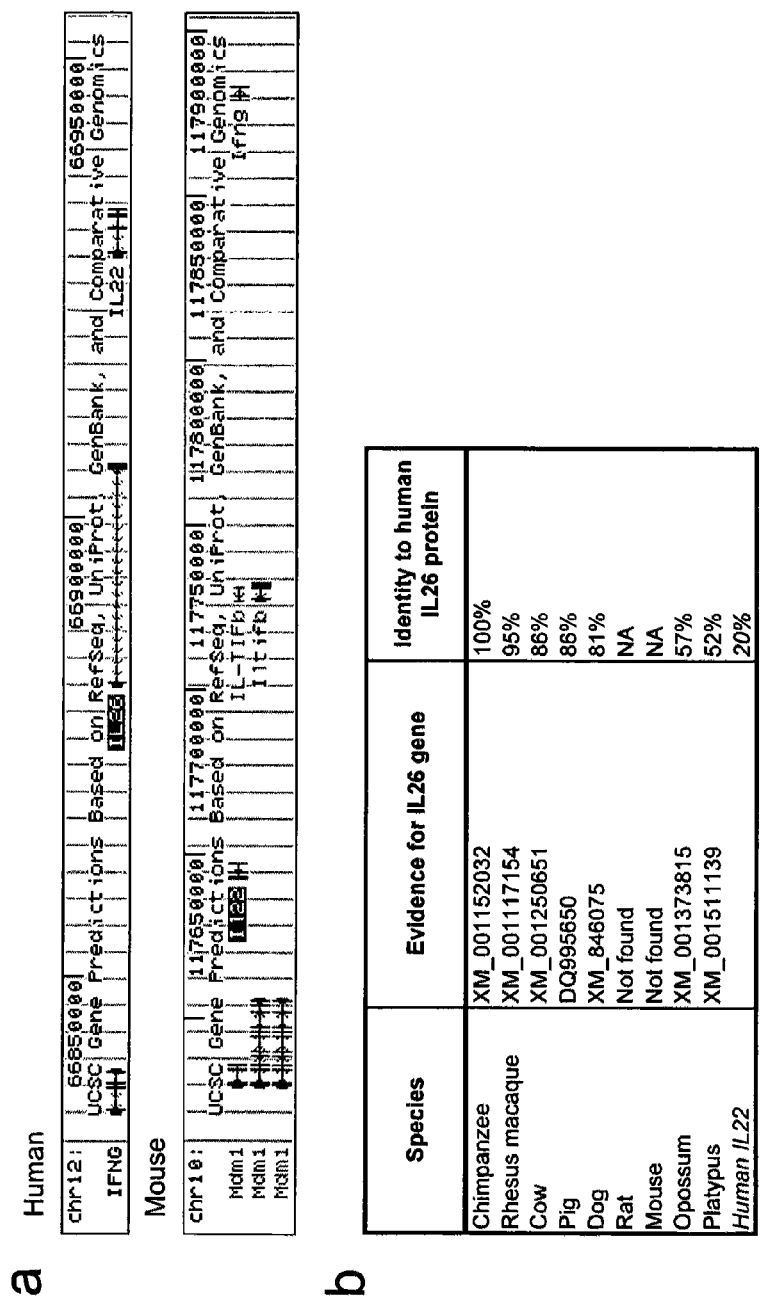
FIG. 7a-b: IL26 gene has been lost in mice and rats. (a) Genomic organization of the IL22 locus based on UCSC genome browser. In humans, IL22 is followed by IL26 and IFNG in the same locus. In the mouse, Il22 is followed by Iltifb (a duplication of Il22) and Ifng, and Il26 is absent. (b) Among species, IL26 can be detected in pre-placental vertebrates, but cannot be found in the mouse or rat genome.

The present inventors did not detect IL-22 protein induction with RORγT overexpression. This was unexpected because IL-22 mRNA is strongly up-regulated by Rorγt in murine CD4+ T cells (L. Zhou et al., unpublished observations). This apparent discrepancy between mouse and human led us to investigate the IL22 gene of various species (FIG. 7a). In human, the IL22 gene is located in the same locus as IFNG and IL26. In mouse, there is no IL26 gene, and Il22 is located in the same locus as Ifng and Iltifb, an Il22 duplication. IL-26, similarly to IL-22, is an IL-10 related cytokine and is found in memory CD4+ T cells expressing IL-17[15]. Quantitative PCR analysis of RORγT-expressing cells indicated that IL-26 is induced along with IL-17 and IL-17F by RORγT (FIG. 1e). The IL26 gene was also found in the genome of pre-placental vertebrates, including zebrafish[35], but not in the genome of rat and mouse (FIG. 7b), suggesting that it was lost in a common ancestor for both rodents.

Human Th17 cells are exclusively found in the CD45RO+ CCR6+ compartment in adult blood. However, this compartment also contains IFNγ+IL-17− and IFNγ+IL-17+ cells. In order to determine which transcription factor could induce CCR6 expression in CD4+ T cells, the present inventors transduced cord blood CD4+ T cells with vectors encoding RORγT or the transcription factors involved in specification of the Th1 and Th2 cell lineages, T-bet and GATA-3, respectively, as well as a control empty vector. CCR6 was induced in RORγT-expressing cells, but not in cells transduced with GATA-3 or T-bet, and it was not induced in trans in cultures of RORγT expressing cells (FIG. 1f). Expression of CCR2 and CCR4, also suggested to be Th17 cell markers[4, 36], was not altered by overexpression of RORγT.

Antagonistic Effects of TGF-β on RORγT Function

Figure 2:
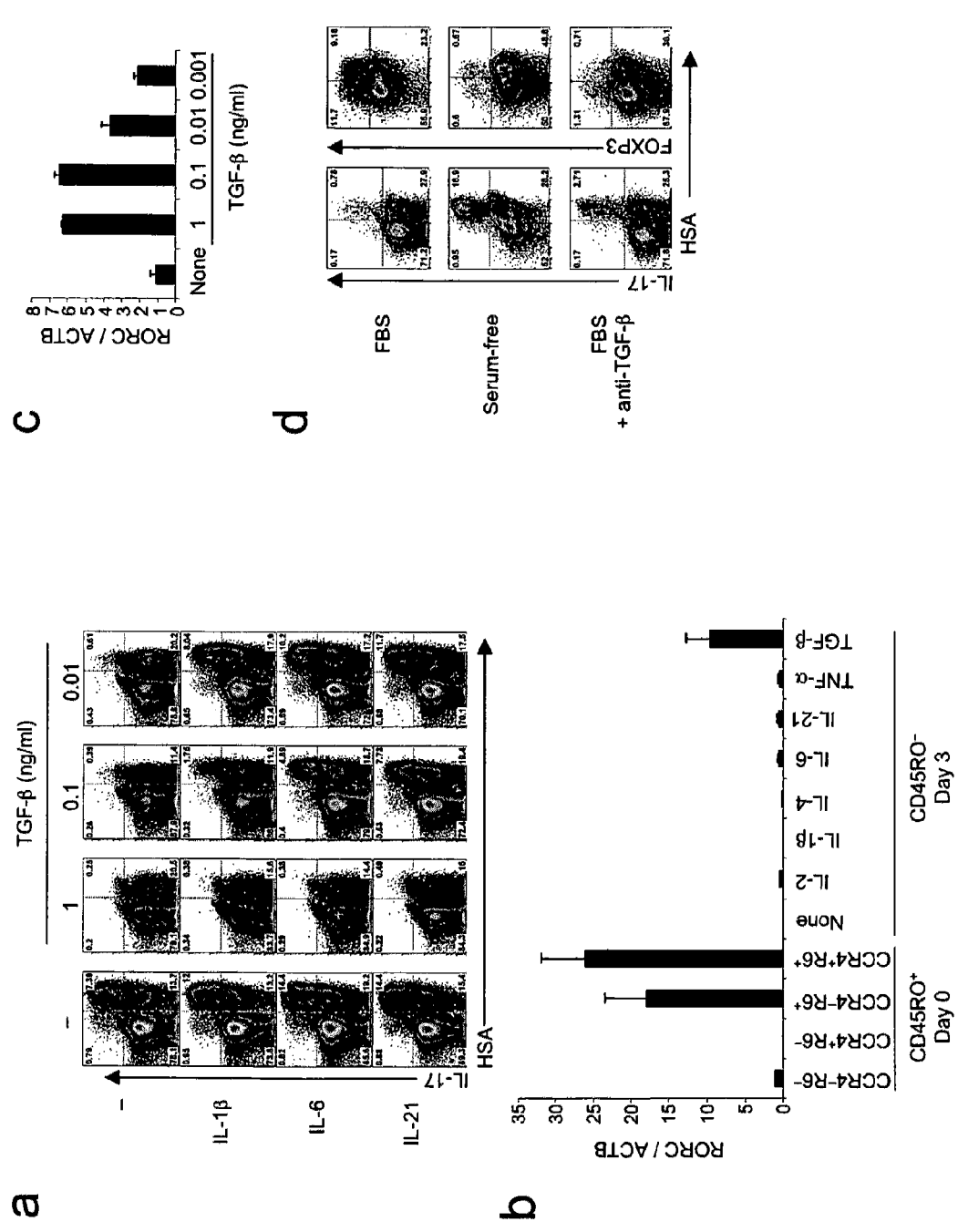
FIG. 2a-d: TGF-β induces RORγT but inhibits its activity and this inhibition is relieved by inflammatory cytokines. (a) Naive cord blood CD4+ T cells were transduced with a vector encoding RORγT-IRES-HSA alone or with a combination of IL-1β, IL-6, IL-21 and increasing concentrations of TGF-β, and IL-17 intracellular staining was performed at day 6. (b) RORC and β-actin expression was measured in freshly sorted CCR4−/+CCR6−/+ adult memory CD4+ T cells and in naive CD4+ T cells cultivated for 3 days in the presence of various cytokines. (c) RORC and β-actin expression was analyzed in naive cord blood CD4+ T cells that were cultivated in various concentrations of TGF-β. (d) Naive cord blood CD4+ T cells were transduced with a vector encoding RORγT-IRES-HSA in either RPMI-10% FBS, RPMI-10% with an anti-TGF-β antibody or serum-free media. IL-17 and FOXP3 expression were analyzed at day 6. A representative donor with low IL-17 expression following RORγT transduction in the presence of serum is shown.

The present inventors next sought to determine how cytokines known to affect Th17 cells in mouse or human would affect IL-17 expression following RORγT overexpression, circumventing the potential effect of those cytokines on RORγT expression per se. Cord blood CD4+ T cells were transduced with RORγT alone or in the presence of IL-1β, IL-6, or IL-21 in combination with various concentrations of TGF-β (FIG. 2a). Addition of IL-1β, IL-6 and IL-21 increased by about two-fold the proportion of IL-17-producing cells obtained after forced expression of RORγT. However, TGF-β potently suppressed IL-17 production. Interestingly, addition of any one of IL-1β, IL-6 or IL-21 partially relieved the suppression induced by TGF-β. The present inventors then invested whether these cytokines could influence expression of endogenous RORγT. CD45RO− naive, as well as subsets of memory CD4+ T cells, were sorted from adult peripheral blood based on CCR6 and CCR4 expression for comparison of RORγT mRNA levels. RORγT expression was enriched in CCR6+ cells. Various cytokines were screened for their ability to induce the expression of RORC, the gene encoding for RORγT, in CD45RO⁻ adult naive CD4⁺ T cells. Surprisingly, addition of TGF-β alone induced dose-dependent RORγT expression, but none of the other cytokines had such an effect (FIGS. 2b and 2c). However, treatment with TGF-β alone or with IL-1β, IL-6 or IL-21, was insufficient to induce significant IL-17 expression as detected by intracellular staining under these conditions.

The observation that cultures containing IL-1β, IL-6 and IL-21 had increased IL-17 expression following RORγT transduction (FIG. 2a) suggested that an endogenous source of TGF-β existed in our culture conditions, and that addition of the other cytokines relieved its effect in a similar manner to their effect following addition of exogenous TGF-β. Indeed TGF-β is found in human and bovine serum[37, 38]. Furthermore, serum TGF-β was found to be sufficient to induce FOXP3 expression in naive human CD4⁺ T cells[39]. The present inventors thus asked whether IL-17 expression was increased in serum-free conditions. Cord blood CD4⁺ T cells were transduced with RORγT in RPMI-10% FBS and serum-free media. A significant increase in IL-17 production was observed in serum-free media, which was most pronounced for donors that exhibit the lowest expression of IL-17 following RORγT transduction in the presence of serum (FIG. 2d). Concurrently, FOXP3 expression was induced in RPMI-10% FBS, but not in serum-free media. Following addition of a neutralizing anti-TGF-β antibody in RPMI-10% FBS, FOXP3 induction was almost abolished, while IL-17 expression was increased, but not to the extent observed in serum-free media. Higher concentration of neutralizing antibody did not improve IL-17 expression (FIG. 8).

These observations indicated that TGF-β present in serum inhibits to some extent IL-17 expression induced by RORγT and that other unidentified compounds contained in fetal bovine serum possibly also counteract Th17 cell differentiation. These findings prompted the present inventors to evaluate whether TGF-β, IL-1β, IL-6 and IL-21 would induce IL-17 production in serum-free media.

Figure 3:
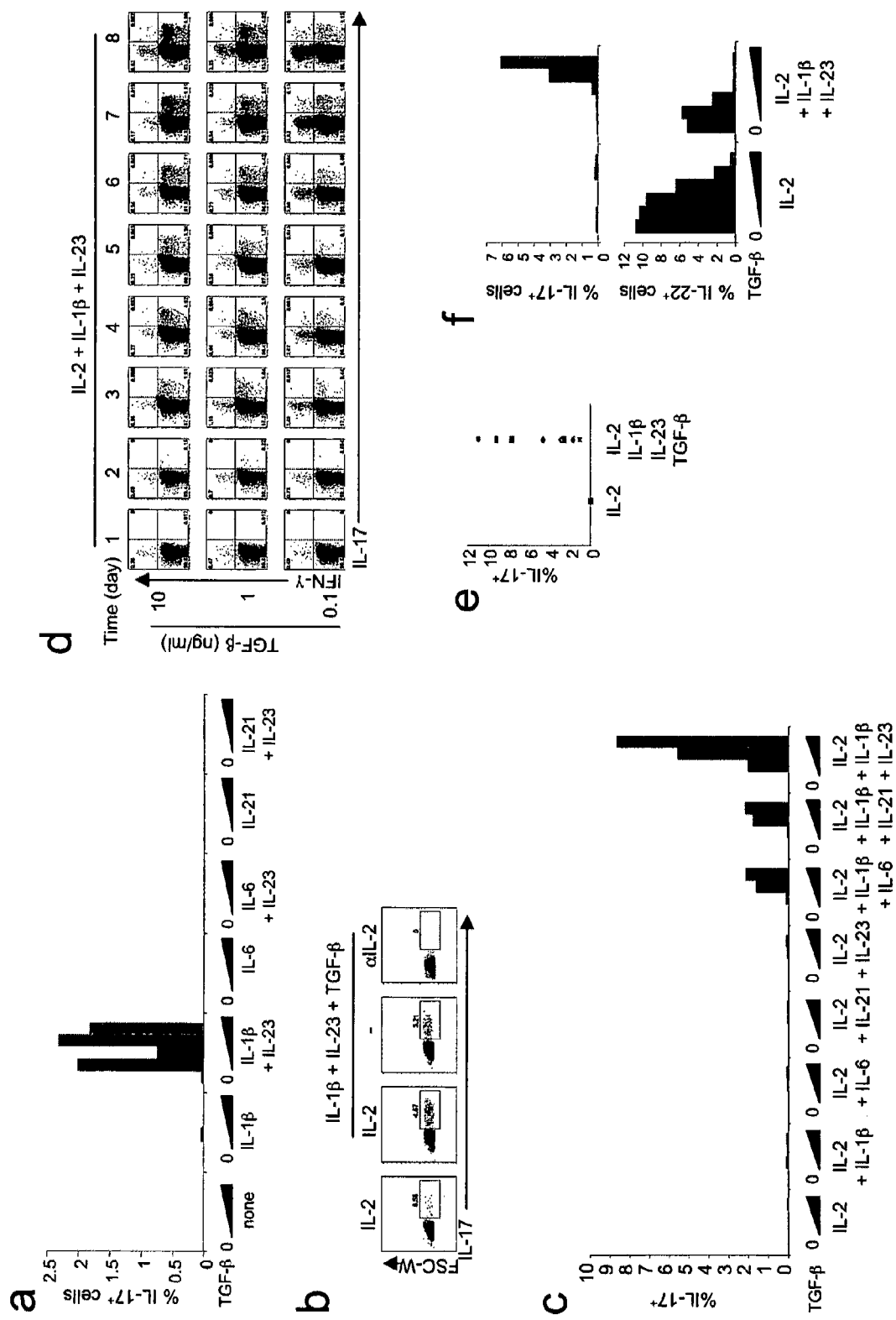
FIG. 3a-f. TGF-β, IL-1β and either IL-6, IL-21 or IL-23 are required for human Th17 cell polarization in serum free conditions. (a) Naive cord blood CD4+ T cells were activated without cytokines or with IL-1β, IL-6 or IL-21 with or without IL-23, alone or with increasing concentrations of TGF-β. IL-2 was added at day 3 and IL-17 expression was analyzed at day 14. (b) Naive cord blood CD4+ T cells were activated with no cytokine or with a combination of IL-1β+IL-23+TGF-β (1 ng/ml), with or without 10 U/ml IL-2. IL-17 expression was analyzed at day 6. (c) Naive cord blood CD4+ T cells were cultivated with IL-23+IL-2 alone or together with IL-1β, IL-21 or IL-23 and increasing concentrations of TGF-β. IL-17 and IFNγ expression was analyzed at day 6. (d) Time-course of IL-17 and IFNγ production in naive cord blood CD4+ T cells polarized in the presence of IL-2+IL-1β+IL-23+TGF-β (0.1, 1 or 10 ng/ml). (e) Summary of IL-17 expression in day 6 cultures of naive cord blood CD4+ T cells from different donors (n=11) in the presence of IL-2+IL-1β+IL-23+10 ng/ml TGF-β. (f) Naive cord blood CD4+ T cells were cultivated in IL-2 alone or IL-23+IL-1β+IL-2 with increasing concentrations of TGF-β. IL-17 and IL-22 expression was analyzed at day 6. Each panel is representative of at least three independent donors.

TGF-β, IL-1β and Either IL-6, IL-23 or IL-21 are Required for Human Th17 Cell Polarization in Serum-Free Media Naive cord blood CD4⁺ T cells were activated with anti-CD3/CD28 beads in serum-free media in the presence of anti-IL-4 and anti-IFNγ alone or with various combinations of cytokines. These combinations included increasing concentrations of TGF-β with no added cytokine or with IL-1β, IL-6 or IL-21, with or without IL-23 (FIG. 3a). After two weeks of culture, IL-17 expression could be detected by intracellular staining only in cells cultivated with a combination of TGF-β, IL-1β and IL-23. Although IL-2 was found to inhibit IL-17 expression in mice[40], IL-1β relieved this effect[41]. The effect of IL-2 and neutralizing anti-IL-2 antibody was then tested in the above-indicated culture conditions. In the presence of TGF-β, IL-1β and IL-23, IL-17 expression was increased at day 6 when IL-2 was included (FIG. 3b). Addition of an anti-IL-2 blocking antibody prevented cell proliferation and IL-17 expression could not be detected. Thus IL-2 appears to have a positive effect on IL-17 expression in human CD4⁺ T cell culture. In the mouse, IL-23, IL-21 and IL-6 share the ability to activate STAT3 if their cognate receptors are expressed. Although IL-6 and IL-21 failed to induce IL-17 in human cord blood T cells when combined with TGF-β alone, they were active, albeit not as strongly as IL-23, when both IL-1β and TGF-β were included (FIG. 3c). IL-21 is synthesized in response to IL-6 by Th17 cells in the mouse and acts in an autocrine manner to induce Th17 cell differentiation[25-27]. The present inventors subsequently evaluated if IL-21 and/or IL-6 were required for human IL-17 induction, as they are in mouse. In human cells, IL-6 and IL-21 expression was not induced by IL-1β+IL-23+TGF-β (FIGS. 9a and 9b). Furthermore, addition of neutralizing anti-IL-6 antibody or soluble IL-21R had no effect on IL-17 expression at levels that inhibited STAT3 phosphorylation (FIG. 9c). Thus, in contrast to observations with naive mouse CD4⁺ T cells, IL-23 can participate in induction of IL-17 in human T cells in the absence of IL-6 and IL-21.

TGF-β, IL-1β and IL-23 Induce the Expression of IL-17, IL-17F, IL-26, IL-23R, CCR6 and RORγT and Inhibit the Expression of FOXP3

In light of the above findings, the present inventors adopted a combination of cytokines containing TGF-β, IL-1β, IL-23, and IL-2 for Th17 cell polarization of human cord blood naive CD4⁺ T cells. IL-17⁺ cells were clearly detected as early as day 3 and increased up to day 6 in culture (FIG. 3d). Across multiple cord blood samples, the proportion of IL-17⁺ cells obtained under these conditions ranged from 0.5% to 11% (FIG. 3e). As in the mouse[42], IL-17 induction was inhibited by addition of retinoic acid (FIG. 10). The present inventors also evaluated IL-22 levels in Th17 cell differentiation cultures comprising cord blood cells. A substantial proportion of naive cord blood CD4⁺ T cells spontaneously expressed IL-22 protein after 6 days of culture (FIG. 3f). As the concentration of TGF-β was increased, IL-22 expression was progressively inhibited.

Figure 4:
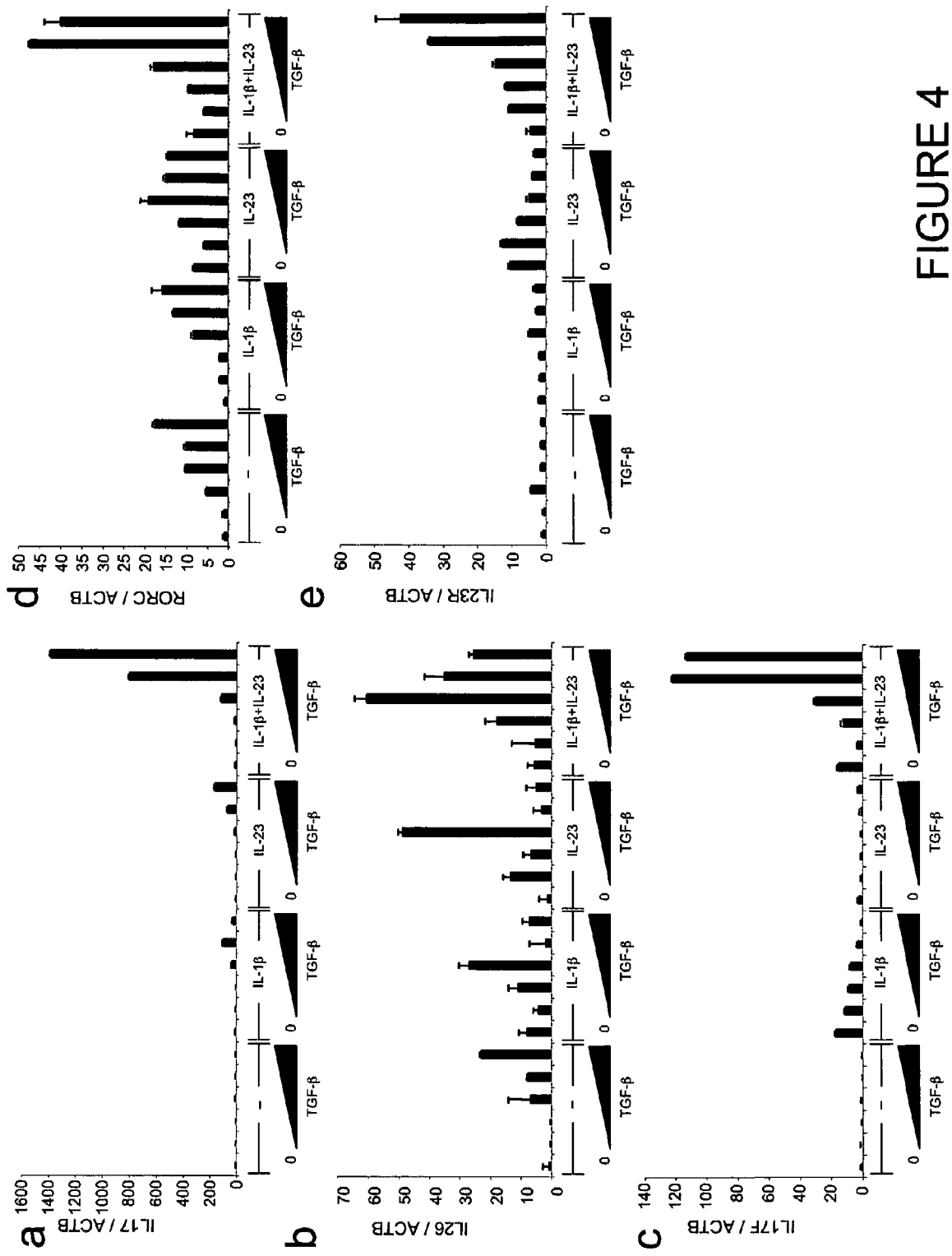
FIG. 4a-e: Induction of IL26, IL17F, IL17A, RORC and IL23R mRNA during human Th17 cell differentiation. (a, b, c) Naive cord blood CD4+ T cells were cultivated with IL-2 alone or with IL-1β+IL-2, IL-23+IL-2, or IL-23+IL-1β+IL-2 with increasing concentrations of TGF-β. mRNA levels of β-actin, IL17 (a), IL26 (b) and IL17F (c) were analyzed on day 6 following restimulation with PMA and ionomycin. (d, e) Naive cord blood CD4+ T cells were cultivated with IL-2 alone or with IL-1β+IL-2, IL-23+IL-2 or IL-23+IL-1β+IL-2 with increasing concentrations of TGF-β. mRNA levels of β-actin, RORC (d) and IL23R (e) were analyzed on day 6. Each panel is representative of three independent donors.
Figure 5:
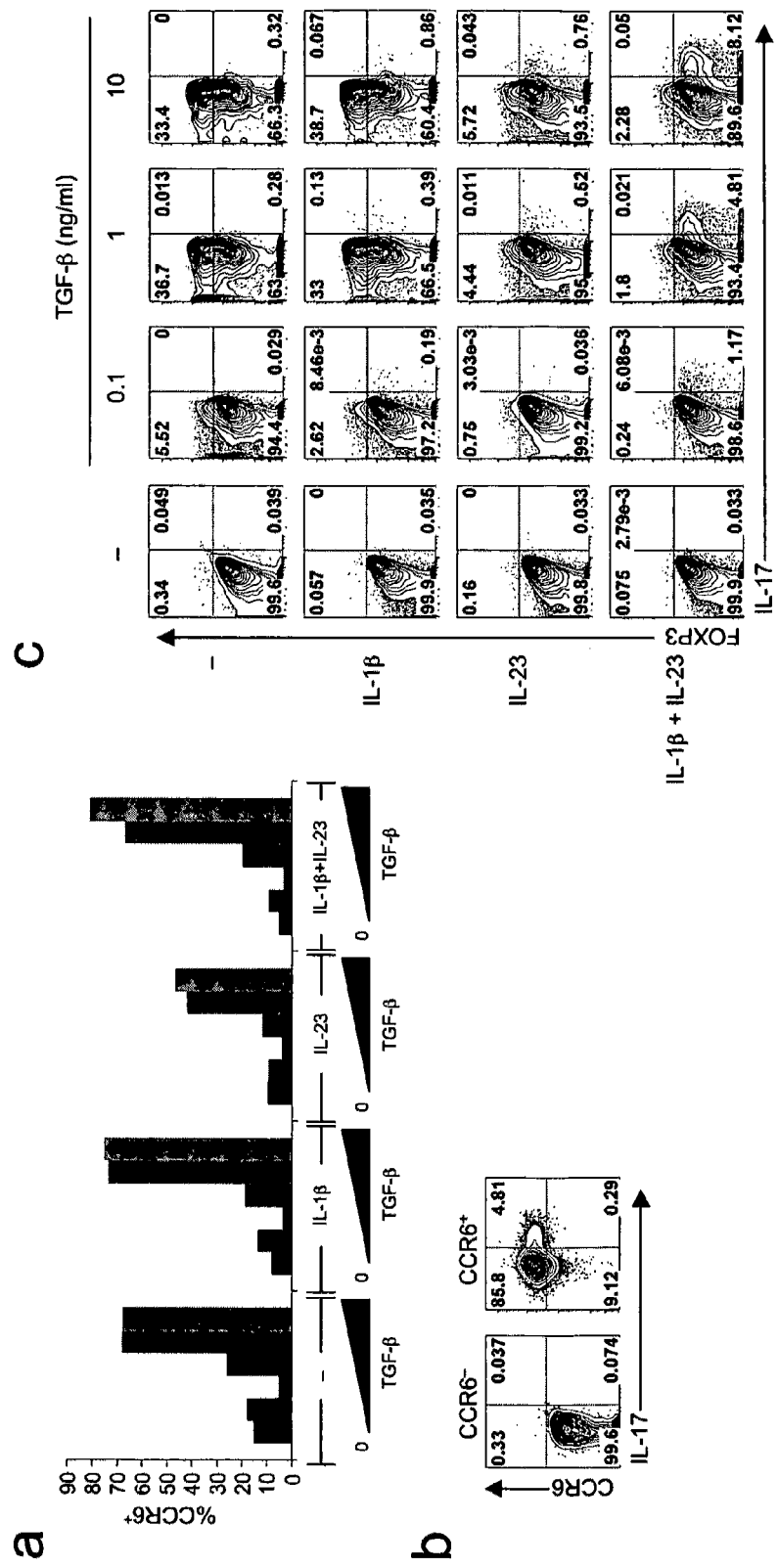
FIG. 5a-c: Expression of CCR6 and FOXP3 during human Th17 cell differentiation. (a) Naive cord blood CD4+ T cells were cultivated with IL-2 alone or with IL-1β+IL-2, IL-23+IL-2, or IL-23+IL-1β+IL-2 with increasing concentrations of TGF-β. CCR6 expression was analyzed by surface staining at day 6. (b) Naive cord blood CD4+ T cells were cultivated for 6 days in IL-2+IL-23+IL-1β+IL-2+10 ng/ml TGF-β. CCR6+ and CCR6− cells were sorted and IL-17 was analyzed. (c) Naive cord blood CD4+ T cells were cultivated with IL-2 alone or with IL-1β+IL-2, IL-23+IL-2, or IL-23+IL-1β+IL-2 with increasing concentrations of TGF-β. FOXP3 and IL-17 expression were analyzed at day 6.

Since it was observed that RORγT induces expression of IL-26, the present inventors asked whether IL-26 could similarly be induced in human cord blood cells cultured under Th17 cell differentiation conditions. When naive CD4⁺ T cells were stimulated in the presence of IL-2 in serum free medium, IL-17 mRNA expression detected by real-time PCR at day 6 was maximal following induction by the combination IL-1β, IL-23, and TGF-β, consistent with the intracellular staining (FIG. 4a). IL-26 expression was also detected and levels of IL-26 mRNA increased with the dose of TGF-β (FIG. 4b). Some expression of IL-17F was induced by IL-1β alone and IL-23 alone had no effect (FIG. 4c). However, in the presence of IL-23 and IL-1β increasing concentrations of TGF-β synergized to induce maximum IL-17F expression. RORC expression was gradually induced with increasing concentrations of TGF-β and was enhanced by further addition of both IL-1β+IL-23, but not either cytokine alone. In the same conditions, RORA expression was slightly induced by TGF-β and there was no further effect upon addition of IL-1β and IL-23 (FIG. 11a). This observation is in agreement with the slight enrichment of RORA mRNA levels in memory CCR6⁺ cells compared to CCR6⁻ cells (FIG. 11b). In mice, IL-23R is induced by IL-6 or IL-21 but inhibited by high concentrations of TGFβ[43]. In human cells, IL-23R expression was induced to some extent by IL-23 alone, but not IL-1β, consistent with another report[28] (FIG. 4e). However, IL-23R expression reached maximal levels in the presence of IL-1β and IL-23 with increasing concentrations of TGF-β. This suggests that in the presence of TGF-β and IL-1β, IL-23 induces expression of its own receptor through a positive feedback loop, leading to maximum expression and induction of RORγT, IL-17 and IL-17F. CCR6 cell surface expression was induced by TGF-β alone (FIG. 5a). In conditions that induce IL-17 expression, IL-17 was detected only in CCR6+ cells (FIG. 5b). FOXP3 expression was induced by an increasing concentration of TGF-β (FIG. 5c). Addition of IL-23, but not IL-1β, was able to suppress FOXP3 expression (FIG. 5c). IL-6 and IL-21 were also able to inhibit FOXP3 expression. Thus, the regulation of FOXP3 expression during Th17 cell differentiation is similar in mouse and humans.

DISCUSSION

Based on recent studies employing both in vitro culture systems and genetic approaches, it is now clear that TGF-β acts in concert with the pro-inflammatory cytokines IL-6, IL-21, and IL-23 to induce the differentiation of Th17 cells in mice[20]. Phosphorylation of Stat3 upon engagement of the inflammatory cytokine receptors[27, 44] and induction of Rorγt expression are essential for murine Th17 cell differentiation[21]. The requirement for TGF-β in Th17 cell differentiation was initially surprising, since it was known to act as an anti-inflammatory cytokine, at least in part through its induction and maintenance of regulatory T cells[22]. The function of TGF-β may be dependent on context and thresholds, favoring Th17 cell differentiation at low concentrations in the presence of inflammatory cytokines and Treg cell differentiation at high concentrations[43].

In light of its pivotal role in controlling the Th17 vs. Treg balance in mice, it was unclear why TGF-β was found to be inhibitory in the induction of IL-17 in human $CD4^+$ T cells with a naive surface phenotype[15, 29]. As described herein, the present inventors have used serum-free medium to reveal that TGF-β indeed has an essential role in the differentiation of naive human $CD4^+$ T cells towards the Th17 cell lineage, similar to what has been observed in mice. In human T cells, TGF-β induced RORγT expression yet paradoxically inhibited its transcriptional activity, thus preventing expression of IL-17. A combination of IL-1β and any one of IL-6, IL-21 or IL-23 relieved this inhibition and also contributed to RORγT expression, leading to induction of IL-17. Thus, similarly to the mouse, TGF-β is required for IL-17 expression in human T cells and additional transcription factors induced by IL-1β and IL-6, IL-21 or IL-23 may be involved in inducing IL-17 expression.

The present inventors have demonstrated a requirement for IL-23 for in vitro human Th17 cell differentiation, which contrasts with what has been observed in the mouse, where IL-23 is required only in vivo[18]. However, with low concentrations of TGF-β in mouse T cell culture, a positive effect of IL-23 on production of IL-17 was found[43]. Therefore, the discrepancy between the mouse and human systems with regards to IL-23 may be due to different culture conditions or different sensitivities to TGF-β. The inflammatory cytokines IL-6, IL-21 and IL-23 share signaling pathways by activating both STAT1 and STAT3[45-49], while IL-1β is thought to activate IRAK1/2 through recruitment of Myd88[50, 51]. Thus, STAT3 is likely to be a common denominator in the induction of RORγT and IL-17 expression in both species[20]. The IL-1 pathway is important for the in vivo induction of Th17 cells in the mouse, but it does not appear to be required for polarization in vitro in the presence of serum[52, 53]. It remains to be determined whether an unrecognized requirement downstream of the IL-1 receptor is also needed during murine Th17 cell differentiation in vitro.

Previous observations showing inhibitory activity of TGF-β in human Th17 cell differentiation were probably confounded by the use of serum and non-optimal naive cell purification[28, 29]. Indeed, TGF-β has long been recognized to be a "switch" cytokine highly context- and concentration-dependent[54]. The present inventors revealed an essential effect of exogenous TGF-β in Th17 cell differentiation by using serum-free media, suggesting that TGF-β present in serum might have masked this effect. However, neutralization of TGF-β did not strongly abolish the inhibitory effect of serum on RORγT-directed IL-17 expression, and TGF-β was not able to completely inhibit IL-17 expression following RORγT over-expression in serum-free conditions. This indicates that the presence of unidentified inhibitory factors in the serum synergize with TGF-β to counteract Th17 cell differentiation.

In addition to IL-17, the present inventors have shown that IL-17F and IL-26 are induced by RORγT overexpression and cytokine polarization. IL-26 has been shown to target epithelial cells and has been suggested to play a role in mucosal immunity[55], which is consistent with its induction in Th17 cells. Rearrangements of the Il22/Ifng locus seem to have occurred in the mouse/rat lineage leading to a loss of Il26, but this cytokine may have a major role in host defense and inflammation in humans. Expression of IL-22 in human T cells was inhibited by TGF-β, in accordance with observations in mouse systems[14].

While all $IL-17^+$ cells were $CCR6^+$ following Th17 cell differentiation, CCR6 expression was induced by TGF-β. This is in agreement with the observation that $FOXP3^+$ cells can also express $CCR6^{56}$. As expected, FOXP3 expression was gradually induced by TGF-β alone in serum-free conditions. IL-6, IL-21 and IL-23 alone were able to suppress FOXP3 expression, similar to the mouse[20]. However, addition of IL-1β was required for the induction of IL-17 through a currently undefined mechanism.

In human memory cells, expression of both IL-17 and IFNγ is clearly detected, posing the question of their ontogeny. The polarization conditions described here for naive cells lead only to the generation of $IL-17^+IFNγ^-$ cells. It is likely that the high concentration of TGF-β required for Th17 polarization inhibits IFNγ expression. It remains to be determined whether IL-17 and IFNγ can be expressed simultaneously following T cell differentiation from naive cells. Functional plasticity in T helper cell differentiation has been observed[57]. Thus, it is possible that IL-17 or IFNγ is expressed only subsequently from a pool of differentiated Th1 or Th17 memory cells, respectively.

The present inventors previously demonstrated that the orphan nuclear receptor Rorγt is uniquely expressed in mouse T cells that produce IL-17 and is required for up-regulation of this cytokine in T cells both in vivo and in vitro[21]. The present inventors show herein that RORγT also has a central role in human Th17 cell differentiation. shRNA knockdown of RORγT in memory $CCR6^+$ cells resulted in a marked reduction of IL-17 expression, indicating that the nuclear receptor is required for maintenance of cytokine production in Th17 cells. This result does not rule out a small contribution in directing IL-17 expression by the closely related paralogue RORα, which was shown to have a similar role in mouse[58]. A strong enrichment of RORα mRNA in $CCR6^+$ cells compared to $CCR6^-$ cells was not, however, observed. Furthermore, RORα mRNA was not strongly induced by a combination of IL-1β, IL-23 and TGFβ that otherwise induced a 50-fold increase of RORγT mRNA. At least four differentially spliced isoforms of RORα have, however, been described and their respective transcriptional regulation has not been determined. Furthermore, the data herein do not exclude potential post-transcriptional regulation of RORα. Finally, the ability of RORβ to induce IL-17 expression needs to be evaluated in relevant cell types, since RORβ expression has not been detected in peripheral $CD4^+$ T cells.

The IL-23/Th17 axis has recently been implicated in multiple human diseases[59]. The present demonstration of a requirement for IL-23 in the differentiation of Th17 cells is relevant in light of multiple polymorphisms in the human IL23R gene that have been reported to be associated with Crohn's disease and psoriasis[19, 60-64]. It will be important to elucidate the roles of IL-1β, IL-6, IL-21 and IL-23 and TGF-β in the pathogenesis of human diseases involving Th17 cells. Importantly, the participation of TGF-β in the induction of Th17 and Treg cells will likely be critical in maintenance of immune system homeostasis, particularly at mucosal surfaces, and imbalance in this system may result in autoimmunity. In this context, the present results offer a working model for the study of human Th17 cell differentiation and provide new opportunities for manipulating these cells in inflammatory diseases.

EXAMPLE II

Experimental Methods

Mononuclear cells were prepared from human cord blood on FicollPAQUE gradients. CD4+ T cells were isolated on an autoMACS Pro using Miltenyi bead depletion of CD14+ and CD25+ cells followed by positive selection of CD4+ cells. Cord blood CD4+ T cells were >97% pure and 100% CD45RA+ and were used as such for initial transduction experiments. Naive cord blood CD4+ T cells were further purified respectively as CD3+CD4+CD25−HLA-DR−CD45RA+ by cell sorting on a FACSAria.

CD4+ T cells were stimulated by addition of anti-mouse IgG magnetic beads (Pierce) previously coated with purified anti-CD3 and anti-CD28 at final concentrations of 1 bead/cell and 1 µg/ml of each antibody. Cells were seeded at a concentration of $5\times10^5$ to $10^6$ cells/ml in U-bottom 96 well plates with anti-CD3/CD28 coated beads. IL-2 at 10 U/ml was added at day 0. For Th17 differentiation, 10 ng/ml IL-1β (eBioscience), 10 ng/ml IL-23 (eBioscience), and 10 ng/ml TGF-β1 (PeproTech) were added at day 0 and maintained throughout the experiment.

Cells were harvested at day 6. Total RNA was isolated using Trizol following the manufacturer's procedure. RNA was labeled using the standard 1-cycle procedure from Affymetrix. RNA was hybridized and analyzed on Affymetrix HGU133plus2 chips. Data was analyzed using the R package.

Results

The present inventors generated the expression profile of human cord blood naive CD4+ T cells cultured for 6 days in IL-2 (neutral conditions) or IL-2+IL-1β+IL-23+TGFβ (Th17 conditions). The relative expression fold change in the expression of each gene was determined by comparing the expression level of each gene in Th17 conditions versus neutral conditions. The present inventors have thus identified a list of genes that are either up-regulated or down-regulated by at least 2 fold. See Tables 3 and 4.

In accordance with the present invention, therefore, novel cellular markers characteristic of human Th-IL17+ cells are identified. Such cellular markers may contribute to functional properties of human Th-IL17+ cells. Accordingly, the identification of such cellular markers of human Th-IL17+ cells provides novel targets for therapeutic agents and intervention designed to modulate human Th-IL17+ cell differentiation and/or activity.

TABLE 3

Human genes that are up-regulated in Th17 conditions. Genes known to be up-regulated in the Th17 pathway are highlighted in bold as an indication of the validity of the data.

| order | gene name | fold change | description |
|---|---|---|---|
| 1 | IL17A | 460.3 | interleukin 17A |
| 2 | SOX2 | 64.1 | SRY (sex determining region Y)-box 2 |
| 3 | IL17F | 50.0 | interleukin 17F |
| 4 | CXCL13 | 49.3 | chemokine (C—X—C motif) ligand 13 (B-cell chemoattractant) |
| 5 | DIXDC1 | 36.8 | DIX domain containing 1 |
| 6 | DHRS9 | 30.0 | dehydrogenase/reductase (SDR family) member 9 |
| 7 | PTHLH | 26.6 | parathyroid hormone-like hormone |
| 8 | COL15A1 | 24.0 | collagen, type XV, alpha 1 |
| 9 | DSE | 22.5 | dermatan sulfate epimerase |
| 10 | SERPINA1 | 22.4 | serpin peptidase inhibitor, clade A (alpha-1 antiproteinase, antitrypsin), member 1 |
| 11 | IL23R | 22.2 | interleukin 23 receptor |
| 12 | FNBP1L | 21.6 | formin binding protein 1-like |
| 13 | IL9 | 21.4 | interleukin 9 |
| 14 | KISS1R | 16.7 | KISS1 receptor |
| 15 | GATM | 16.5 | glycine amidinotransferase (L-arginine:glycine amidinotransferase) |
| 16 | BASP1 | 16.2 | brain abundant, membrane attached signal protein 1 |
| 17 | THBS1 | 15.9 | thrombospondin 1 |
| 18 | SH3RF1 | 13.6 | SH3 domain containing ring finger 1 |
| 19 | CCNA1 | 12.2 | cyclin A1 |
| 20 | CXCR4 | 12.0 | chemokine (C—X—C motif) receptor 4 |
| 21 | IL1A | 11.9 | interleukin 1, alpha |
| 22 | CLIC5 | 11.2 | chloride intracellular channel 5 |
| 23 | AQP3 | 11.1 | aquaporin 3 (Gill blood group) |
| 24 | NAPSB | 11.0 | napsin B aspartic peptidase pseudogene |
| 25 | HOP | 10.4 | homeodomain-only protein |
| 26 | CCL20 | 10.3 | chemokine (C—C motif) ligand 20 |
| 27 | PLOD2 | 9.9 | procollagen-lysine, 2-oxoglutarate 5-dioxygenase 2 |
| 28 | PTCHD1 | 9.9 | patched domain containing 1 |
| 29 | CCR6 | 9.8 | chemokine (C—C motif) receptor 6 |
| 30 | IL1R2 | 9.5 | interleukin 1 receptor, type II |
| 31 | RCAN2 | 9.5 | regulator of calcineurin 2 |
| 32 | BCAR3 | 9.2 | breast cancer anti-estrogen resistance 3 |
| 33 | TIMP1 | 9.2 | TIMP metallopeptidase inhibitor 1 |
| 34 | EPAS1 | 9.2 | endothelial PAS domain protein 1 |
| 35 | MPP7 | 9.1 | membrane protein, palmitoylated 7 (MAGUK p55 subfamily member 7) |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 36 | KIF5C | 8.7 | kinesin family member 5C |
| 37 | PLEKHA5 | 8.7 | pleckstrin homology domain containing, family A member 5 |
| 38 | LTA | 8.6 | lymphotoxin alpha (TNF superfamily, member 1) |
| 39 | RORA | 8.5 | RAR-related orphan receptor A |
| 40 | RGS16 | 8.4 | regulator of G-protein signaling 16 |
| 41 | C13orf18 | 8.4 | chromosome 13 open reading frame 18 |
| 42 | TMEM154 | 8.3 | transmembrane protein 154 |
| 43 | PRG4 | 8.3 | proteoglycan 4 |
| 44 | WBP5 | 8.3 | WW domain binding protein 5 |
| 45 | DNM3 | 8.1 | dynamin 3 |
| 46 | LOC283666 | 7.9 | hypothetical protein LOC283666 |
| 47 | KIAA0828 | 7.9 | adenosylhomocysteinase 3 |
| 48 | HBEGF | 7.7 | heparin-binding EGF-like growth factor |
| 49 | MRC1 | 7.5 | mannose receptor, C type 1 |
| 50 | BMPR2 | 7.5 | bone morphogenetic protein receptor, type II (serine/threonine kinase) |
| 51 | CTSL1 | 7.4 | cathepsin L1 |
| 52 | NA | 7.1 | NA |
| 53 | EPHA4 | 6.9 | EPH receptor A4 |
| 54 | MYO10 | 6.8 | myosin X |
| 55 | NRIP3 | 6.7 | nuclear receptor interacting protein 3 |
| 56 | CXCL3 | 6.7 | chemokine (C—X—C motif) ligand 3 |
| 57 | LRP11 | 6.6 | low density lipoprotein receptor-related protein 11 |
| 58 | PTK2 | 6.4 | PTK2 protein tyrosine kinase 2 |
| 59 | PERP | 6.4 | PERP, TP53 apoptosis effector |
| 60 | SMARCA2 | 6.4 | SWI/SNF related, matrix associated, actin dependent regulator of chromatin, subfamily a, member 2 |
| 61 | DDIT4 | 6.4 | DNA-damage-inducible transcript 4 |
| 62 | SEPT10 | 6.4 | septin 10 |
| 63 | MGST1 | 6.2 | microsomal glutathione S-transferase 1 |
| 64 | RAB13 | 6.0 | RAB13, member RAS oncogene family |
| 65 | SLC1A1 | 6.0 | solute carrier family 1 (neuronal/epithelial high affinity glutamate transporter, system Xag), member 1 |
| 66 | PALM2-AKAP2 | 5.9 | PALM2-AKAP2 protein |
| 67 | UCHL1 | 5.9 | ubiquitin carboxyl-terminal esterase L1 (ubiquitin thiolesterase) |
| 68 | RBMS3 | 5.7 | RNA binding motif, single stranded interacting protein |
| 69 | CRISPLD1 | 5.7 | cysteine-rich secretory protein LCCL domain containing 1 |
| 70 | COL5A2 | 5.6 | collagen, type V, alpha 2 |
| 71 | PGBD1 | 5.6 | piggyBac transposable element derived 1 |
| 72 | CCDC88A | 5.5 | coiled-coil domain containing 88A |
| 73 | DBN1 | 5.4 | drebrin 1 |
| 74 | RUNX1 | 5.4 | runt-related transcription factor 1 (acute myeloid leukemia 1; aml1 oncogene) |
| 75 | B4GALT6 | 5.4 | UDP-Gal:betaGlcNAc beta 1,4-galactosyltransferase, polypeptide 6 |
| 76 | MAP1B | 5.4 | microtubule-associated protein 1B |
| 77 | SNX7 | 5.4 | sorting nexin 7 |
| 78 | OSM | 5.3 | oncostatin M |
| 79 | S100A2 | 5.3 | S100 calcium binding protein A2 |
| 80 | AYTL1 | 5.3 | acyltransferase like 1 |
| 81 | LGALS3 | 5.3 | lectin, galactoside-binding, soluble, 3 |
| 82 | IL26 | 5.3 | interleukin 26 |
| 83 | COL6A3 | 5.2 | collagen, type VI, alpha 3 |
| 84 | ARMCX2 | 5.1 | armadillo repeat containing, X-linked 2 |
| 85 | DHRS2 | 5.1 | dehydrogenase/reductase (SDR family) member 2 |
| 86 | MLLT11 | 5.0 | myeloid/lymphoid or mixed-lineage leukemia (trithorax homolog, Drosophila); translocated to, 11 |
| 87 | CHN1 | 5.0 | chimerin (chimaerin) 1 |
| 88 | ANXA3 | 5.0 | annexin A3 |
| 89 | GNA11 | 5.0 | guanine nucleotide binding protein (G protein), alpha 11 (Gq class) |
| 90 | GALNT10 | 5.0 | UDP-N-acetyl-alpha-D-galactosamine:polypeptide N-acetylgalactosaminyltransferase 10 (GalNAc-T10) |
| 91 | UPK1B | 4.9 | uroplakin 1B |
| 92 | RHPN2 | 4.9 | rhophilin, Rho GTPase binding protein 2 |
| 93 | DNAJC12 | 4.9 | DnaJ (Hsp40) homolog, subfamily C, member 12 |
| 94 | PKIG | 4.9 | protein kinase (cAMP-dependent, catalytic) inhibitor gamma |
| 95 | C1orf218 | 4.9 | chromosome 1 open reading frame 218 |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 96 | PALLD | 4.9 | palladin, cytoskeletal associated protein |
| 97 | APOD | 4.9 | apolipoprotein D |
| 98 | TPD52 | 4.8 | tumor protein D52 |
| 99 | PSCD3 | 4.8 | pleckstrin homology, Sec7 and coiled-coil domains 3 |
| 100 | LOC286052 | 4.8 | hypothetical protein LOC286052 |
| 101 | HSDL2 | 4.7 | hydroxysteroid dehydrogenase like 2 |
| 102 | SLC44A1 | 4.7 | solute carrier family 44, member 1 |
| 103 | FAM119A | 4.7 | family with sequence similarity 119, member A |
| 104 | PNOC | 4.7 | prepronociceptin |
| 105 | MOBKL2B | 4.7 | MOB1, Mps One Binder kinase activator-like 2B (yeast) |
| 106 | ELK3 | 4.7 | ELK3, ETS-domain protein (SRF accessory protein 2) |
| 107 | TRERF1 | 4.6 | transcriptional regulating factor 1 |
| 108 | PDE4DIP | 4.6 | phosphodiesterase 4D interacting protein (myomegalin) |
| 109 | C10orf58 | 4.6 | chromosome 10 open reading frame 58 |
| 110 | ELL2 | 4.6 | elongation factor, RNA polymerase II, 2 |
| 111 | LOC286144 | 4.5 | hypothetical protein LOC286144 |
| 112 | CYB5R2 | 4.5 | cytochrome b5 reductase 2 |
| 113 | RORC | 4.5 | RAR-related orphan receptor C |
| 114 | LOC285957 | 4.3 | hypothetical protein LOC285957 |
| 115 | PWCR1 | 4.3 | Prader-Willi syndrome chromosome region 1 |
| 116 | IL2RB | 4.3 | interleukin 2 receptor, beta |
| 117 | OLAH | 4.3 | oleoyl-ACP hydrolase |
| 118 | RAB34 | 4.2 | RAB34, member RAS oncogene family |
| 119 | SYT11 | 4.2 | synaptotagmin XI |
| 120 | ABCG2 | 4.1 | ATP-binding cassette, sub-family G (WHITE), member 2 |
| 121 | TMEM65 | 4.1 | transmembrane protein 65 |
| 122 | RYR1 | 4.1 | ryanodine receptor 1 (skeletal) |
| 123 | PLEKHC1 | 4.0 | pleckstrin homology domain containing, family C (with FERM domain) member 1 |
| 124 | CCDC3 | 4.0 | coiled-coil domain containing 3 |
| 125 | IMPA2 | 4.0 | inositol(myo)-1(or 4)-monophosphatase 2 |
| 126 | MMP2 | 4.0 | matrix metallopeptidase 2 (gelatinase A, 72 kDa gelatinase, 72 kDa type IV collagenase) |
| 127 | C12orf39 | 4.0 | chromosome 12 open reading frame 39 |
| 128 | CTSH | 4.0 | cathepsin H |
| 129 | NEFH | 4.0 | neurofilament, heavy polypeptide 200 kDa |
| 130 | RAB23 | 4.0 | RAB23, member RAS oncogene family |
| 131 | RTKN | 4.0 | rhotekin |
| 132 | PLAGL1 | 4.0 | pleiomorphic adenoma gene-like 1 |
| 133 | SCARB2 | 3.9 | scavenger receptor class B, member 2 |
| 134 | C14orf145 | 3.9 | chromosome 14 open reading frame 145 |
| 135 | MST150 | 3.9 | MSTP150 |
| 136 | LIPG | 3.9 | lipase, endothelial |
| 137 | IDS | 3.9 | iduronate 2-sulfatase (Hunter syndrome) |
| 138 | PITPNC1 | 3.8 | phosphatidylinositol transfer protein, cytoplasmic 1 |
| 139 | FAM102B | 3.8 | family with sequence similarity 102, member B |
| 140 | HLX | 3.8 | H2.0-like homeobox |
| 141 | CXCL12 | 3.8 | chemokine (C—X—C motif) ligand 12 (stromal cell-derived factor 1) |
| 142 | C9orf72 | 3.8 | chromosome 9 open reading frame 72 |
| 143 | TTC28 | 3.8 | tetratricopeptide repeat domain 28 |
| 144 | DYNC2LI1 | 3.8 | dynein, cytoplasmic 2, light intermediate chain 1 |
| 145 | PHYH | 3.8 | phytanoyl-CoA 2-hydroxylase |
| 146 | DMXL2 | 3.8 | Dmx-like 2 |
| 147 | TRPC1 | 3.8 | transient receptor potential cation channel, subfamily C, member 1 |
| 148 | C18orf1 | 3.8 | chromosome 18 open reading frame 1 |
| 149 | HSPA1A | 3.8 | heat shock 70 kDa protein 1A |
| 150 | BNIP3L | 3.8 | BCL2/adenovirus E1B 19 kDa interacting protein 3-like |
| 151 | ITGA2 | 3.7 | integrin, alpha 2 (CD49B, alpha 2 subunit of VLA-2 receptor) |
| 152 | CLGN | 3.7 | calmegin |
| 153 | PIGF | 3.7 | phosphatidylinositol glycan anchor biosynthesis, class F |
| 154 | INADL | 3.7 | InaD-like (*Drosophila*) |
| 155 | PLS1 | 3.7 | plastin 1 (I isoform) |
| 156 | GYS2 | 3.7 | glycogen synthase 2 (liver) |
| 157 | NGFRAP1 | 3.7 | nerve growth factor receptor (TNFRSF16) associated protein 1 |
| 158 | MYB | 3.7 | v-myb myeloblastosis viral oncogene homolog (avian) |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 159 | TNFRSF12A | 3.7 | tumor necrosis factor receptor superfamily, member 12A |
| 160 | RP13-36C9.3 | 3.7 | cancer/testis antigen CT45-3 |
| 161 | PLTP | 3.7 | phospholipid transfer protein |
| 162 | MIPEP | 3.7 | mitochondrial intermediate peptidase |
| 163 | NPW | 3.7 | neuropeptide W |
| 164 | LTB | 3.6 | lymphotoxin beta (TNF superfamily, member 3) |
| 165 | SORL1 | 3.6 | sortilin-related receptor, L(DLR class) A repeats-containing |
| 166 | ZNRF1 | 3.6 | zinc and ring finger 1 |
| 167 | TMEM5 | 3.6 | transmembrane protein 5 |
| 168 | DFNA5 | 3.6 | deafness, autosomal dominant 5 |
| 169 | ITGAE | 3.6 | integrin, alpha E (antigen CD103, human mucosal lymphocyte antigen 1; alpha polypeptide) |
| 170 | TCEAL4 | 3.6 | transcription elongation factor A (SII)-like 4 |
| 171 | CCR4 | 3.6 | chemokine (C—C motif) receptor 4 |
| 172 | AKAP12 | 3.6 | A kinase (PRKA) anchor protein (gravin) 12 |
| 173 | SWAP70 | 3.6 | SWAP-70 protein |
| 174 | NTRK2 | 3.5 | neurotrophic tyrosine kinase, receptor, type 2 |
| 175 | GPR160 | 3.5 | G protein-coupled receptor 160 |
| 176 | TPK1 | 3.5 | thiamin pyrophosphokinase 1 |
| 177 | Rgr | 3.5 | Ral-GDS related protein Rgr |
| 178 | CSRP2 | 3.5 | cysteine and glycine-rich protein 2 |
| 179 | ALDH5A1 | 3.5 | aldehyde dehydrogenase 5 family, member A1 (succinate-semialdehyde dehydrogenase) |
| 180 | TMEPAI | 3.5 | transmembrane, prostate androgen induced RNA |
| 181 | PRKCDBP | 3.5 | protein kinase C, delta binding protein |
| 182 | LIF | 3.5 | leukemia inhibitory factor (cholinergic differentiation factor) |
| 183 | IFT74 | 3.5 | intraflagellar transport 74 homolog (*Chlamydomonas*) |
| 184 | LPGAT1 | 3.5 | lysophosphatidylglycerol acyltransferase 1 |
| 185 | TARSL2 | 3.5 | threonyl-tRNA synthetase-like 2 |
| 186 | NPAS2 | 3.5 | neuronal PAS domain protein 2 |
| 187 | TANC1 | 3.5 | tetratricopeptide repeat, ankyrin repeat and coiled-coil containing 1 |
| 188 | DHTKD1 | 3.4 | dehydrogenase E1 and transketolase domain containing 1 |
| 189 | TCFL5 | 3.4 | transcription factor-like 5 (basic helix-loop-helix) |
| 190 | GLB1 | 3.4 | galactosidase, beta 1 |
| 191 | HLA-DPB1 | 3.4 | major histocompatibility complex, class II, DP beta 1 |
| 192 | RAB33A | 3.4 | RAB33A, member RAS oncogene family |
| 193 | ASPH | 3.4 | aspartate beta-hydroxylase |
| 194 | LOC401397 | 3.4 | hypothetical LOC401397 |
| 195 | ACN9 | 3.4 | ACN9 homolog (*S. cerevisiae*) |
| 196 | B4GALT4 | 3.4 | UDP-Gal:betaGlcNAc beta 1,4-galactosyltransferase, polypeptide 4 |
| 197 | hCG_1815491 | 3.4 | hCG1815491 |
| 198 | KIAA0888 | 3.4 | KIAA0888 protein |
| 199 | C3orf28 | 3.4 | chromosome 3 open reading frame 28 |
| 200 | RPP30 | 3.4 | ribonuclease P/MRP 30 kDa subunit |
| 201 | PDE6D | 3.4 | phosphodiesterase 6D, cGMP-specific, rod, delta |
| 202 | SYN1 | 3.4 | synapsin I |
| 203 | MCAM | 3.4 | melanoma cell adhesion molecule |
| 204 | UPP1 | 3.4 | uridine phosphorylase 1 |
| 205 | CASP6 | 3.4 | caspase 6, apoptosis-related cysteine peptidase |
| 206 | LYN | 3.4 | v-yes-1 Yamaguchi sarcoma viral related oncogene homolog |
| 207 | OCIAD2 | 3.4 | OCIA domain containing 2 |
| 208 | LOC729680 | 3.4 | hypothetical protein LOC729680 |
| 209 | KIAA1450 | 3.3 | KIAA1450 protein |
| 210 | FRMD6 | 3.3 | FERM domain containing 6 |
| 211 | SYNE1 | 3.3 | spectrin repeat containing, nuclear envelope 1 |
| 212 | PTGFRN | 3.3 | prostaglandin F2 receptor negative regulator |
| 213 | TIFA | 3.3 | TRAF-interacting protein with a forkhead-associated domain |
| 214 | TCEAL8 | 3.3 | transcription elongation factor A (SII)-like 8 |
| 215 | RLBP1L1 | 3.3 | retinaldehyde binding protein 1-like 1 |
| 216 | HLA-DPA1 | 3.3 | major histocompatibility complex, class II, DP alpha 1 |
| 217 | NME4 | 3.3 | non-metastatic cells 4, protein expressed in |
| 218 | EPDR1 | 3.3 | ependymin related protein 1 (zebrafish) |
| 219 | PNMA2 | 3.3 | paraneoplastic antigen MA2 |
| 220 | MAN1C1 | 3.3 | mannosidase, alpha, class 1C, member 1 |
| 221 | CYFIP2 | 3.3 | cytoplasmic FMR1 interacting protein 2 |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 222 | LEPR | 3.3 | leptin receptor |
| 223 | PSPH | 3.3 | phosphoserine phosphatase |
| 224 | HSPA1B | 3.3 | heat shock 70 kDa protein 1B |
| 225 | EPOR | 3.2 | erythropoietin receptor |
| 226 | TRAF3IP1 | 3.2 | TNF receptor-associated factor 3 interacting protein 1 |
| 227 | ENO2 | 3.2 | enolase 2 (gamma, neuronal) |
| 228 | GALM | 3.2 | galactose mutarotase (aldose 1-epimerase) |
| 229 | SOCS2 | 3.2 | suppressor of cytokine signaling 2 |
| 230 | CTLA4 | 3.2 | cytotoxic T-lymphocyte-associated protein 4 |
| 231 | ETV5 | 3.2 | ets variant gene 5 (ets-related molecule) |
| 232 | SPRED1 | 3.2 | sprouty-related, EVH1 domain containing 1 |
| 233 | THYN1 | 3.2 | thymocyte nuclear protein 1 |
| 234 | TM4SF1 | 3.2 | transmembrane 4 L six family member 1 |
| 235 | CBS | 3.2 | cystathionine-beta-synthase |
| 236 | LPL | 3.2 | lipoprotein lipase |
| 237 | TGFBI | 3.2 | transforming growth factor, beta-induced, 68 kDa |
| 238 | KL | 3.2 | klotho |
| 239 | FAM92A1 | 3.2 | family with sequence similarity 92, member A1 |
| 240 | C22orf16 | 3.2 | chromosome 22 open reading frame 16 |
| 241 | TMEM110 | 3.2 | transmembrane protein 110 |
| 242 | LRRC16 | 3.2 | leucine rich repeat containing 16 |
| 243 | TMEM118 | 3.2 | transmembrane protein 118 |
| 244 | ADCY3 | 3.1 | adenylate cyclase 3 |
| 245 | ATP8B2 | 3.1 | ATPase, Class I, type 8B, member 2 |
| 246 | TGFB1 | 3.1 | transforming growth factor, beta 1 |
| 247 | C11orf74 | 3.1 | chromosome 11 open reading frame 74 |
| 248 | NT5DC1 | 3.1 | 5'-nucleotidase domain containing 1 |
| 249 | SUHW2 | 3.1 | suppressor of hairy wing homolog 2 (*Drosophila*) |
| 250 | GRAMD3 | 3.1 | GRAM domain containing 3 |
| 251 | PLA2G12A | 3.1 | phospholipase A2, group XIIA |
| 252 | APAF1 | 3.1 | apoptotic peptidase activating factor 1 |
| 253 | GLT1D1 | 3.1 | glycosyltransferase 1 domain containing 1 |
| 254 | DEPDC1 | 3.1 | DEP domain containing 1 |
| 255 | PVRIG | 3.1 | poliovirus receptor related immunoglobulin domain containing |
| 256 | TNRC8 | 3.1 | trinucleotide repeat containing 8 |
| 257 | LPXN | 3.1 | leupaxin |
| 258 | LYPLAL1 | 3.1 | lysophospholipase-like 1 |
| 259 | AIF1 | 3.1 | allograft inflammatory factor 1 |
| 260 | CORO2A | 3.1 | coronin, actin binding protein, 2A |
| 261 | TUSC3 | 3.1 | tumor suppressor candidate 3 |
| 262 | ADH5 | 3.1 | alcohol dehydrogenase 5 (class III), chi polypeptide |
| 263 | LOC647500 | 3.1 | similar to phosphodiesterase 4D interacting protein isoform 1 |
| 264 | CCDC34 | 3.1 | coiled-coil domain containing 34 |
| 265 | SSX2IP | 3.1 | synovial sarcoma, X breakpoint 2 interacting protein |
| 266 | TBC1D9 | 3.1 | TBC1 domain family, member 9 (with GRAM domain) |
| 267 | MORN2 | 3.1 | MORN repeat containing 2 |
| 268 | LPHN1 | 3.0 | latrophilin 1 |
| 269 | C14orf143 | 3.0 | chromosome 14 open reading frame 143 |
| 270 | RLN2 | 3.0 | relaxin 2 |
| 271 | C6orf170 | 3.0 | chromosome 6 open reading frame 170 |
| 272 | ZYG11B | 3.0 | zyg-11 homolog B (*C. elegans*) |
| 273 | ELOVL4 | 3.0 | elongation of very long chain fatty acids (FEN1/Elo2, SUR4/Elo3, yeast)-like 4 |
| 274 | TTC8 | 3.0 | tetratricopeptide repeat domain 8 |
| 275 | ARMCX1 | 3.0 | armadillo repeat containing, X-linked 1 |
| 276 | TUBA1A | 3.0 | tubulin, alpha 1a |
| 277 | TMEFF1 | 3.0 | transmembrane protein with EGF-like and two follistatin-like domains 1 |
| 278 | HLA-DMA | 3.0 | major histocompatibility complex, class II, DM alpha |
| 279 | MYO1G | 3.0 | myosin IG |
| 280 | LOC157278 | 3.0 | hypothetical protein LOC157278 |
| 281 | CCDC53 | 3.0 | coiled-coil domain containing 53 |
| 282 | C1orf25 | 3.0 | chromosome 1 open reading frame 25 |
| 283 | STAMBPL1 | 3.0 | STAM binding protein-like 1 |
| 284 | ADRBK2 | 3.0 | adrenergic, beta, receptor kinase 2 |
| 285 | CDC42BPB | 3.0 | CDC42 binding protein kinase beta (DMPK-like) |
| 286 | ZNF697 | 3.0 | zinc finger protein 697 |
| 287 | AIG1 | 3.0 | androgen-induced 1 |
| 288 | S100A6 | 3.0 | S100 calcium binding protein A6 |
| 289 | CKAP4 | 3.0 | cytoskeleton-associated protein 4 |
| 290 | RPL39L | 2.9 | ribosomal protein L39-like |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 291 | NLRP3 | 2.9 | NLR family, pyrin domain containing 3 |
| 292 | TMEM14A | 2.9 | transmembrane protein 14A |
| 293 | MNDA | 2.9 | myeloid cell nuclear differentiation antigen |
| 294 | RCAN3 | 2.9 | RCAN family member 3 |
| 295 | ZBTB8 | 2.9 | zinc finger and BTB domain containing 8 |
| 296 | FTO | 2.9 | fat mass and obesity associated |
| 297 | MIB1 | 2.9 | mindbomb homolog 1 (Drosophila) |
| 298 | PPARG | 2.9 | peroxisome proliferator-activated receptor gamma |
| 299 | ANLN | 2.9 | anillin, actin binding protein |
| 300 | SQRDL | 2.9 | sulfide quinone reductase-like (yeast) |
| 301 | AOF1 | 2.9 | amine oxidase (flavin containing) domain 1 |
| 302 | LRRCC1 | 2.9 | leucine rich repeat and coiled-coil domain containing 1 |
| 303 | SMYD3 | 2.9 | SET and MYND domain containing 3 |
| 304 | SCHIP1 | 2.9 | schwannomin interacting protein 1 |
| 305 | C2orf33 | 2.9 | chromosome 2 open reading frame 33 |
| 306 | DMD | 2.9 | dystrophin (muscular dystrophy, Duchenne and Becker types) |
| 307 | CCDC74B | 2.9 | coiled-coil domain containing 74B |
| 308 | PLCXD2 | 2.9 | phosphatidylinositol-specific phospholipase C, X domain containing 2 |
| 309 | LXN | 2.9 | latexin |
| 310 | LTB4DH | 2.9 | leukotriene B4 12-hydroxydehydrogenase |
| 311 | TUBG1 | 2.9 | tubulin, gamma 1 |
| 312 | ECGF1 | 2.9 | endothelial cell growth factor 1 (platelet-derived) |
| 313 | SPIRE1 | 2.9 | spire homolog 1 (Drosophila) |
| 314 | HTATIP2 | 2.9 | HIV-1 Tat interactive protein 2, 30 kDa |
| 315 | CRYZ | 2.9 | crystallin, zeta (quinone reductase) |
| 316 | FAM33A | 2.9 | family with sequence similarity 33, member A |
| 317 | C3orf14 | 2.9 | chromosome 3 open reading frame 14 |
| 318 | PLEKHA8 | 2.9 | pleckstrin homology domain containing, family A (phosphoinositide binding specific) member 8 |
| 319 | PPIL4 | 2.9 | peptidylprolyl isomerase (cyclophilin)-like 4 |
| 320 | DOCK7 | 2.9 | dedicator of cytokinesis 7 |
| 321 | SIAE | 2.9 | sialic acid acetylesterase |
| 322 | FKBP1B | 2.9 | FK506 binding protein 1B, 12.6 kDa |
| 323 | MCM6 | 2.9 | minichromosome maintenance complex component 6 |
| 324 | TMTC4 | 2.9 | transmembrane and tetratricopeptide repeat containing 4 |
| 325 | KLHDC5 | 2.9 | kelch domain containing 5 |
| 326 | DNAJC6 | 2.9 | DnaJ (Hsp40) homolog, subfamily C, member 6 |
| 327 | PDLIM5 | 2.8 | PDZ and LIM domain 5 |
| 328 | PON2 | 2.8 | paraoxonase 2 |
| 329 | FLJ13305 | 2.8 | hypothetical protein FLJ13305 |
| 330 | NELL2 | 2.8 | NEL-like 2 (chicken) |
| 331 | C18orf50 | 2.8 | chromosome 18 open reading frame 50 |
| 332 | KIAA0746 | 2.8 | KIAA0746 protein |
| 333 | PIK3CB | 2.8 | phosphoinositide-3-kinase, catalytic, beta polypeptide |
| 334 | KIAA1841 | 2.8 | KIAA1841 |
| 335 | PGAP1 | 2.8 | GPI deacylase |
| 336 | KLHL7 | 2.8 | kelch-like 7 (Drosophila) |
| 337 | C5orf34 | 2.8 | chromosome 5 open reading frame 34 |
| 338 | CARD8 | 2.8 | caspase recruitment domain family, member 8 |
| 339 | PEG3 | 2.8 | paternally expressed 3 |
| 340 | ACPL2 | 2.8 | acid phosphatase-like 2 |
| 341 | PRR6 | 2.8 | proline rich 6 |
| 342 | HLA-DQB1 | 2.8 | major histocompatibility complex, class II, DQ beta 1 |
| 343 | TXNDC17 | 2.8 | thioredoxin domain containing 17 |
| 344 | SRI | 2.8 | sorcin |
| 345 | BNIP3 | 2.8 | BCL2/adenovirus E1B 19 kDa interacting protein 3 |
| 346 | AHR | 2.8 | aryl hydrocarbon receptor |
| 347 | SPG3A | 2.8 | spastic paraplegia 3A (autosomal dominant) |
| 348 | GSTO1 | 2.8 | glutathione S-transferase omega 1 |
| 349 | FLI1 | 2.8 | Friend leukemia virus integration 1 |
| 350 | NEK2 | 2.8 | NIMA (never in mitosis gene a)-related kinase 2 |
| 351 | FLOT1 | 2.7 | flotillin 1 |
| 352 | FLJ39739 | 2.7 | hypothetical FLJ39739 |
| 353 | LOC728855 | 2.7 | hypothetical protein LOC728855 |
| 354 | EHBP1 | 2.7 | EH domain binding protein 1 |
| 355 | PAAF1 | 2.7 | proteasomal ATPase-associated factor 1 |
| 356 | HLTF | 2.7 | helicase-like transcription factor |
| 357 | TUFT1 | 2.7 | tuftelin 1 |
| 358 | TNFRSF11B | 2.7 | tumor necrosis factor receptor superfamily, member 11b (osteoprotegerin) |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 359 | MMD | 2.7 | monocyte to macrophage differentiation-associated |
| 360 | HPS3 | 2.7 | Hermansky-Pudlak syndrome 3 |
| 361 | P2RX5 | 2.7 | purinergic receptor P2X, ligand-gated ion channel, 5 |
| 362 | C15orf48 | 2.7 | chromosome 15 open reading frame 48 |
| 363 | ACY1L2 | 2.7 | aminoacylase 1-like 2 |
| 364 | SFXN3 | 2.7 | sideroflexin 3 |
| 365 | FAS | 2.7 | Fas (TNF receptor superfamily, member 6) |
| 366 | ANAPC10 | 2.7 | anaphase promoting complex subunit 10 |
| 367 | ZNF652 | 2.7 | zinc finger protein 652 |
| 368 | LOXL3 | 2.7 | lysyl oxidase-like 3 |
| 369 | SLC16A2 | 2.7 | solute carrier family 16, member 2 (monocarboxylic acid transporter 8) |
| 370 | AMPD3 | 2.7 | adenosine monophosphate deaminase (isoform E) |
| 371 | CDK5 | 2.7 | cyclin-dependent kinase 5 |
| 372 | PPP3CB | 2.7 | protein phosphatase 3 (formerly 2B), catalytic subunit, beta isoform |
| 373 | C9orf30 | 2.7 | chromosome 9 open reading frame 30 |
| 374 | HLA-DRA | 2.7 | major histocompatibility complex, class II, DR alpha |
| 375 | CAPN2 | 2.7 | calpain 2, (m/II) large subunit |
| 376 | MGAT4A | 2.7 | mannosyl (alpha-1,3-)-glycoprotein beta-1,4-N-acetylglucosaminyltransferase, isozyme A |
| 377 | UROD | 2.7 | uroporphyrinogen decarboxylase |
| 378 | TNFRSF11A | 2.7 | tumor necrosis factor receptor superfamily, member 11a, NFKB activator |
| 379 | LOC440295 | 2.7 | hypothetical protein LOC440295 |
| 380 | DOCK4 | 2.7 | dedicator of cytokinesis 4 |
| 381 | C6orf145 | 2.7 | chromosome 6 open reading frame 145 |
| 382 | BCL11B | 2.7 | B-cell CLL/lymphoma 11B (zinc finger protein) |
| 383 | RP11-529I10.4 | 2.7 | deleted in a mouse model of primary ciliary dyskinesia |
| 384 | DAZL | 2.7 | deleted in azoospermia-like |
| 385 | CCDC92 | 2.7 | coiled-coil domain containing 92 |
| 386 | LOC389203 | 2.7 | hypothetical gene supported by BC032431 |
| 387 | FUCA1 | 2.7 | fucosidase, alpha-L-1, tissue |
| 388 | MGC16169 | 2.7 | hypothetical protein MGC16169 |
| 389 | CLDN12 | 2.7 | claudin 12 |
| 390 | MAK | 2.7 | male germ cell-associated kinase |
| 391 | XRCC6BP1 | 2.7 | XRCC6 binding protein 1 |
| 392 | BAD | 2.7 | BCL2-antagonist of cell death |
| 393 | MAP9 | 2.7 | microtubule-associated protein 9 |
| 394 | CETN3 | 2.7 | centrin, EF-hand protein, 3 (CDC31 homolog, yeast) |
| 395 | CACYBP | 2.7 | calcyclin binding protein |
| 396 | ROBO1 | 2.7 | roundabout, axon guidance receptor, homolog 1 (*Drosophila*) |
| 397 | TAX1BP3 | 2.6 | Tax1 (human T-cell leukemia virus type I) binding protein 3 |
| 398 | FLJ11151 | 2.6 | hypothetical protein FLJ11151 |
| 399 | ITGA6 | 2.6 | integrin, alpha 6 |
| 400 | RAVER2 | 2.6 | ribonucleoprotein, PTB-binding 2 |
| 401 | GPR155 | 2.6 | G protein-coupled receptor 155 |
| 402 | SLC8A1 | 2.6 | solute carrier family 8 (sodium/calcium exchanger), member 1 |
| 403 | ABHD7 | 2.6 | abhydrolase domain containing 7 |
| 404 | SYNGR3 | 2.6 | synaptogyrin 3 |
| 405 | FBXO31 | 2.6 | F-box protein 31 |
| 406 | GK5 | 2.6 | glycerol kinase 5 (putative) |
| 407 | TEAD1 | 2.6 | TEA domain family member 1 (SV40 transcriptional enhancer factor) |
| 408 | CORO1B | 2.6 | coronin, actin binding protein, 1B |
| 409 | OSGEPL1 | 2.6 | O-sialoglycoprotein endopeptidase-like 1 |
| 410 | ACAA2 | 2.6 | acetyl-Coenzyme A acyltransferase 2 (mitochondrial 3-oxoacyl-Coenzyme A thiolase) |
| 411 | RBMS1 | 2.6 | RNA binding motif, single stranded interacting protein 1 |
| 412 | GM2A | 2.6 | GM2 ganglioside activator |
| 413 | COX11 | 2.6 | COX11 homolog, cytochrome c oxidase assembly protein (yeast) |
| 414 | ATPBD4 | 2.6 | ATP binding domain 4 |
| 415 | GSTM3 | 2.6 | glutathione S-transferase M3 (brain) |
| 416 | SKP2 | 2.6 | S-phase kinase-associated protein 2 (p45) |
| 417 | PAK1 | 2.6 | p21/Cdc42/Rac1-activated kinase 1 (STE20 homolog, yeast) |
| 418 | ACTN1 | 2.6 | actinin, alpha 1 |
| 419 | MYEF2 | 2.6 | myelin expression factor 2 |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 420 | ERLIN2 | 2.6 | ER lipid raft associated 2 |
| 421 | VLDLR | 2.6 | very low density lipoprotein receptor |
| 422 | WDR54 | 2.6 | WD repeat domain 54 |
| 423 | GRK5 | 2.6 | G protein-coupled receptor kinase 5 |
| 424 | ARHGAP30 | 2.6 | Rho GTPase activating protein 30 |
| 425 | ANKRD57 | 2.6 | ankyrin repeat domain 57 |
| 426 | MYH10 | 2.6 | myosin, heavy chain 10, non-muscle |
| 427 | TCEAL1 | 2.6 | transcription elongation factor A (SII)-like 1 |
| 428 | GALNT12 | 2.6 | UDP-N-acetyl-alpha-D-galactosamine:polypeptide N-acetylgalactosaminyltransferase 12 (GalNAc-T12) |
| 429 | CCDC5 | 2.6 | coiled-coil domain containing 5 (spindle associated) |
| 430 | ITPR2 | 2.6 | inositol 1,4,5-triphosphate receptor, type 2 |
| 431 | LGALS8 | 2.6 | lectin, galactoside-binding, soluble, 8 (galectin 8) |
| 432 | GNB5 | 2.6 | guanine nucleotide binding protein (G protein), beta 5 |
| 433 | KBTBD11 | 2.5 | kelch repeat and BTB (POZ) domain containing 11 |
| 434 | ZDHHC4 | 2.5 | zinc finger, DHHC-type containing 4 |
| 435 | FREQ | 2.5 | frequenin homolog (*Drosophila*) |
| 436 | ETHE1 | 2.5 | ethylmalonic encephalopathy 1 |
| 437 | IGFBP2 | 2.5 | insulin-like growth factor binding protein 2, 36 kDa |
| 438 | CCDC4 | 2.5 | coiled-coil domain containing 4 |
| 439 | PYGL | 2.5 | phosphorylase, glycogen; liver (Hers disease, glycogen storage disease type VI) |
| 440 | TMEM38B | 2.5 | transmembrane protein 38B |
| 441 | THEM2 | 2.5 | thioesterase superfamily member 2 |
| 442 | HRH4 | 2.5 | histamine receptor H4 |
| 443 | C21orf96 | 2.5 | chromosome 21 open reading frame 96 |
| 444 | C11orf49 | 2.5 | chromosome 11 open reading frame 49 |
| 445 | EIF2C1 | 2.5 | eukaryotic translation initiation factor 2C, 1 |
| 446 | GLB1L3 | 2.5 | galactosidase, beta 1 like 3 |
| 447 | PAFAH1B3 | 2.5 | platelet-activating factor acetylhydrolase, isoform Ib, gamma subunit 29 kDa |
| 448 | PHF19 | 2.5 | PHD finger protein 19 |
| 449 | TBL1XR1 | 2.5 | transducin (beta)-like 1X-linked receptor 1 |
| 450 | SORD | 2.5 | sorbitol dehydrogenase |
| 451 | MND1 | 2.5 | meiotic nuclear divisions 1 homolog (*S. cerevisiae*) |
| 452 | MSRB2 | 2.5 | methionine sulfoxide reductase B2 |
| 453 | ZNF169 | 2.5 | zinc finger protein 169 |
| 454 | LANCL1 | 2.5 | LanC lantibiotic synthetase component C-like 1 (bacterial) |
| 455 | KLHL6 | 2.5 | kelch-like 6 (*Drosophila*) |
| 456 | MYO5A | 2.5 | myosin VA (heavy chain 12, myoxin) |
| 457 | RPS27L | 2.5 | ribosomal protein S27-like |
| 458 | LOC440288 | 2.5 | similar to FLJ16518 protein |
| 459 | IVNS1ABP | 2.5 | influenza virus NS1A binding protein |
| 460 | SLC39A4 | 2.5 | solute carrier family 39 (zinc transporter), member 4 |
| 461 | DMC1 | 2.5 | DMC1 dosage suppressor of mck1 homolog, meiosis-specific homologous recombination (yeast) |
| 462 | RAI14 | 2.5 | retinoic acid induced 14 |
| 463 | DPYSL2 | 2.5 | dihydropyrimidinase-like 2 |
| 464 | HEATR2 | 2.5 | HEAT repeat containing 2 |
| 465 | FSD1 | 2.5 | fibronectin type III and SPRY domain containing 1 |
| 466 | GCHFR | 2.5 | GTP cyclohydrolase I feedback regulator |
| 467 | ESD | 2.5 | esterase D/formylglutathione hydrolase |
| 468 | RAD54B | 2.5 | RAD54 homolog B (*S. cerevisiae*) |
| 469 | CPNE2 | 2.5 | copine II |
| 470 | ARHGEF12 | 2.5 | Rho guanine nucleotide exchange factor (GEF) 12 |
| 471 | RECK | 2.5 | reversion-inducing-cysteine-rich protein with kazal motifs |
| 472 | AK3L1 | 2.5 | adenylate kinase 3-like 1 |
| 473 | SGCB | 2.5 | sarcoglycan, beta (43 kDa dystrophin-associated glycoprotein) |
| 474 | COL6A2 | 2.5 | collagen, type VI, alpha 2 |
| 475 | RNASEH2A | 2.5 | ribonuclease H2, subunit A |
| 476 | CRTAP | 2.5 | cartilage associated protein |
| 477 | PRMT2 | 2.5 | protein arginine methyltransferase 2 |
| 478 | IFT81 | 2.5 | intraflagellar transport 81 homolog (*Chlamydomonas*) |
| 479 | SKAP2 | 2.5 | src kinase associated phosphoprotein 2 |
| 480 | NT5C3L | 2.5 | 5'-nucleotidase, cytosolic III-like |
| 481 | DIP2B | 2.5 | DIP2 disco-interacting protein 2 homolog B (*Drosophila*) |
| 482 | LOC730846 | 2.5 | similar to S-adenosylmethionine decarboxylase proenzyme 2 (AdoMetDC 2) (SamDC 2) |
| 483 | C4orf34 | 2.5 | chromosome 4 open reading frame 34 |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 484 | IKZF4 | 2.5 | IKAROS family zinc finger 4 (Eos) |
| 485 | COMT | 2.5 | catechol-O-methyltransferase |
| 486 | ECOP | 2.5 | EGFR-coamplified and overexpressed protein |
| 487 | KIAA1715 | 2.5 | KIAA1715 |
| 488 | RRAGC | 2.5 | Ras-related GTP binding C |
| 489 | C8orf70 | 2.5 | chromosome 8 open reading frame 70 |
| 490 | LRFN3 | 2.5 | leucine rich repeat and fibronectin type III domain containing 3 |
| 491 | LOC642236 | 2.5 | similar to FRG1 protein (FSHD region gene 1 protein) |
| 492 | ITGA3 | 2.4 | integrin, alpha 3 (antigen CD49C, alpha 3 subunit of VLA-3 receptor) |
| 493 | FVT1 | 2.4 | follicular lymphoma variant translocation 1 |
| 494 | HSPB1 | 2.4 | heat shock 27 kDa protein 1 |
| 495 | BMP2K | 2.4 | BMP2 inducible kinase |
| 496 | SNRPN | 2.4 | small nuclear ribonucleoprotein polypeptide N |
| 497 | TDRKH | 2.4 | tudor and KH domain containing |
| 498 | RAB7L1 | 2.4 | RAB7, member RAS oncogene family-like 1 |
| 499 | TEAD4 | 2.4 | TEA domain family member 4 |
| 500 | SERPINB6 | 2.4 | serpin peptidase inhibitor, clade B (ovalbumin), member 6 |
| 501 | GTF2A1 | 2.4 | general transcription factor IIA, 1, 19/37 kDa |
| 502 | CCDC15 | 2.4 | coiled-coil domain containing 15 |
| 503 | ALS2CR4 | 2.4 | amyotrophic lateral sclerosis 2 (juvenile) chromosome region, candidate 4 |
| 504 | DLG7 | 2.4 | discs, large homolog 7 (Drosophila) |
| 505 | ZSWIM7 | 2.4 | zinc finger, SWIM-type containing 7 |
| 506 | EHD3 | 2.4 | EH-domain containing 3 |
| 507 | ANG | 2.4 | angiogenin, ribonuclease, RNase A family, 5 |
| 508 | HSD17B6 | 2.4 | hydroxysteroid (17-beta) dehydrogenase 6 homolog (mouse) |
| 509 | CISD3 | 2.4 | CDGSH iron sulfur domain 3 |
| 510 | CBR4 | 2.4 | carbonyl reductase 4 |
| 511 | ORC5L | 2.4 | origin recognition complex, subunit 5-like (yeast) |
| 512 | POLR3G | 2.4 | polymerase (RNA) III (DNA directed) polypeptide G (32 kD) |
| 513 | LASP1 | 2.4 | LIM and SH3 protein 1 |
| 514 | XPNPEP3 | 2.4 | X-prolyl aminopeptidase (aminopeptidase P) 3, putative |
| 515 | NLRC3 | 2.4 | NLR family, CARD domain containing 3 |
| 516 | LOC133874 | 2.4 | hypothetical gene LOC133874 |
| 517 | TMEM173 | 2.4 | transmembrane protein 173 |
| 518 | COG6 | 2.4 | component of oligomeric golgi complex 6 |
| 519 | TNFSF13B | 2.4 | tumor necrosis factor (ligand) superfamily, member 13b |
| 520 | CUEDC2 | 2.4 | CUE domain containing 2 |
| 521 | PSD3 | 2.4 | pleckstrin and Sec7 domain containing 3 |
| 522 | SCRN1 | 2.4 | secernin 1 |
| 523 | SCOC | 2.4 | short coiled-coil protein |
| 524 | FAM45A | 2.4 | family with sequence similarity 45, member A |
| 525 | TOM1L1 | 2.4 | target of myb1 (chicken)-like 1 |
| 526 | PRIM2 | 2.4 | primase, DNA, polypeptide 2 (58 kDa) |
| 527 | SMTN | 2.4 | smoothelin |
| 528 | TMEM50B | 2.4 | transmembrane protein 50B |
| 529 | THEM5 | 2.4 | thioesterase superfamily member 5 |
| 530 | KIAA0146 | 2.4 | KIAA0146 |
| 531 | COMMD8 | 2.4 | COMM domain containing 8 |
| 532 | KIF20A | 2.4 | kinesin family member 20A |
| 533 | NEGR1 | 2.4 | neuronal growth regulator 1 |
| 534 | KLF7 | 2.4 | Kruppel-like factor 7 (ubiquitous) |
| 535 | C1orf93 | 2.4 | chromosome 1 open reading frame 93 |
| 536 | KCTD15 | 2.4 | potassium channel tetramerisation domain containing 15 |
| 537 | LACTB2 | 2.4 | lactamase, beta 2 |
| 538 | TCEA2 | 2.4 | transcription elongation factor A (SII), 2 |
| 539 | GLRX | 2.4 | glutaredoxin (thioltransferase) |
| 540 | KIAA1804 | 2.4 | mixed lineage kinase 4 |
| 541 | ATP2C1 | 2.4 | ATPase, Ca++ transporting, type 2C, member 1 |
| 542 | LOC339803 | 2.4 | hypothetical protein LOC339803 |
| 543 | NDUFA8 | 2.4 | NADH dehydrogenase (ubiquinone) 1 alpha subcomplex, 8, 19 kDa |
| 544 | ADA | 2.4 | adenosine deaminase |
| 545 | SLC25A4 | 2.4 | solute carrier family 25 (mitochondrial carrier; adenine nucleotide translocator), member 4 |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 546 | IDH1 | 2.4 | isocitrate dehydrogenase 1 (NADP+), soluble |
| 547 | TANC2 | 2.4 | tetratricopeptide repeat, ankyrin repeat and coiled-coil containing 2 |
| 548 | AGL | 2.4 | amylo-1, 6-glucosidase, 4-alpha-glucanotransferase (glycogen debranching enzyme, glycogen storage disease type III) |
| 549 | MAGED2 | 2.4 | melanoma antigen family D, 2 |
| 550 | JUB | 2.4 | jub, ajuba homolog (*Xenopus laevis*) |
| 551 | BCAT1 | 2.4 | branched chain aminotransferase 1, cytosolic |
| 552 | IRAK1BP1 | 2.4 | interleukin-1 receptor-associated kinase 1 binding protein 1 |
| 553 | RAB6IP1 | 2.4 | RAB6 interacting protein 1 |
| 554 | MOCS2 | 2.4 | molybdenum cofactor synthesis 2 |
| 555 | DMRT1 | 2.4 | doublesex and mab-3 related transcription factor 1 |
| 556 | HLA-DRB1 | 2.4 | major histocompatibility complex, class II, DR beta 1 |
| 557 | GLRX2 | 2.4 | glutaredoxin 2 |
| 558 | IL11 | 2.4 | interleukin 11 |
| 559 | FOXA1 | 2.4 | forkhead box A1 |
| 560 | SLC39A10 | 2.4 | solute carrier family 39 (zinc transporter), member 10 |
| 561 | SNX24 | 2.4 | sorting nexin 24 |
| 562 | NGFRAP1L1 | 2.4 | NGFRAP1-like 1 |
| 563 | C9orf64 | 2.4 | chromosome 9 open reading frame 64 |
| 564 | FAM82B | 2.4 | family with sequence similarity 82, member B |
| 565 | C1orf41 | 2.4 | chromosome 1 open reading frame 41 |
| 566 | TMED8 | 2.4 | transmembrane emp24 protein transport domain containing 8 |
| 567 | TLOC1 | 2.4 | translocation protein 1 |
| 568 | GPX1 | 2.4 | glutathione peroxidase 1 |
| 569 | GPR157 | 2.4 | G protein-coupled receptor 157 |
| 570 | MGC61571 | 2.4 | hypothetical protein MGC61571 |
| 571 | RNF14 | 2.4 | ring finger protein 14 |
| 572 | SLC41A1 | 2.4 | solute carrier family 41, member 1 |
| 573 | CAMSAP1L1 | 2.4 | calmodulin regulated spectrin-associated protein 1-like 1 |
| 574 | HS2ST1 | 2.4 | heparan sulfate 2-O-sulfotransferase 1 |
| 575 | SNX3 | 2.4 | sorting nexin 3 |
| 576 | STK39 | 2.3 | serine threonine kinase 39 (STE20/SPS1 homolog, yeast) |
| 577 | GRSF1 | 2.3 | G-rich RNA sequence binding factor 1 |
| 578 | TXNDC5 | 2.3 | thioredoxin domain containing 5 |
| 579 | PDLIM7 | 2.3 | PDZ and LIM domain 7 (enigma) |
| 580 | LOC730107 | 2.3 | similar to Glycine cleavage system H protein, mitochondrial precursor |
| 581 | PKP4 | 2.3 | plakophilin 4 |
| 582 | PHGDH | 2.3 | phosphoglycerate dehydrogenase |
| 583 | RASGRP4 | 2.3 | RAS guanyl releasing protein 4 |
| 584 | C3orf63 | 2.3 | chromosome 3 open reading frame 63 |
| 585 | MTX2 | 2.3 | metaxin 2 |
| 586 | CDC20 | 2.3 | cell division cycle 20 homolog (*S. cerevisiae*) |
| 587 | ATP6V1A | 2.3 | ATPase, H+ transporting, lysosomal 70 kDa, V1 subunit A |
| 588 | SCN3A | 2.3 | sodium channel, voltage-gated, type III, alpha subunit |
| 589 | MICALL1 | 2.3 | MICAL-like 1 |
| 590 | C1orf26 | 2.3 | chromosome 1 open reading frame 26 |
| 591 | ZCRB1 | 2.3 | zinc finger CCHC-type and RNA binding motif 1 |
| 592 | ATG4C | 2.3 | ATG4 autophagy related 4 homolog C (*S. cerevisiae*) |
| 593 | EIF2AK4 | 2.3 | eukaryotic translation initiation factor 2 alpha kinase 4 |
| 594 | FLJ32549 | 2.3 | hypothetical protein FLJ32549 |
| 595 | PPID | 2.3 | peptidylprolyl isomerase D (cyclophilin D) |
| 596 | SCCPDH | 2.3 | saccharopine dehydrogenase (putative) |
| 597 | ICMT | 2.3 | isoprenylcysteine carboxyl methyltransferase |
| 598 | CLIP1 | 2.3 | CAP-GLY domain containing linker protein 1 |
| 599 | ENY2 | 2.3 | enhancer of yellow 2 homolog (*Drosophila*) |
| 600 | RABL5 | 2.3 | RAB, member RAS oncogene family-like 5 |
| 601 | KIAA1430 | 2.3 | KIAA1430 |
| 602 | BCL6 | 2.3 | B-cell CLL/lymphoma 6 (zinc finger protein 51) |
| 603 | GBAS | 2.3 | glioblastoma amplified sequence |
| 604 | COQ3 | 2.3 | coenzyme Q3 homolog, methyltransferase (*S. cerevisiae*) |
| 605 | ATG10 | 2.3 | ATG10 autophagy related 10 homolog (*S. cerevisiae*) |
| 606 | KIAA1211 | 2.3 | KIAA1211 protein |
| 607 | SPA17 | 2.3 | sperm autoantigenic protein 17 |
| 608 | EIF2C4 | 2.3 | eukaryotic translation initiation factor 2C, 4 |
| 609 | PECI | 2.3 | peroxisomal D3,D2-enoyl-CoA isomerase |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 610 | JAKMIP2 | 2.3 | janus kinase and microtubule interacting protein 2 |
| 611 | HEBP1 | 2.3 | heme binding protein 1 |
| 612 | NCOA1 | 2.3 | nuclear receptor coactivator 1 |
| 613 | PHCA | 2.3 | phytoceramidase, alkaline |
| 614 | B3GNT1 | 2.3 | UDP-GlcNAc:betaGal beta-1,3-N-acetylglucosaminyltransferase 1 |
| 615 | FARS2 | 2.3 | phenylalanyl-tRNA synthetase 2, mitochondrial |
| 616 | CEBPD | 2.3 | CCAAT/enhancer binding protein (C/EBP), delta |
| 617 | ACBD5 | 2.3 | acyl-Coenzyme A binding domain containing 5 |
| 618 | AMZ2 | 2.3 | archaemetzincins-2 |
| 619 | DPH4 | 2.3 | DPH4, JJJ3 homolog (*S. cerevisiae*) |
| 620 | RAB32 | 2.3 | RAB32, member RAS oncogene family |
| 621 | WDFY3 | 2.3 | WD repeat and FYVE domain containing 3 |
| 622 | CCDC91 | 2.3 | coiled-coil domain containing 91 |
| 623 | ALDOC | 2.3 | aldolase C, fructose-bisphosphate |
| 624 | HADH | 2.3 | hydroxyacyl-Coenzyme A dehydrogenase |
| 625 | GTF2IRD1 | 2.3 | GTF2I repeat domain containing 1 |
| 626 | ATF3 | 2.3 | activating transcription factor 3 |
| 627 | CENTB1 | 2.3 | centaurin, beta 1 |
| 628 | ROR1 | 2.3 | receptor tyrosine kinase-like orphan receptor 1 |
| 629 | JHDM1D | 2.3 | jumonji C domain-containing histone demethylase 1 homolog D (*S. cerevisiae*) |
| 630 | STYXL1 | 2.3 | serine/threonine/tyrosine interacting-like 1 |
| 631 | SPAG16 | 2.3 | sperm associated antigen 16 |
| 632 | LOC153364 | 2.3 | similar to metallo-beta-lactamase superfamily protein |
| 633 | RPL23AP7 | 2.3 | ribosomal protein L23a pseudogene 7 |
| 634 | SEPT9 | 2.3 | septin 9 |
| 635 | HEBP2 | 2.3 | heme binding protein 2 |
| 636 | FAIM | 2.3 | Fas apoptotic inhibitory molecule |
| 637 | NUDT7 | 2.3 | nudix (nucleoside diphosphate linked moiety X)-type motif 7 |
| 638 | HSPA2 | 2.3 | heat shock 70 kDa protein 2 |
| 639 | ACSS2 | 2.3 | acyl-CoA synthetase short-chain family member 2 |
| 640 | PCTP | 2.3 | phosphatidylcholine transfer protein |
| 641 | SH3BP5 | 2.3 | SH3-domain binding protein 5 (BTK-associated) |
| 642 | ABCG1 | 2.3 | ATP-binding cassette, sub-family G (WHITE), member 1 |
| 643 | IHPK2 | 2.3 | inositol hexaphosphate kinase 2 |
| 644 | ZFYVE21 | 2.3 | zinc finger, FYVE domain containing 21 |
| 645 | PBK | 2.3 | PDZ binding kinase |
| 646 | BAX | 2.3 | BCL2-associated X protein |
| 647 | C4orf27 | 2.3 | chromosome 4 open reading frame 27 |
| 648 | C9orf46 | 2.3 | chromosome 9 open reading frame 46 |
| 649 | NMRAL1 | 2.3 | NmrA-like family domain containing 1 |
| 650 | NDUFB10 | 2.3 | NADH dehydrogenase (ubiquinone) 1 beta subcomplex, 10, 22 kDa |
| 651 | NT5DC2 | 2.3 | 5'-nucleotidase domain containing 2 |
| 652 | ZDHHC2 | 2.3 | zinc finger, DHHC-type containing 2 |
| 653 | MIF4GD | 2.3 | MIF4G domain containing |
| 654 | IMPDH2 | 2.2 | IMP (inosine monophosphate) dehydrogenase 2 |
| 655 | C1RL | 2.2 | complement component 1, r subcomponent-like |
| 656 | ALS2CR2 | 2.2 | amyotrophic lateral sclerosis 2 (juvenile) chromosome region, candidate 2 |
| 657 | VAV2 | 2.2 | vav 2 guanine nucleotide exchange factor |
| 658 | VPS8 | 2.2 | vacuolar protein sorting 8 homolog (*S. cerevisiae*) |
| 659 | NKIRAS1 | 2.2 | NFKB inhibitor interacting Ras-like 1 |
| 660 | ARL3 | 2.2 | ADP-ribosylation factor-like 3 |
| 661 | FAM129A | 2.2 | family with sequence similarity 129, member A |
| 662 | RPS6KA2 | 2.2 | ribosomal protein S6 kinase, 90 kDa, polypeptide 2 |
| 663 | RAB31 | 2.2 | RAB31, member RAS oncogene family |
| 664 | ADCK2 | 2.2 | aarF domain containing kinase 2 |
| 665 | GPD2 | 2.2 | glycerol-3-phosphate dehydrogenase 2 (mitochondrial) |
| 666 | TUBB6 | 2.2 | tubulin, beta 6 |
| 667 | PARVG | 2.2 | parvin, gamma |
| 668 | LRP10 | 2.2 | low density lipoprotein receptor-related protein 10 |
| 669 | MED25 | 2.2 | mediator complex subunit 25 |
| 670 | MVP | 2.2 | major vault protein |
| 671 | LCP2 | 2.2 | lymphocyte cytosolic protein 2 (SH2 domain containing leukocyte protein of 76 kDa) |
| 672 | C17orf75 | 2.2 | chromosome 17 open reading frame 75 |
| 673 | LIX1L | 2.2 | Lix1 homolog (mouse)-like |
| 674 | C3orf64 | 2.2 | chromosome 3 open reading frame 64 |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 675 | RCCD1 | 2.2 | RCC1 domain containing 1 |
| 676 | TMEM55A | 2.2 | transmembrane protein 55A |
| 677 | CPNE3 | 2.2 | copine III |
| 678 | FUNDC1 | 2.2 | FUN14 domain containing 1 |
| 679 | MAP3K9 | 2.2 | mitogen-activated protein kinase kinase kinase 9 |
| 680 | C5orf40 | 2.2 | chromosome 5 open reading frame 40 |
| 681 | CPT2 | 2.2 | carnitine palmitoyltransferase II |
| 682 | H1F0 | 2.2 | H1 histone family, member 0 |
| 683 | TADA3L | 2.2 | transcriptional adaptor 3 (NGG1 homolog, yeast)-like |
| 684 | HLA-DMB | 2.2 | major histocompatibility complex, class II, DM beta |
| 685 | DAPP1 | 2.2 | dual adaptor of phosphotyrosine and 3-phosphoinositides |
| 686 | HSD17B4 | 2.2 | hydroxysteroid (17-beta) dehydrogenase 4 |
| 687 | LGALS1 | 2.2 | lectin, galactoside-binding, soluble, 1 (galectin 1) |
| 688 | NARF | 2.2 | nuclear prelamin A recognition factor |
| 689 | ANKRA2 | 2.2 | ankyrin repeat, family A (RFXANK-like), 2 |
| 690 | SNX10 | 2.2 | sorting nexin 10 |
| 691 | TMCO3 | 2.2 | transmembrane and coiled-coil domains 3 |
| 692 | SLC22A4 | 2.2 | solute carrier family 22 (organic cation transporter), member 4 |
| 693 | CMTM7 | 2.2 | CKLF-like MARVEL transmembrane domain containing 7 |
| 694 | SGPP1 | 2.2 | sphingosine-1-phosphate phosphatase 1 |
| 695 | SV2A | 2.2 | synaptic vesicle glycoprotein 2A |
| 696 | SEC22C | 2.2 | SEC22 vesicle trafficking protein homolog C (*S. cerevisiae*) |
| 697 | ELMOD2 | 2.2 | ELMO/CED-12 domain containing 2 |
| 698 | FLJ35348 | 2.2 | FLJ35348 |
| 699 | RWDD3 | 2.2 | RWD domain containing 3 |
| 700 | TXNIP | 2.2 | thioredoxin interacting protein |
| 701 | GMPR2 | 2.2 | guanosine monophosphate reductase 2 |
| 702 | RPGRIP1L | 2.2 | RPGRIP1-like |
| 703 | EXOD1 | 2.2 | exonuclease domain containing 1 |
| 704 | RNF135 | 2.2 | ring finger protein 135 |
| 705 | FECH | 2.2 | ferrochelatase (protoporphyria) |
| 706 | COL6A1 | 2.2 | collagen, type VI, alpha 1 |
| 707 | C2orf28 | 2.2 | chromosome 2 open reading frame 28 |
| 708 | MTPN | 2.2 | myotrophin |
| 709 | TTC7A | 2.2 | tetratricopeptide repeat domain 7A |
| 710 | CPOX | 2.2 | coproporphyrinogen oxidase |
| 711 | SCAMP1 | 2.2 | secretory carrier membrane protein 1 |
| 712 | C11orf17 | 2.2 | chromosome 11 open reading frame 17 |
| 713 | FAM125A | 2.2 | family with sequence similarity 125, member A |
| 714 | FAM134B | 2.2 | family with sequence similarity 134, member B |
| 715 | LOC283551 | 2.2 | hypothetical protein LOC283551 |
| 716 | CA12 | 2.2 | carbonic anhydrase XII |
| 717 | ATPAF1 | 2.2 | ATP synthase mitochondrial F1 complex assembly factor 1 |
| 718 | TBC1D5 | 2.2 | TBC1 domain family, member 5 |
| 719 | CPNE8 | 2.2 | copine VIII |
| 720 | ADD2 | 2.2 | adducin 2 (beta) |
| 721 | FLJ43663 | 2.2 | hypothetical protein FLJ43663 |
| 722 | SLC1A4 | 2.2 | solute carrier family 1 (glutamate/neutral amino acid transporter), member 4 |
| 723 | MKL2 | 2.2 | MKL/myocardin-like 2 |
| 724 | MUM1 | 2.2 | melanoma associated antigen (mutated) 1 |
| 725 | FBXL16 | 2.2 | F-box and leucine-rich repeat protein 16 |
| 726 | LAPTM4B | 2.2 | lysosomal associated protein transmembrane 4 beta |
| 727 | HCFC1R1 | 2.2 | host cell factor C1 regulator 1 (XPO1 dependent) |
| 728 | CYFIP1 | 2.2 | cytoplasmic FMR1 interacting protein 1 |
| 729 | STXBP1 | 2.2 | syntaxin binding protein 1 |
| 730 | SLC25A12 | 2.2 | solute carrier family 25 (mitochondrial carrier, Aralar), member 12 |
| 731 | TPM1 | 2.2 | tropomyosin 1 (alpha) |
| 732 | PIGP | 2.2 | phosphatidylinositol glycan anchor biosynthesis, class P |
| 733 | PAWR | 2.2 | PRKC, apoptosis, WT1, regulator |
| 734 | CSK | 2.2 | c-src tyrosine kinase |
| 735 | HRSP12 | 2.2 | heat-responsive protein 12 |
| 736 | C20orf23 | 2.2 | chromosome 20 open reading frame 23 |
| 737 | GSTM4 | 2.2 | glutathione S-transferase M4 |
| 738 | ARL2 | 2.2 | ADP-ribosylation factor-like 2 |
| 739 | ADK | 2.2 | adenosine kinase |
| 740 | RABAC1 | 2.2 | Rab acceptor 1 (prenylated) |
| 741 | DEPDC1B | 2.2 | DEP domain containing 1B |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 742 | FSCN1 | 2.1 | fascin homolog 1, actin-bundling protein (*Strongylocentrotus purpuratus*) |
| 743 | IRF2BP2 | 2.1 | interferon regulatory factor 2 binding protein 2 |
| 744 | EIF4EBP1 | 2.1 | eukaryotic translation initiation factor 4E binding protein 1 |
| 745 | RFTN1 | 2.1 | raftlin, lipid raft linker 1 |
| 746 | C6orf32 | 2.1 | chromosome 6 open reading frame 32 |
| 747 | SAV1 | 2.1 | salvador homolog 1 (*Drosophila*) |
| 748 | RCBTB1 | 2.1 | regulator of chromosome condensation (RCC1) and BTB (POZ) domain containing protein 1 |
| 749 | AS3MT | 2.1 | arsenic (+3 oxidation state) methyltransferase |
| 750 | PROS1 | 2.1 | protein S (alpha) |
| 751 | LOC339804 | 2.1 | hypothetical gene supported by AK075484; BC014578 |
| 752 | ACADSB | 2.1 | acyl-Coenzyme A dehydrogenase, short/branched chain |
| 753 | PLAUR | 2.1 | plasminogen activator, urokinase receptor |
| 754 | HERC4 | 2.1 | hect domain and RLD 4 |
| 755 | SLAIN1 | 2.1 | SLAIN motif family, member 1 |
| 756 | C9orf119 | 2.1 | chromosome 9 open reading frame 119 |
| 757 | PAQR8 | 2.1 | progestin and adipoQ receptor family member VIII |
| 758 | DARS | 2.1 | aspartyl-tRNA synthetase |
| 759 | ANKRD22 | 2.1 | ankyrin repeat domain 22 |
| 760 | UROS | 2.1 | uroporphyrinogen III synthase (congenital erythropoietic porphyria) |
| 761 | TNRC6B | 2.1 | trinucleotide repeat containing 6B |
| 762 | NDRG3 | 2.1 | NDRG family member 3 |
| 763 | LYRM7 | 2.1 | Lyrm7 homolog (mouse) |
| 764 | TNFRSF25 | 2.1 | tumor necrosis factor receptor superfamily, member 25 |
| 765 | CNKSR3 | 2.1 | CNKSR family member 3 |
| 766 | INPP5F | 2.1 | inositol polyphosphate-5-phosphatase F |
| 767 | TNS1 | 2.1 | tensin 1 |
| 768 | TTC32 | 2.1 | tetratricopeptide repeat domain 32 |
| 769 | SAMD1 | 2.1 | sterile alpha motif domain containing 1 |
| 770 | ARHGAP5 | 2.1 | Rho GTPase activating protein 5 |
| 771 | MAP3K13 | 2.1 | mitogen-activated protein kinase kinase kinase 13 |
| 772 | PGM2 | 2.1 | phosphoglucomutase 2 |
| 773 | COX18 | 2.1 | COX18 cytochrome c oxidase assembly homolog (*S. cerevisiae*) |
| 774 | LOC339751 | 2.1 | hypothetical protein LOC339751 |
| 775 | BLVRB | 2.1 | biliverdin reductase B (flavin reductase (NADPH)) |
| 776 | CKB | 2.1 | creatine kinase, brain |
| 777 | PHKB | 2.1 | phosphorylase kinase, beta |
| 778 | M6PRBP1 | 2.1 | mannose-6-phosphate receptor binding protein 1 |
| 779 | SEC61A2 | 2.1 | Sec61 alpha 2 subunit (*S. cerevisiae*) |
| 780 | HMMR | 2.1 | hyaluronan-mediated motility receptor (RHAMM) |
| 781 | PPP1R7 | 2.1 | protein phosphatase 1, regulatory (inhibitor) subunit 7 |
| 782 | YIPF1 | 2.1 | Yip1 domain family, member 1 |
| 783 | PHF15 | 2.1 | PHD finger protein 15 |
| 784 | C6orf211 | 2.1 | chromosome 6 open reading frame 211 |
| 785 | OAT | 2.1 | ornithine aminotransferase (gyrate atrophy) |
| 786 | HLA-DRB5 | 2.1 | major histocompatibility complex, class II, DR beta 5 |
| 787 | DYNC1H1 | 2.1 | dynein, cytoplasmic 1, heavy chain 1 |
| 788 | ITGB3BP | 2.1 | integrin beta 3 binding protein (beta3-endonexin) |
| 789 | RABEPK | 2.1 | Rab9 effector protein with kelch motifs |
| 790 | LPIN1 | 2.1 | lipin 1 |
| 791 | F8 | 2.1 | coagulation factor VIII, procoagulant component (hemophilia A) |
| 792 | ARHGAP19 | 2.1 | Rho GTPase activating protein 19 |
| 793 | CCDC90A | 2.1 | coiled-coil domain containing 90A |
| 794 | AMMECR1 | 2.1 | Alport syndrome, mental retardation, midface hypoplasia and elliptocytosis chromosomal region, gene 1 |
| 795 | KIAA1279 | 2.1 | KIAA1279 |
| 796 | CRYZL1 | 2.1 | crystallin, zeta (quinone reductase)-like 1 |
| 797 | HNRNPU | 2.1 | heterogeneous nuclear ribonucleoprotein U (scaffold attachment factor A) |
| 798 | PRKAR2A | 2.1 | protein kinase, cAMP-dependent, regulatory, type II, alpha |
| 799 | CASK | 2.1 | calcium/calmodulin-dependent serine protein kinase (MAGUK family) |
| 800 | EFCAB4B | 2.1 | EF-hand calcium binding domain 4B |
| 801 | RDX | 2.1 | radixin |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 802 | BLR1 | 2.1 | Burkitt lymphoma receptor 1, GTP binding protein (chemokine (C—X—C motif) receptor 5) |
| 803 | TFEB | 2.1 | transcription factor EB |
| 804 | RTN4IP1 | 2.1 | reticulon 4 interacting protein 1 |
| 805 | C13orf21 | 2.1 | chromosome 13 open reading frame 21 |
| 806 | SCFD2 | 2.1 | sec1 family domain containing 2 |
| 807 | COG5 | 2.1 | component of oligomeric golgi complex 5 |
| 808 | TST | 2.1 | thiosulfate sulfurtransferase (rhodanese) |
| 809 | DNAJC13 | 2.1 | DnaJ (Hsp40) homolog, subfamily C, member 13 |
| 810 | CCNB2 | 2.1 | cyclin B2 |
| 811 | L1CAM | 2.1 | L1 cell adhesion molecule |
| 812 | DEF6 | 2.1 | differentially expressed in FDCP 6 homolog (mouse) |
| 813 | TNFRSF19 | 2.1 | tumor necrosis factor receptor superfamily, member 19 |
| 814 | PTPLA | 2.1 | protein tyrosine phosphatase-like (proline instead of catalytic arginine), member A |
| 815 | DGKI | 2.1 | diacylglycerol kinase, iota |
| 816 | SPIN4 | 2.1 | spindlin family, member 4 |
| 817 | GBE1 | 2.1 | glucan (1,4-alpha-), branching enzyme 1 (glycogen branching enzyme, Andersen disease, glycogen storage disease type IV) |
| 818 | PTPN12 | 2.1 | protein tyrosine phosphatase, non-receptor type 12 |
| 819 | CFDP1 | 2.1 | craniofacial development protein 1 |
| 820 | C14orf100 | 2.1 | chromosome 14 open reading frame 100 |
| 821 | SFN | 2.1 | stratifin |
| 822 | GCSH | 2.1 | glycine cleavage system protein H (aminomethyl carrier) |
| 823 | PTP4A2 | 2.1 | protein tyrosine phosphatase type IVA, member 2 |
| 824 | HMG20B | 2.1 | high-mobility group 20B |
| 825 | SMAD7 | 2.1 | SMAD family member 7 |
| 826 | ACYP1 | 2.1 | acylphosphatase 1, erythrocyte (common) type |
| 827 | HIBCH | 2.1 | 3-hydroxyisobutyryl-Coenzyme A hydrolase |
| 828 | ART3 | 2.1 | ADP-ribosyltransferase 3 |
| 829 | SH3YL1 | 2.1 | SH3 domain containing, Ysc84-like 1 (*S. cerevisiae*) |
| 830 | ADFP | 2.1 | adipose differentiation-related protein |
| 831 | HDAC9 | 2.1 | histone deacetylase 9 |
| 832 | CTTNBP2NL | 2.1 | CTTNBP2 N-terminal like |
| 833 | RNASEH2B | 2.1 | ribonuclease H2, subunit B |
| 834 | LCK | 2.1 | lymphocyte-specific protein tyrosine kinase |
| 835 | KCTD12 | 2.1 | potassium channel tetramerisation domain containing 12 |
| 836 | PCYOX1 | 2.1 | prenylcysteine oxidase 1 |
| 837 | TCEAL3 | 2.1 | transcription elongation factor A (SII)-like 3 |
| 838 | PAQR3 | 2.1 | progestin and adipoQ receptor family member III |
| 839 | TBC1D10C | 2.1 | TBC1 domain family, member 10C |
| 840 | SNX30 | 2.1 | sorting nexin family member 30 |
| 841 | PHKA1 | 2.1 | phosphorylase kinase, alpha 1 (muscle) |
| 842 | HLA-DRB4 | 2.1 | major histocompatibility complex, class II, DR beta 4 |
| 843 | GALNT6 | 2.1 | UDP-N-acetyl-alpha-D-galactosamine:polypeptide N-acetylgalactosaminyltransferase 6 (GalNAc-T6) |
| 844 | TCF12 | 2.1 | transcription factor 12 (HTF4, helix-loop-helix transcription factors 4) |
| 845 | CHST3 | 2.1 | carbohydrate (chondroitin 6) sulfotransferase 3 |
| 846 | TUBB3 | 2.1 | tubulin, beta 3 |
| 847 | AURKA | 2.1 | aurora kinase A |
| 848 | MAD2L2 | 2.1 | MAD2 mitotic arrest deficient-like 2 (yeast) |
| 849 | CTDSP2 | 2.1 | CTD (carboxy-terminal domain, RNA polymerase II, polypeptide A) small phosphatase 2 |
| 850 | COQ5 | 2.1 | coenzyme Q5 homolog, methyltransferase (*S. cerevisiae*) |
| 851 | FAM21C | 2.1 | family with sequence similarity 21, member C |
| 852 | C6orf57 | 2.1 | chromosome 6 open reading frame 57 |
| 853 | UNQ501 | 2.1 | MBC3205 |
| 854 | IL27RA | 2.1 | interleukin 27 receptor, alpha |
| 855 | KCTD3 | 2.1 | potassium channel tetramerisation domain containing 3 |
| 856 | DERA | 2.1 | 2-deoxyribose-5-phosphate aldolase homolog (*C. elegans*) |
| 857 | ANXA4 | 2.1 | annexin A4 |
| 858 | CCDC104 | 2.1 | coiled-coil domain containing 104 |
| 859 | VDR | 2.1 | vitamin D (1,25-dihydroxyvitamin D3) receptor |
| 860 | POMZP3 | 2.1 | POM (POM121 homolog, rat) and ZP3 fusion |
| 861 | PQLC3 | 2.1 | PQ loop repeat containing 3 |
| 862 | SCRN3 | 2.1 | secernin 3 |
| 863 | FZD7 | 2.1 | frizzled homolog 7 (*Drosophila*) |
| 864 | LOC145842 | 2.1 | hypothetical protein LOC145842 |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 865 | C11orf73 | 2.1 | chromosome 11 open reading frame 73 |
| 866 | C20orf19 | 2.1 | chromosome 20 open reading frame 19 |
| 867 | MORC4 | 2.1 | MORC family CW-type zinc finger 4 |
| 868 | NAGA | 2.1 | N-acetylgalactosaminidase, alpha- |
| 869 | APLP2 | 2.1 | amyloid beta (A4) precursor-like protein 2 |
| 870 | RHOQ | 2.1 | ras homolog gene family, member Q |
| 871 | BCS1L | 2.1 | BCS1-like (yeast) |
| 872 | C10orf4 | 2.1 | chromosome 10 open reading frame 4 |
| 873 | ADCY7 | 2.1 | adenylate cyclase 7 |
| 874 | FAM21A | 2.1 | family with sequence similarity 21, member A |
| 875 | CYB5B | 2.1 | cytochrome b5 type B (outer mitochondrial membrane) |
| 876 | TTC3 | 2.0 | tetratricopeptide repeat domain 3 |
| 877 | CCDC111 | 2.0 | coiled-coil domain containing 111 |
| 878 | ABHD14A | 2.0 | abhydrolase domain containing 14A |
| 879 | MAGED1 | 2.0 | melanoma antigen family D, 1 |
| 880 | MEN1 | 2.0 | multiple endocrine neoplasia I |
| 881 | MRPL40 | 2.0 | mitochondrial ribosomal protein L40 |
| 882 | CNOT6L | 2.0 | CCR4-NOT transcription complex, subunit 6-like |
| 883 | CCDC82 | 2.0 | coiled-coil domain containing 82 |
| 884 | FUT7 | 2.0 | fucosyltransferase 7 (alpha (1,3) fucosyltransferase) |
| 885 | NEK6 | 2.0 | NIMA (never in mitosis gene a)-related kinase 6 |
| 886 | PSIP1 | 2.0 | PC4 and SFRS1 interacting protein 1 |
| 887 | CDS1 | 2.0 | CDP-diacylglycerol synthase (phosphatidate cytidylyltransferase) 1 |
| 888 | MAPK9 | 2.0 | mitogen-activated protein kinase 9 |
| 889 | ZC3HAV1L | 2.0 | zinc finger CCCH-type, antiviral 1-like |
| 890 | TMEM19 | 2.0 | transmembrane protein 19 |
| 891 | JMJD2D | 2.0 | jumonji domain containing 2D |
| 892 | FOXP4 | 2.0 | forkhead box P4 |
| 893 | PFKM | 2.0 | phosphofructokinase, muscle |
| 894 | DNAJA4 | 2.0 | DnaJ (Hsp40) homolog, subfamily A, member 4 |
| 895 | MRPL39 | 2.0 | mitochondrial ribosomal protein L39 |
| 896 | XRCC4 | 2.0 | X-ray repair complementing defective repair in Chinese hamster cells 4 |
| 897 | IQCK | 2.0 | IQ motif containing K |
| 898 | SH3GLB1 | 2.0 | SH3-domain GRB2-like endophilin B1 |
| 899 | CCDC52 | 2.0 | coiled-coil domain containing 52 |
| 900 | YES1 | 2.0 | v-yes-1 Yamaguchi sarcoma viral oncogene homolog 1 |
| 901 | SLC37A1 | 2.0 | solute carrier family 37 (glycerol-3-phosphate transporter), member 1 |
| 902 | STK38L | 2.0 | serine/threonine kinase 38 like |
| 903 | SLC2A4RG | 2.0 | SLC2A4 regulator |
| 904 | DIAPH3 | 2.0 | diaphanous homolog 3 (*Drosophila*) |
| 905 | CERKL | 2.0 | ceramide kinase-like |
| 906 | MAF | 2.0 | v-maf musculoaponeurotic fibrosarcoma oncogene homolog (avian) |
| 907 | SNCA | 2.0 | synuclein, alpha (non A4 component of amyloid precursor) |
| 908 | KCNC4 | 2.0 | potassium voltage-gated channel, Shaw-related subfamily, member 4 |
| 909 | JAKMIP1 | 2.0 | janus kinase and microtubule interacting protein 1 |
| 910 | CISD2 | 2.0 | CDGSH iron sulfur domain 2 |
| 911 | CCDC90B | 2.0 | coiled-coil domain containing 90B |
| 912 | ING2 | 2.0 | inhibitor of growth family, member 2 |
| 913 | NPL | 2.0 | N-acetylneuraminate pyruvate lyase (dihydrodipicolinate synthase) |
| 914 | DNAJC10 | 2.0 | DnaJ (Hsp40) homolog, subfamily C, member 10 |
| 915 | TUBB2C | 2.0 | tubulin, beta 2C |
| 916 | CCNG1 | 2.0 | cyclin G1 |
| 917 | S100PBP | 2.0 | S100P binding protein |
| 918 | SCYL2 | 2.0 | SCY1-like 2 (*S. cerevisiae*) |
| 919 | MRPL43 | 2.0 | mitochondrial ribosomal protein L43 |
| 920 | TMEM106C | 2.0 | transmembrane protein 106C |
| 921 | SAT2 | 2.0 | spermidine/spermine N1-acetyltransferase 2 |
| 922 | TIGD2 | 2.0 | tigger transposable element derived 2 |
| 923 | UEVLD | 2.0 | UEV and lactate/malate dehydrogenase domains |
| 924 | NUBPL | 2.0 | nucleotide binding protein-like |
| 925 | GALC | 2.0 | galactosylceramidase |
| 926 | HMGA1 | 2.0 | high mobility group AT-hook 1 |
| 927 | CMAS | 2.0 | cytidine monophosphate N-acetylneuraminic acid synthetase |
| 928 | S100A11 | 2.0 | S100 calcium binding protein A11 |

TABLE 3-continued

Human genes that are up-regulated in Th17 conditions. Genes known to be up-regulated in the Th17 pathway are highlighted in bold as an indication of the validity of the data.

| order | gene name | fold change | description |
|---|---|---|---|
| 929 | CTSB | 2.0 | cathepsin B |
| 930 | ASCL1 | 2.0 | achaete-scute complex homolog 1 (*Drosophila*) |
| 931 | TNNT1 | 2.0 | troponin T type 1 (skeletal, slow) |
| 932 | COPG2 | 2.0 | coatomer protein complex, subunit gamma 2 |
| 933 | GKAP1 | 2.0 | G kinase anchoring protein 1 |
| 934 | USP13 | 2.0 | ubiquitin specific peptidase 13 (isopeptidase T-3) |
| 935 | SPTBN1 | 2.0 | spectrin, beta, non-erythrocytic 1 |
| 936 | MGST2 | 2.0 | microsomal glutathione S-transferase 2 |
| 937 | PEX1 | 2.0 | peroxisome biogenesis factor 1 |
| 938 | CPVL | 2.0 | carboxypeptidase, vitellogenic-like |
| 939 | LOC729604 | 2.0 | hypothetical protein LOC729604 |
| 940 | LOC26010 | 2.0 | viral DNA polymerase-transactivated protein 6 |
| 941 | ADAM19 | 2.0 | ADAM metallopeptidase domain 19 (meltrin beta) |
| 942 | SPAST | 2.0 | spastin |
| 943 | PLRG1 | 2.0 | pleiotropic regulator 1 (PRL1 homolog, *Arabidopsis*) |
| 944 | LOC647121 | 2.0 | similar to embigin homolog |
| 945 | CMTM3 | 2.0 | CKLF-like MARVEL transmembrane domain containing 3 |
| 946 | BUB1 | 2.0 | BUB1 budding uninhibited by benzimidazoles 1 homolog (yeast) |

TABLE 4

Human genes that are down-regulated in Th17 conditions. Genes known to be down-regulated in the Th17 pathway are highlighted in bold as an indication of the validity of the data.

| order | gene name | fold change | description |
|---|---|---|---|
| 1 | IL3 | −136.3 | interleukin 3 (colony-stimulating factor, multiple) |
| 2 | IL4 | −96.2 | interleukin 4 |
| 3 | INSM1 | −91.8 | insulinoma-associated 1 |
| 4 | CCL1 | −36.0 | chemokine (C—C motif) ligand 1 |
| 5 | SPP1 | −32.4 | secreted phosphoprotein 1 (osteopontin, bone sialoprotein I, early T-lymphocyte activation 1) |
| 6 | PTGER2 | −31.7 | prostaglandin E receptor 2 (subtype EP2), 53 kDa |
| 7 | TNFSF8 | −22.7 | tumor necrosis factor (ligand) superfamily, member 8 |
| 8 | CLECL1 | −21.9 | C-type lectin-like 1 |
| 9 | GATA3 | −21.8 | GATA binding protein 3 |
| 10 | NA | −20.9 | NA |
| 11 | XCL2 | −20.2 | chemokine (C motif) ligand 2 |
| 12 | XCL1 | −19.0 | chemokine (C motif) ligand 1 |
| 13 | SESN3 | −18.7 | sestrin 3 |
| 14 | PIP5K1B | −16.0 | phosphatidylinositol-4-phosphate 5-kinase, type I, beta |
| 15 | MEF2C | −14.7 | myocyte enhancer factor 2C |
| 16 | FOXP1 | −14.7 | forkhead box P1 |
| 17 | FGL2 | −13.0 | fibrinogen-like 2 |
| 18 | KBTBD7 | −12.7 | kelch repeat and BTB (POZ) domain containing 7 |
| 19 | KCNJ2 | −12.7 | potassium inwardly-rectifying channel, subfamily J, member 2 |
| 20 | TMEM46 | −12.6 | transmembrane protein 46 |
| 21 | AHI1 | −11.9 | Abelson helper integration site 1 |
| 22 | FGFBP2 | −11.6 | fibroblast growth factor binding protein 2 |
| 23 | TNIP3 | −11.2 | TNFAIP3 interacting protein 3 |
| 24 | CD38 | −11.2 | CD38 molecule |
| 25 | PDE7B | −11.0 | phosphodiesterase 7B |
| 26 | IL13 | −10.7 | interleukin 13 |
| 27 | MAP7 | −10.6 | microtubule-associated protein 7 |
| 28 | BACH2 | −10.6 | BTB and CNC homology 1, basic leucine zipper transcription factor 2 |
| 29 | CSF2 | −10.5 | colony stimulating factor 2 (granulocyte-macrophage) |
| 30 | IFNG | −10.3 | interferon, gamma |
| 31 | GBP5 | −10.3 | guanylate binding protein 5 |
| 32 | RHOBTB3 | −10.2 | Rho-related BTB domain containing 3 |
| 33 | GBP1 | −10.0 | guanylate binding protein 1, interferon-inducible, 67 kDa |
| 34 | PRSS23 | −9.3 | protease, serine, 23 |
| 35 | PLXNC1 | −9.3 | plexin C1 |

TABLE 4-continued

Human genes that are down-regulated in Th17 conditions. Genes known to be down-regulated in the Th17 pathway are highlighted in bold as an indication of the validity of the data.

| order | gene name | fold change | description |
|---|---|---|---|
| 36 | PTGS2 | −9.1 | prostaglandin-endoperoxide synthase 2 (prostaglandin G/H synthase and cyclooxygenase) |
| 37 | ZEB2 | −8.8 | zinc finger E-box binding homeobox 2 |
| 38 | CTHRC1 | −8.5 | collagen triple helix repeat containing 1 |
| 39 | APOL6 | −8.3 | apolipoprotein L, 6 |
| 40 | TAC1 | −8.1 | tachykinin, precursor 1 (substance K, substance P, neurokinin 1, neurokinin 2, neuromedin L, neurokinin alpha, neuropeptide K, neuropeptide gamma) |
| 41 | NRP1 | −7.9 | neuropilin 1 |
| 42 | RDH10 | −7.9 | retinol dehydrogenase 10 (all-trans) |
| 43 | GNG4 | −7.7 | guanine nucleotide binding protein (G protein), gamma 4 |
| 44 | COP1 | −7.4 | caspase-1 dominant-negative inhibitor pseudo-ICE |
| 45 | B3GNT5 | −7.4 | UDP-GlcNAc:betaGal beta-1,3-N-acetylglucosaminyltransferase 5 |
| 46 | CST7 | −7.3 | cystatin F (leukocystatin) |
| 47 | GLUD2 | −7.3 | glutamate dehydrogenase 2 |
| 48 | MCTP1 | −7.1 | multiple C2 domains, transmembrane 1 |
| 49 | ANXA1 | −7.0 | annexin A1 |
| 50 | TBCEL | −6.9 | tubulin folding cofactor E-like |
| 51 | CECR1 | −6.8 | cat eye syndrome chromosome region, candidate 1 |
| 52 | NIPA1 | −6.7 | non imprinted in Prader-Willi/Angelman syndrome 1 |
| 53 | FASLG | −6.4 | Fas ligand (TNF superfamily, member 6) |
| 54 | MGAT5 | −6.4 | mannosyl (alpha-1,6-)-glycoprotein beta-1,6-N-acetyl-glucosaminyltransferase |
| 55 | ACRC | −6.4 | acidic repeat containing |
| 56 | ARHGEF3 | −6.3 | Rho guanine nucleotide exchange factor (GEF) 3 |
| 57 | PMCH | −6.2 | pro-melanin-concentrating hormone |
| 58 | LPHN2 | −6.1 | latrophilin 2 |
| 59 | DPP4 | −6.0 | dipeptidyl-peptidase 4 (CD26, adenosine deaminase complexing protein 2) |
| 60 | FRY | −5.9 | furry homolog (*Drosophila*) |
| 61 | TA-NFKBH | −5.8 | T-cell activation NFKB-like protein |
| 62 | NFIL3 | −5.7 | nuclear factor, interleukin 3 regulated |
| 63 | GPR18 | −5.7 | G protein-coupled receptor 18 |
| 64 | WDFY1 | −5.7 | WD repeat and FYVE domain containing 1 |
| 65 | STAT4 | −5.7 | signal transducer and activator of transcription 4 |
| 66 | C1orf150 | −5.7 | chromosome 1 open reading frame 150 |
| 67 | TP53INP1 | −5.7 | tumor protein p53 inducible nuclear protein 1 |
| 68 | RCAN1 | −5.6 | regulator of calcineurin 1 |
| 69 | SRGN | −5.6 | serglycin |
| 70 | MTSS1 | −5.5 | metastasis suppressor 1 |
| 71 | NR4A2 | −5.5 | nuclear receptor subfamily 4, group A, member 2 |
| 72 | FAM84B | −5.4 | family with sequence similarity 84, member B |
| 73 | FAM107B | −5.4 | family with sequence similarity 107, member B |
| 74 | PLK2 | −5.4 | polo-like kinase 2 (*Drosophila*) |
| 75 | GBP2 | −5.4 | guanylate binding protein 2, interferon-inducible |
| 76 | ANK3 | −5.4 | ankyrin 3, node of Ranvier (ankyrin G) |
| 77 | EPSTI1 | −5.3 | epithelial stromal interaction 1 (breast) |
| 78 | ENPP2 | −5.3 | ectonucleotide pyrophosphatase/phosphodiesterase 2 (autotaxin) |
| 79 | SLC16A6 | −5.3 | solute carrier family 16, member 6 (monocarboxylic acid transporter 7) |
| 80 | GLUD1 | −5.2 | glutamate dehydrogenase 1 |
| 81 | SERPINB9 | −5.2 | serpin peptidase inhibitor, clade B (ovalbumin), member 9 |
| 82 | NPTX2 | −5.2 | neuronal pentraxin II |
| 83 | CCND1 | −5.1 | cyclin D1 |
| 84 | NINJ1 | −5.1 | ninjurin 1 |
| 85 | CBLB | −5.0 | Cas-Br-M (murine) ecotropic retroviral transforming sequence b |
| 86 | CD200 | −5.0 | CD200 molecule |
| 87 | CHML | −5.0 | choroideremia-like (Rab escort protein 2) |
| 88 | ZHX2 | −5.0 | zinc fingers and homeoboxes 2 |
| 89 | IL22 | −4.9 | interleukin 22 |
| 90 | FST | −4.9 | follistatin |
| 91 | NR4A3 | −4.9 | nuclear receptor subfamily 4, group A, member 3 |
| 92 | TNFSF11 | −4.8 | tumor necrosis factor (ligand) superfamily, member 11 |
| 93 | FYN | −4.8 | FYN oncogene related to SRC, FGR, YES |
| 94 | CCNYL1 | −4.7 | cyclin Y-like 1 |
| 95 | CXCR3 | −4.7 | chemokine (C—X—C motif) receptor 3 |
| 96 | RUNX2 | −4.6 | runt-related transcription factor 2 |
| 97 | BTLA | −4.6 | B and T lymphocyte associated |

TABLE 4-continued

Human genes that are down-regulated in Th17 conditions. Genes known to be down-regulated in the Th17 pathway are highlighted in bold as an indication of the validity of the data.

| order | gene name | fold change | description |
|---|---|---|---|
| 98 | CUGBP2 | −4.5 | CUG triplet repeat, RNA binding protein 2 |
| 99 | AGK | −4.5 | acylglycerol kinase |
| 100 | LOC650794 | −4.5 | similar to FRAS1-related extracellular matrix protein 2 precursor (ECM3 homolog) |
| 101 | IL18RAP | −4.5 | interleukin 18 receptor accessory protein |
| 102 | MARCKS | −4.4 | myristoylated alanine-rich protein kinase C substrate |
| 103 | PDE4D | −4.4 | phosphodiesterase 4D, cAMP-specific (phosphodiesterase E3 dunce homolog, *Drosophila*) |
| 104 | ANKRD10 | −4.4 | ankyrin repeat domain 10 |
| 105 | IL18R1 | −4.4 | interleukin 18 receptor 1 |
| 106 | TGFBR3 | −4.4 | transforming growth factor, beta receptor III |
| 107 | SNAG1 | −4.4 | sorting nexin associated golgi protein 1 |
| 108 | LRRN3 | −4.3 | leucine rich repeat neuronal 3 |
| 109 | AFF3 | −4.3 | AF4/FMR2 family, member 3 |
| 110 | AXIN2 | −4.3 | axin 2 (conductin, axil) |
| 111 | PMCHL1 | −4.3 | pro-melanin-concentrating hormone-like 1 |
| 112 | SGPP2 | −4.3 | sphingosine-1-phosphate phosphatase 2 |
| 113 | SMAD3 | −4.3 | SMAD family member 3 |
| 114 | ITGA9 | −4.2 | integrin, alpha 9 |
| 115 | ABCD3 | −4.2 | ATP-binding cassette, sub-family D (ALD), member 3 |
| 116 | MAL | −4.2 | mal, T-cell differentiation protein |
| 117 | IL10 | −4.2 | interleukin 10 |
| 118 | LOC360030 | −4.2 | homeobox C14 |
| 119 | GAD1 | −4.2 | glutamate decarboxylase 1 (brain, 67 kDa) |
| 120 | ZCCHC14 | −4.2 | zinc finger, CCHC domain containing 14 |
| 121 | LOC387763 | −4.1 | hypothetical LOC387763 |
| 122 | FOSB | −4.1 | FBJ murine osteosarcoma viral oncogene homolog B |
| 123 | BCL2L1 | −4.1 | BCL2-like 1 |
| 124 | SPAG1 | −4.1 | sperm associated antigen 1 |
| 125 | PHEX | −4.0 | phosphate regulating endopeptidase homolog, X-linked (hypophosphatemia, vitamin D resistant rickets) |
| 126 | TAGAP | −4.0 | T-cell activation GTPase activating protein |
| 127 | MTX3 | −4.0 | metaxin 3 |
| 128 | LAMP3 | −4.0 | lysosomal-associated membrane protein 3 |
| 129 | SMC5 | −4.0 | structural maintenance of chromosomes 5 |
| 130 | CD160 | −4.0 | CD160 molecule |
| 131 | PELI1 | −4.0 | pellino homolog 1 (*Drosophila*) |
| 132 | JAZF1 | −4.0 | JAZF zinc finger 1 |
| 133 | GBP3 | −4.0 | guanylate binding protein 3 |
| 134 | F3 | −4.0 | coagulation factor III (thromboplastin, tissue factor) |
| 135 | GEM | −4.0 | GTP binding protein overexpressed in skeletal muscle |
| 136 | RNF145 | −3.9 | ring finger protein 145 |
| 137 | PAM | −3.9 | peptidylglycine alpha-amidating monooxygenase |
| 138 | FAM122A | −3.9 | family with sequence similarity 122A |
| 139 | C6orf190 | −3.9 | chromosome 6 open reading frame 190 |
| 140 | SERAC1 | −3.9 | serine active site containing 1 |
| 141 | FLJ20273 | −3.9 | RNA-binding protein |
| 142 | LAG3 | −3.9 | lymphocyte-activation gene 3 |
| 143 | FAIM3 | −3.8 | Fas apoptotic inhibitory molecule 3 |
| 144 | TBL1X | −3.8 | transducin (beta)-like 1X-linked |
| 145 | BCL2L11 | −3.8 | BCL2-like 11 (apoptosis facilitator) |
| 146 | HS3ST3B1 | −3.8 | heparan sulfate (glucosamine) 3-O-sulfotransferase 3B1 |
| 147 | LOC151162 | −3.8 | hypothetical protein LOC151162 |
| 148 | ARL5B | −3.8 | ADP-ribosylation factor-like 5B |
| 149 | BCL2 | −3.8 | B-cell CLL/lymphoma 2 |
| 150 | HEG1 | −3.8 | HEG homolog 1 (zebrafish) |
| 151 | YPEL5 | −3.8 | yippee-like 5 (*Drosophila*) |
| 152 | FRMD4B | −3.8 | FERM domain containing 4B |
| 153 | PARP14 | −3.8 | poly (ADP-ribose) polymerase family, member 14 |
| 154 | POU2AF1 | −3.8 | POU class 2 associating factor 1 |
| 155 | CXorf6 | −3.8 | chromosome X open reading frame 6 |
| 156 | C13orf15 | −3.7 | chromosome 13 open reading frame 15 |
| 157 | NIN | −3.7 | ninein (GSK3B interacting protein) |
| 158 | ATXN1 | −3.7 | ataxin 1 |
| 159 | ATHL1 | −3.7 | ATH1, acid trehalase-like 1 (yeast) |
| 160 | CRIM1 | −3.7 | cysteine rich transmembrane BMP regulator 1 (chordin-like) |
| 161 | EGLN3 | −3.7 | egl nine homolog 3 (*C. elegans*) |
| 162 | LBH | −3.6 | limb bud and heart development homolog (mouse) |
| 163 | SEMA3D | −3.6 | sema domain, immunoglobulin domain (Ig), short basic domain, secreted, (semaphorin) 3D |
| 164 | MTUS1 | −3.6 | mitochondrial tumor suppressor 1 |

TABLE 4-continued

Human genes that are down-regulated in Th17 conditions. Genes known to be down-regulated in the Th17 pathway are highlighted in bold as an indication of the validity of the data.

| order | gene name | fold change | description |
|---|---|---|---|
| 165 | GNAI1 | −3.6 | guanine nucleotide binding protein (G protein), alpha inhibiting activity polypeptide 1 |
| 166 | PHLDA1 | −3.6 | pleckstrin homology-like domain, family A, member 1 |
| 167 | KLF12 | −3.6 | Kruppel-like factor 12 |
| 168 | PLA2G4A | −3.6 | phospholipase A2, group IVA (cytosolic, calcium-dependent) |
| 169 | DACH1 | −3.6 | dachshund homolog 1 (*Drosophila*) |
| 170 | CD247 | −3.5 | CD247 molecule |
| 171 | RP5-1022P6.2 | −3.5 | hypothetical protein KIAA1434 |
| 172 | MAPKAPK2 | −3.5 | mitogen-activated protein kinase-activated protein kinase 2 |
| 173 | ATP9A | −3.5 | ATPase, Class II, type 9A |
| 174 | KIAA1913 | −3.4 | KIAA1913 |
| 175 | PTPRJ | −3.4 | protein tyrosine phosphatase, receptor type, J |
| 176 | ANKRD13C | −3.4 | ankyrin repeat domain 13C |
| 177 | ANKH | −3.4 | ankylosis, progressive homolog (mouse) |
| 178 | APOBEC3B | −3.3 | apolipoprotein B mRNA editing enzyme, catalytic polypeptide-like 3B |
| 179 | SIPA1L1 | −3.3 | signal-induced proliferation-associated 1 like 1 |
| 180 | MGC39606 | −3.3 | hypothetical protein MGC39606 |
| 181 | C15orf5 | −3.3 | chromosome 15 open reading frame 5 |
| 182 | CCL4 | −3.3 | chemokine (C—C motif) ligand 4 |
| 183 | CD84 | −3.3 | CD84 molecule |
| 184 | CYR61 | −3.3 | cysteine-rich, angiogenic inducer, 61 |
| 185 | ZNF75 | −3.3 | zinc finger protein 75 (D8C6) |
| 186 | CDKN2C | −3.3 | cyclin-dependent kinase inhibitor 2C (p18, inhibits CDK4) |
| 187 | EGFL6 | −3.3 | EGF-like-domain, multiple 6 |
| 188 | NCALD | −3.3 | neurocalcin delta |
| 189 | MAP3K5 | −3.3 | mitogen-activated protein kinase kinase kinase 5 |
| 190 | TRIB2 | −3.3 | tribbles homolog 2 (*Drosophila*) |
| 191 | DLEU2 | −3.3 | deleted in lymphocytic leukemia, 2 |
| 192 | TRIB1 | −3.3 | tribbles homolog 1 (*Drosophila*) |
| 193 | FAM3C | −3.3 | family with sequence similarity 3, member C |
| 194 | REL | −3.3 | v-rel reticuloendotheliosis viral oncogene homolog (avian) |
| 195 | TRIM25 | −3.3 | tripartite motif-containing 25 |
| 196 | GJB6 | −3.2 | gap junction protein, beta 6 |
| 197 | PLEKHA7 | −3.2 | pleckstrin homology domain containing, family A member 7 |
| 198 | FLJ32810 | −3.2 | hypothetical protein FLJ32810 |
| 199 | PHF20L1 | −3.2 | PHD finger protein 20-like 1 |
| 200 | CYLD | −3.1 | cylindromatosis (turban tumor syndrome) |
| 201 | CPM | −3.1 | carboxypeptidase M |
| 202 | EDARADD | −3.1 | EDAR-associated death domain |
| 203 | SRGAP2 | −3.1 | SLIT-ROBO Rho GTPase activating protein 2 |
| 204 | FBXO30 | −3.1 | F-box protein 30 |
| 205 | PKIA | −3.1 | protein kinase (cAMP-dependent, catalytic) inhibitor alpha |
| 206 | G0S2 | −3.1 | G0/G1switch 2 |
| 207 | PRF1 | −3.1 | perforin 1 (pore forming protein) |
| 208 | MGC16121 | −3.1 | hypothetical protein MGC16121 |
| 209 | SRD5A2L | −3.1 | steroid 5 alpha-reductase 2-like |
| 210 | OSBPL3 | −3.1 | oxysterol binding protein-like 3 |
| 211 | OTUD4 | −3.1 | OTU domain containing 4 |
| 212 | IL1RN | −3.1 | interleukin 1 receptor antagonist |
| 213 | MB | −3.1 | myoglobin |
| 214 | UQCRC2 | −3.0 | ubiquinol-cytochrome c reductase core protein II |
| 215 | CAMK2D | −3.0 | calcium/calmodulin-dependent protein kinase (CaM kinase) II delta |
| 216 | DAPK1 | −3.0 | death-associated protein kinase 1 |
| 217 | KIAA0256 | −3.0 | KIAA0256 gene product |
| 218 | SETBP1 | −3.0 | SET binding protein 1 |
| 219 | ST8SIA4 | −3.0 | ST8 alpha-N-acetyl-neuraminide alpha-2,8-sialyltransferase 4 |
| 220 | IMAA | −3.0 | SLC7A5 pseudogene |
| 221 | CD52 | −3.0 | CD52 molecule |
| 222 | SLAMF6 | −3.0 | SLAM family member 6 |
| 223 | CTNNA1 | −3.0 | catenin (cadherin-associated protein), alpha 1, 102 kDa |
| 224 | C10orf54 | −3.0 | chromosome 10 open reading frame 54 |
| 225 | CASP7 | −2.9 | caspase 7, apoptosis-related cysteine peptidase |

TABLE 4-continued

Human genes that are down-regulated in Th17 conditions. Genes known to be down-regulated in the Th17 pathway are highlighted in bold as an indication of the validity of the data.

| order | gene name | fold change | description |
|---|---|---|---|
| 226 | HIVEP1 | −2.9 | human immunodeficiency virus type I enhancer binding protein 1 |
| 227 | HDGFRP3 | −2.9 | hepatoma-derived growth factor, related protein 3 |
| 228 | ELF1 | −2.9 | E74-like factor 1 (ets domain transcription factor) |
| 229 | STAT5A | −2.9 | signal transducer and activator of transcription 5A |
| 230 | BBS12 | −2.9 | Bardet-Biedl syndrome 12 |
| 231 | GTDC1 | −2.9 | glycosyltransferase-like domain containing 1 |
| 232 | CCDC41 | −2.9 | coiled-coil domain containing 41 |
| 233 | ARMCX3 | −2.9 | armadillo repeat containing, X-linked 3 |
| 234 | STARD4 | −2.9 | StAR-related lipid transfer (START) domain containing 4 |
| 235 | TSPAN2 | −2.9 | tetraspanin 2 |
| 236 | MDN1 | −2.9 | MDN1, midasin homolog (yeast) |
| 237 | IRAK2 | −2.8 | interleukin-1 receptor-associated kinase 2 |
| 238 | TGIF1 | −2.8 | TGFB-induced factor homeobox 1 |
| 239 | FLJ43663 | −2.8 | hypothetical protein FLJ43663 |
| 240 | SFXN1 | −2.8 | sideroflexin 1 |
| 241 | JMJD3 | −2.8 | jumonji domain containing 3 |
| 242 | APBB1IP | −2.8 | amyloid beta (A4) precursor protein-binding, family B, member 1 interacting protein |
| 243 | RERE | −2.8 | arginine-glutamic acid dipeptide (RE) repeats |
| 244 | TNFRSF9 | −2.8 | tumor necrosis factor receptor superfamily, member 9 |
| 245 | RFX2 | −2.8 | regulatory factor X, 2 (influences HLA class II expression) |
| 246 | SNX9 | −2.8 | sorting nexin 9 |
| 247 | CREM | −2.8 | cAMP responsive element modulator |
| 248 | SIAH2 | −2.8 | seven in absentia homolog 2 (*Drosophila*) |
| 249 | IKZF1 | −2.8 | IKAROS family zinc finger 1 (Ikaros) |
| 250 | HTR2B | −2.8 | 5-hydroxytryptamine (serotonin) receptor 2B |
| 251 | SQLE | −2.8 | squalene epoxidase |
| 252 | GIMAP7 | −2.7 | GTPase, IMAP family member 7 |
| 253 | C21orf71 | −2.7 | chromosome 21 open reading frame 71 |
| 254 | RPS6KA3 | −2.7 | ribosomal protein S6 kinase, 90 kDa, polypeptide 3 |
| 255 | SYNE2 | −2.7 | spectrin repeat containing, nuclear envelope 2 |
| 256 | CSF1 | −2.7 | colony stimulating factor 1 (macrophage) |
| 257 | MBNL2 | −2.7 | muscleblind-like 2 (*Drosophila*) |
| 258 | PBEF1 | −2.7 | pre-B-cell colony enhancing factor 1 |
| 259 | FLJ10038 | −2.7 | hypothetical protein FLJ10038 |
| 260 | LAIR2 | −2.7 | leukocyte-associated immunoglobulin-like receptor 2 |
| 261 | ARHGEF7 | −2.7 | Rho guanine nucleotide exchange factor (GEF) 7 |
| 262 | XIRP1 | −2.7 | xin actin-binding repeat containing 1 |
| 263 | LOC729697 | −2.7 | hypothetical protein LOC729697 |
| 264 | OGT | −2.7 | O-linked N-acetylglucosamine (GlcNAc) transferase (UDP-N-acetylglucosamine:polypeptide-N-acetylglucosaminyl transferase) |
| 265 | RBM33 | −2.7 | RNA binding motif protein 33 |
| 266 | STK4 | −2.7 | serine/threonine kinase 4 |
| 267 | SOS1 | −2.7 | son of sevenless homolog 1 (*Drosophila*) |
| 268 | AMIGO2 | −2.7 | adhesion molecule with Ig-like domain 2 |
| 269 | CD99 | −2.7 | CD99 molecule |
| 270 | STAP1 | −2.7 | signal transducing adaptor family member 1 |
| 271 | JARID2 | −2.7 | jumonji, AT rich interactive domain 2 |
| 272 | KIAA1546 | −2.7 | KIAA1546 |
| 273 | RPUSD4 | −2.7 | RNA pseudouridylate synthase domain containing 4 |
| 274 | IL21 | −2.7 | interleukin 21 |
| 275 | SAMD9 | −2.6 | sterile alpha motif domain containing 9 |
| 276 | FN1 | −2.6 | fibronectin 1 |
| 277 | SYTL3 | −2.6 | synaptotagmin-like 3 |
| 278 | RAB38 | −2.6 | RAB38, member RAS oncogene family |
| 279 | DUSP5 | −2.6 | dual specificity phosphatase 5 |
| 280 | SORBS1 | −2.6 | sorbin and SH3 domain containing 1 |
| 281 | SHC4 | −2.6 | SHC (Src homology 2 domain containing) family, member 4 |
| 282 | ING3 | −2.6 | inhibitor of growth family, member 3 |
| 283 | KLF4 | −2.6 | Kruppel-like factor 4 (gut) |
| 284 | PRKCH | −2.6 | protein kinase C, eta |
| 285 | C20orf82 | −2.6 | chromosome 20 open reading frame 82 |
| 286 | ZC3H12C | −2.6 | zinc finger CCCH-type containing 12C |
| 287 | IGF2BP3 | −2.6 | insulin-like growth factor 2 mRNA binding protein 3 |
| 288 | SAMD4A | −2.6 | sterile alpha motif domain containing 4A |
| 289 | MYLIP | −2.6 | myosin regulatory light chain interacting protein |
| 290 | OPA1 | −2.6 | optic atrophy 1 (autosomal dominant) |

TABLE 4-continued

Human genes that are down-regulated in Th17 conditions. Genes known to be down-regulated in the Th17 pathway are highlighted in bold as an indication of the validity of the data.

| order | gene name | fold change | description |
|---|---|---|---|
| 291 | TRPM6 | −2.6 | transient receptor potential cation channel, subfamily M, member 6 |
| 292 | PTPRK | −2.5 | protein tyrosine phosphatase, receptor type, K |
| 293 | GABPB2 | −2.5 | GA binding protein transcription factor, beta subunit 2 |
| 294 | FOS | −2.5 | v-fos FBJ murine osteosarcoma viral oncogene homolog |
| 295 | SOX8 | −2.5 | SRY (sex determining region Y)-box 8 |
| 296 | BIRC3 | −2.5 | baculoviral IAP repeat-containing 3 |
| 297 | CCDC64 | −2.5 | coiled-coil domain containing 64 |
| 298 | HPSE | −2.5 | heparanase |
| 299 | DENND4A | −2.5 | DENN/MADD domain containing 4A |
| 300 | RUNX3 | −2.5 | runt-related transcription factor 3 |
| 301 | LOC645431 | −2.5 | hypothetical protein LOC645431 |
| 302 | CTNS | −2.5 | cystinosis, nephropathic |
| 303 | GPR81 | −2.5 | G protein-coupled receptor 81 |
| 304 | ATP1B3 | −2.5 | ATPase, Na+/K+ transporting, beta 3 polypeptide |
| 305 | MAPK1 | −2.5 | mitogen-activated protein kinase 1 |
| 306 | TNFRSF4 | −2.5 | tumor necrosis factor receptor superfamily, member 4 |
| 307 | PDE3B | −2.5 | phosphodiesterase 3B, cGMP-inhibited |
| 308 | STT3B | −2.5 | STT3, subunit of the oligosaccharyltransferase complex, homolog B (S. cerevisiae) |
| 309 | TP53BP2 | −2.5 | tumor protein p53 binding protein, 2 |
| 310 | SPRY1 | −2.5 | sprouty homolog 1, antagonist of FGF signaling (Drosophila) |
| 311 | EIF4ENIF1 | −2.5 | eukaryotic translation initiation factor 4E nuclear import factor 1 |
| 312 | TLE4 | −2.5 | transducin-like enhancer of split 4 (E(sp1) homolog, Drosophila) |
| 313 | TRAF5 | −2.5 | TNF receptor-associated factor 5 |
| 314 | IFNAR2 | −2.5 | interferon (alpha, beta and omega) receptor 2 |
| 315 | ITPR1 | −2.5 | inositol 1,4,5-triphosphate receptor, type 1 |
| 316 | KIAA1217 | −2.4 | KIAA1217 |
| 317 | GZMA | −2.4 | granzyme A (granzyme 1, cytotoxic T-lymphocyte-associated serine esterase 3) |
| 318 | CD27 | −2.4 | CD27 molecule |
| 319 | PDXDC1 | −2.4 | pyridoxal-dependent decarboxylase domain containing 1 |
| 320 | SFRS11 | −2.4 | splicing factor, arginine/serine-rich 11 |
| 321 | BRAF | −2.4 | v-raf murine sarcoma viral oncogene homolog B1 |
| 322 | CD80 | −2.4 | CD80 molecule |
| 323 | VPS37B | −2.4 | vacuolar protein sorting 37 homolog B (S. cerevisiae) |
| 324 | FNBP1 | −2.4 | formin binding protein 1 |
| 325 | FAM113B | −2.4 | family with sequence similarity 113, member B |
| 326 | FAM62B | −2.4 | family with sequence similarity 62 (C2 domain containing) member B |
| 327 | GPR56 | −2.4 | G protein-coupled receptor 56 |
| 328 | ITGB1 | −2.4 | integrin, beta 1 (fibronectin receptor, beta polypeptide, antigen CD29 includes MDF2, MSK12) |
| 329 | MLSTD1 | −2.4 | male sterility domain containing 1 |
| 330 | EGR3 | −2.4 | early growth response 3 |
| 331 | MITF | −2.4 | microphthalmia-associated transcription factor |
| 332 | SEC61B | −2.4 | Sec61 beta subunit |
| 333 | PPP4R2 | −2.4 | protein phosphatase 4, regulatory subunit 2 |
| 334 | BCL10 | −2.4 | B-cell CLL/lymphoma 10 |
| 335 | SIPA1L2 | −2.4 | signal-induced proliferation-associated 1 like 2 |
| 336 | KIAA0182 | −2.4 | KIAA0182 |
| 337 | USP12 | −2.4 | ubiquitin specific peptidase 12 |
| 338 | RNF19A | −2.4 | ring finger protein 19A |
| 339 | MAPRE2 | −2.4 | microtubule-associated protein, RP/EB family, member 2 |
| 340 | DKFZp547E087 | −2.4 | hypothetical gene LOC283846 |
| 341 | TSPAN5 | −2.4 | tetraspanin 5 |
| 342 | SNF1LK2 | −2.4 | SNF1-like kinase 2 |
| 343 | MEF2A | −2.3 | myocyte enhancer factor 2A |
| 344 | EGR4 | −2.3 | early growth response 4 |
| 345 | HSD17B12 | −2.3 | hydroxysteroid (17-beta) dehydrogenase 12 |
| 346 | C3orf26 | −2.3 | chromosome 3 open reading frame 26 |
| 347 | SERPINE2 | −2.3 | serpin peptidase inhibitor, clade E (nexin, plasminogen activator inhibitor type 1), member 2 |
| 348 | C10orf18 | −2.3 | chromosome 10 open reading frame 18 |
| 349 | FMNL2 | −2.3 | formin-like 2 |
| 350 | CHSY1 | −2.3 | carbohydrate (chondroitin) synthase 1 |
| 351 | DLEU2L | −2.3 | deleted in lymphocytic leukemia 2-like |

TABLE 4-continued

Human genes that are down-regulated in Th17 conditions. Genes known to be down-regulated in the Th17 pathway are highlighted in bold as an indication of the validity of the data.

| order | gene name | fold change | description |
|---|---|---|---|
| 352 | LOC145474 | −2.3 | hypothetical protein LOC145474 |
| 353 | IGF2R | −2.3 | insulin-like growth factor 2 receptor |
| 354 | GVIN1 | −2.3 | GTPase, very large interferon inducible 1 |
| 355 | HOMER2 | −2.3 | homer homolog 2 (*Drosophila*) |
| 356 | ZNF432 | −2.3 | zinc finger protein 432 |
| 357 | IL6ST | −2.3 | interleukin 6 signal transducer (gp130, oncostatin M receptor) |
| 358 | CLEC2D | −2.3 | C-type lectin domain family 2, member D |
| 359 | JAK2 | −2.3 | Janus kinase 2 (a protein tyrosine kinase) |
| 360 | CUGBP1 | −2.3 | CUG triplet repeat, RNA binding protein 1 |
| 361 | OPN3 | −2.3 | opsin 3 (encephalopsin, panopsin) |
| 362 | CRTAM | −2.3 | cytotoxic and regulatory T cell molecule |
| 363 | LYST | −2.3 | lysosomal trafficking regulator |
| 364 | SLC5A3 | −2.3 | solute carrier family 5 (inositol transporters), member 3 |
| 365 | ANKRD28 | −2.3 | ankyrin repeat domain 28 |
| 366 | ATP13A3 | −2.3 | ATPase type 13A3 |
| 367 | EIF3C | −2.3 | eukaryotic translation initiation factor 3, subunit C |
| 368 | TNFRSF18 | −2.3 | tumor necrosis factor receptor superfamily, member 18 |
| 369 | REV3L | −2.3 | REV3-like, catalytic subunit of DNA polymerase zeta (yeast) |
| 370 | RYBP | −2.3 | RING1 and YY1 binding protein |
| 371 | FHIT | −2.3 | fragile histidine triad gene |
| 372 | HNRPH1 | −2.3 | heterogeneous nuclear ribonucleoprotein H1 (H) |
| 373 | ENC1 | −2.3 | ectodermal-neural cortex (with BTB-like domain) |
| 374 | C16orf45 | −2.3 | chromosome 16 open reading frame 45 |
| 375 | STAT5B | −2.3 | signal transducer and activator of transcription 5B |
| 376 | KIAA1267 | −2.3 | KIAA1267 |
| 377 | SDC4 | −2.3 | syndecan 4 |
| 378 | ITGB7 | −2.3 | integrin, beta 7 |
| 379 | PTEN | −2.3 | phosphatase and tensin homolog (mutated in multiple advanced cancers 1) |
| 380 | BCLAF1 | −2.3 | BCL2-associated transcription factor 1 |
| 381 | CD47 | −2.3 | CD47 molecule |
| 382 | P2RY5 | −2.3 | purinergic receptor P2Y, G-protein coupled, 5 |
| 383 | MRPS6 | −2.2 | mitochondrial ribosomal protein S6 |
| 384 | ETS1 | −2.2 | v-ets erythroblastosis virus E26 oncogene homolog 1 (avian) |
| 385 | IL1R1 | −2.2 | interleukin 1 receptor, type I |
| 386 | LRRFIP1 | −2.2 | leucine rich repeat (in FLII) interacting protein 1 |
| 387 | C9orf3 | −2.2 | chromosome 9 open reading frame 3 |
| 388 | RREB1 | −2.2 | ras responsive element binding protein 1 |
| 389 | C7orf30 | −2.2 | chromosome 7 open reading frame 30 |
| 390 | HMGCS1 | −2.2 | 3-hydroxy-3-methylglutaryl-Coenzyme A synthase 1 (soluble) |
| 391 | PTPRC | −2.2 | protein tyrosine phosphatase, receptor type, C |
| 392 | RLF | −2.2 | rearranged L-myc fusion |
| 393 | CDC14A | −2.2 | CDC14 cell division cycle 14 homolog A (*S. cerevisiae*) |
| 394 | ADAT2 | −2.2 | adenosine deaminase, tRNA-specific 2, TAD2 homolog (*S. cerevisiae*) |
| 395 | NOL10 | −2.2 | nucleolar protein 10 |
| 396 | TIAM1 | −2.2 | T-cell lymphoma invasion and metastasis 1 |
| 397 | CD96 | −2.2 | CD96 molecule |
| 398 | SNTB2 | −2.2 | syntrophin, beta 2 (dystrophin-associated protein A1, 59 kDa, basic component 2) |
| 399 | PRKX | −2.2 | protein kinase, X-linked |
| 400 | DPYD | −2.2 | dihydropyrimidine dehydrogenase |
| 401 | PIK3R1 | −2.2 | phosphoinositide-3-kinase, regulatory subunit 1 (p85 alpha) |
| 402 | LOC23117 | −2.2 | KIAA0220-like protein |
| 403 | DLG1 | −2.2 | discs, large homolog 1 (*Drosophila*) |
| 404 | TM2D3 | −2.2 | TM2 domain containing 3 |
| 405 | HEATR1 | −2.2 | HEAT repeat containing 1 |
| 406 | CEACAM21 | −2.2 | carcinoembryonic antigen-related cell adhesion molecule 21 |
| 407 | SLC8A1 | −2.2 | solute carrier family 8 (sodium/calcium exchanger), member 1 |
| 408 | NR4A1 | −2.2 | nuclear receptor subfamily 4, group A, member 1 |
| 409 | SRP54 | −2.2 | signal recognition particle 54 kDa |
| 410 | TULP4 | −2.2 | tubby like protein 4 |
| 411 | ZFP36L1 | −2.2 | zinc finger protein 36, C3H type-like 1 |
| 412 | C20orf74 | −2.2 | chromosome 20 open reading frame 74 |
| 413 | CENTD1 | −2.2 | centaurin, delta 1 |

TABLE 4-continued

Human genes that are down-regulated in Th17 conditions. Genes known to be down-regulated in the Th17 pathway are highlighted in bold as an indication of the validity of the data.

| order | gene name | fold change | description |
|---|---|---|---|
| 414 | NSUN4 | −2.2 | NOL1/NOP2/Sun domain family, member 4 |
| 415 | AZIN1 | −2.2 | antizyme inhibitor 1 |
| 416 | PCSK6 | −2.2 | proprotein convertase subtilisin/kexin type 6 |
| 417 | PDS5A | −2.2 | PDS5, regulator of cohesion maintenance, homolog A (*S. cerevisiae*) |
| 418 | DDHD1 | −2.2 | DDHD domain containing 1 |
| 419 | LTV1 | −2.2 | LTV1 homolog (*S. cerevisiae*) |
| 420 | KIF1B | −2.2 | kinesin family member 1B |
| 421 | EFNB2 | −2.2 | ephrin-B2 |
| 422 | HBP1 | −2.2 | HMG-box transcription factor 1 |
| 423 | SLTM | −2.2 | SAFB-like, transcription modulator |
| 424 | TMEM88 | −2.2 | transmembrane protein 88 |
| 425 | PHACTR2 | −2.2 | phosphatase and actin regulator 2 |
| 426 | SPATA13 | −2.2 | spermatogenesis associated 13 |
| 427 | NHS | −2.2 | Nance-Horan syndrome (congenital cataracts and dental anomalies) |
| 428 | FOXN3 | −2.2 | forkhead box N3 |
| 429 | EOMES | −2.2 | eomesodermin homolog (*Xenopus laevis*) |
| 430 | WNK1 | −2.2 | WNK lysine deficient protein kinase 1 |
| 431 | HS3ST1 | −2.2 | heparan sulfate (glucosamine) 3-O-sulfotransferase 1 |
| 432 | SBF2 | −2.2 | SET binding factor 2 |
| 433 | TWIST1 | −2.2 | twist homolog 1 (acrocephalosyndactyly 3; Saethre-Chotzen syndrome) (*Drosophila*) |
| 434 | RASGRF2 | −2.2 | Ras protein-specific guanine nucleotide-releasing factor 2 |
| 435 | ATF6 | −2.2 | activating transcription factor 6 |
| 436 | SF1 | −2.2 | splicing factor 1 |
| 437 | TMEM133 | −2.2 | transmembrane protein 133 |
| 438 | CABIN1 | −2.2 | calcineurin binding protein 1 |
| 439 | CHST11 | −2.2 | carbohydrate (chondroitin 4) sulfotransferase 11 |
| 440 | LGALS3BP | −2.2 | lectin, galactoside-binding, soluble, 3 binding protein |
| 441 | ZNF419 | −2.2 | zinc finger protein 419 |
| 442 | CNOT2 | −2.1 | CCR4-NOT transcription complex, subunit 2 |
| 443 | LOC643187 | −2.1 | similar to ankyrin repeat domain 20A |
| 444 | PRKCB1 | −2.1 | protein kinase C, beta 1 |
| 445 | KBTBD6 | −2.1 | kelch repeat and BTB (POZ) domain containing 6 |
| 446 | POLR3C | −2.1 | polymerase (RNA) III (DNA directed) polypeptide C (62 kD) |
| 447 | C4orf32 | −2.1 | chromosome 4 open reading frame 32 |
| 448 | TRIM13 | −2.1 | tripartite motif-containing 13 |
| 449 | TMEM165 | −2.1 | transmembrane protein 165 |
| 450 | C1orf104 | −2.1 | chromosome 1 open reading frame 104 |
| 451 | FOSL2 | −2.1 | FOS-like antigen 2 |
| 452 | LOC650392 | −2.1 | hypothetical protein LOC650392 |
| 453 | PQLC1 | −2.1 | PQ loop repeat containing 1 |
| 454 | PLCL1 | −2.1 | phospholipase C-like 1 |
| 455 | WTAP | −2.1 | Wilms tumor 1 associated protein |
| 456 | SMU1 | −2.1 | smu-1 suppressor of mec-8 and unc-52 homolog (*C. elegans*) |
| 457 | KCNQ5 | −2.1 | potassium voltage-gated channel, KQT-like subfamily, member 5 |
| 458 | ANP32A | −2.1 | acidic (leucine-rich) nuclear phosphoprotein 32 family, member A |
| 459 | MUC20 | −2.1 | mucin 20, cell surface associated |
| 460 | LOC152485 | −2.1 | hypothetical protein LOC152485 |
| 461 | NETO1 | −2.1 | neuropilin (NRP) and tolloid (TLL)-like 1 |
| 462 | LOC440345 | −2.1 | hypothetical protein LOC440345 |
| 463 | ZNF567 | −2.1 | zinc finger protein 567 |
| 464 | SUV420H1 | −2.1 | suppressor of variegation 4-20 homolog 1 (*Drosophila*) |
| 465 | MGC7036 | −2.1 | hypothetical protein MGC7036 |
| 466 | WIPI1 | −2.1 | WD repeat domain, phosphoinositide interacting 1 |
| 467 | PER1 | −2.1 | period homolog 1 (*Drosophila*) |
| 468 | TNFRSF21 | −2.1 | tumor necrosis factor receptor superfamily, member 21 |
| 469 | RBM25 | −2.1 | RNA binding motif protein 25 |
| 470 | EIF2C2 | −2.1 | eukaryotic translation initiation factor 2C, 2 |
| 471 | NPAS3 | −2.1 | neuronal PAS domain protein 3 |
| 472 | KIAA0922 | −2.1 | KIAA0922 |
| 473 | TRIM6 | −2.1 | tripartite motif-containing 6 |
| 474 | LOC440993 | −2.1 | hypothetical gene supported by AK128346 |
| 475 | PIM3 | −2.1 | pim-3 oncogene |
| 476 | MBNL1 | −2.1 | muscleblind-like (*Drosophila*) |

TABLE 4-continued

Human genes that are down-regulated in Th17 conditions. Genes known to be down-regulated in the Th17 pathway are highlighted in bold as an indication of the validity of the data.

| order | gene name | fold change | description |
|---|---|---|---|
| 477 | LOC730092 | −2.1 | RRN3 RNA polymerase I transcription factor homolog (S. cerevisiae) pseudogene |
| 478 | CYSLTR1 | −2.1 | cysteinyl leukotriene receptor 1 |
| 479 | RAB8B | −2.1 | RAB8B, member RAS oncogene family |
| 480 | UBE2F | −2.1 | ubiquitin-conjugating enzyme E2F (putative) |
| 481 | PRDM1 | −2.1 | PR domain containing 1, with ZNF domain |
| 482 | ADK | −2.1 | adenosine kinase |
| 483 | LOC727738 | −2.1 | similar to Amphiregulin precursor (AR) (Colorectum cell-derived growth factor) (CRDGF) |
| 484 | PEX3 | −2.1 | peroxisomal biogenesis factor 3 |
| 485 | CD55 | −2.1 | CD55 molecule, decay accelerating factor for complement (Cromer blood group) |
| 486 | AUTS2 | −2.1 | autism susceptibility candidate 2 |
| 487 | MAP3K8 | −2.1 | mitogen-activated protein kinase kinase kinase 8 |
| 488 | ESR2 | −2.1 | estrogen receptor 2 (ER beta) |
| 489 | UBE2B | −2.1 | ubiquitin-conjugating enzyme E2B (RAD6 homolog) |
| 490 | SNX8 | −2.1 | sorting nexin 8 |
| 491 | RICTOR | −2.1 | rapamycin-insensitive companion of mTOR |
| 492 | CD7 | −2.1 | CD7 molecule |
| 493 | IQGAP2 | −2.1 | IQ motif containing GTPase activating protein 2 |
| 494 | ANKRD44 | −2.1 | ankyrin repeat domain 44 |
| 495 | MGC12916 | −2.1 | hypothetical protein MGC12916 |
| 496 | TM6SF1 | −2.1 | transmembrane 6 superfamily member 1 |
| 497 | GPR171 | −2.1 | G protein-coupled receptor 171 |
| 498 | NR1D2 | −2.1 | nuclear receptor subfamily 1, group D, member 2 |
| 499 | HLA-E | −2.1 | major histocompatibility complex, class I, E |
| 500 | ZFAND3 | −2.1 | zinc finger, AN1-type domain 3 |
| 501 | OAS3 | −2.1 | 2'-5'-oligoadenylate synthetase 3, 100 kDa |
| 502 | IFIT5 | −2.1 | interferon-induced protein with tetratricopeptide repeats 5 |
| 503 | SLC16A14 | −2.1 | solute carrier family 16, member 14 (monocarboxylic acid transporter 14) |
| 504 | PFAAP5 | −2.1 | phosphonoformate immuno-associated protein 5 |
| 505 | SNRK | −2.1 | SNF related kinase |
| 506 | PYHIN1 | −2.1 | pyrin and HIN domain family, member 1 |
| 507 | GAN | −2.1 | giant axonal neuropathy (gigaxonin) |
| 508 | KIAA0265 | −2.1 | KIAA0265 protein |
| 509 | PCBP2 | −2.1 | poly(rC) binding protein 2 |
| 510 | PLGLB1 | −2.0 | plasminogen-like B1 |
| 511 | NASP | −2.0 | nuclear autoantigenic sperm protein (histone-binding) |
| 512 | MIRH1 | −2.0 | microRNA host gene (non-protein coding) 1 |
| 513 | CD44 | −2.0 | CD44 molecule (Indian blood group) |
| 514 | MAP2K3 | −2.0 | mitogen-activated protein kinase kinase 3 |
| 515 | TRPS1 | −2.0 | trichorhinophalangeal syndrome I |
| 516 | EPB41L4A | −2.0 | erythrocyte membrane protein band 4.1 like 4A |
| 517 | MGEA5 | −2.0 | meningioma expressed antigen 5 (hyaluronidase) |
| 518 | CTSS | −2.0 | cathepsin S |
| 519 | TBC1D4 | −2.0 | TBC1 domain family, member 4 |
| 520 | UFM1 | −2.0 | ubiquitin-fold modifier 1 |
| 521 | RAB11FIP1 | −2.0 | RAB11 family interacting protein 1 (class I) |
| 522 | RAPH1 | −2.0 | Ras association (RalGDS/AF-6) and pleckstrin homology domains 1 |
| 523 | PRPF39 | −2.0 | PRP39 pre-mRNA processing factor 39 homolog (S. cerevisiae) |
| 524 | HIPK1 | −2.0 | homeodomain interacting protein kinase 1 |
| 525 | NR3C1 | −2.0 | nuclear receptor subfamily 3, group C, member 1 (glucocorticoid receptor) |
| 526 | ZNF148 | −2.0 | zinc finger protein 148 |
| 527 | RPS27 | −2.0 | ribosomal protein S27 (metallopanstimulin 1) |
| 528 | MARCH6 | −2.0 | membrane-associated ring finger (C3HC4) 6 |
| 529 | SNX5 | −2.0 | sorting nexin 5 |
| 530 | IL32 | −2.0 | interleukin 32 |
| 531 | ZBTB11 | −2.0 | zinc finger and BTB domain containing 11 |
| 532 | TBCA | −2.0 | tubulin folding cofactor A |
| 533 | C16orf52 | −2.0 | chromosome 16 open reading frame 52 |
| 534 | UBE2E1 | −2.0 | ubiquitin-conjugating enzyme E2E 1 (UBC4/5 homolog, yeast) |
| 535 | ETV6 | −2.0 | ets variant gene 6 (TEL oncogene) |
| 536 | C1orf9 | −2.0 | chromosome 1 open reading frame 9 |
| 537 | PPP1R15A | −2.0 | protein phosphatase 1, regulatory (inhibitor) subunit 15A |
| 538 | SFRS4 | −2.0 | splicing factor, arginine/serine-rich 4 |
| 539 | ZNF26 | −2.0 | zinc finger protein 26 |
| 540 | ZNF814 | −2.0 | zinc finger protein 814 |

TABLE 4-continued

Human genes that are down-regulated in Th17 conditions. Genes known to be down-regulated in the Th17 pathway are highlighted in bold as an indication of the validity of the data.

| order | gene name | fold change | description |
|---|---|---|---|
| 541 | CUL4A | −2.0 | cullin 4A |
| 542 | TMEM2 | −2.0 | transmembrane protein 2 |
| 543 | COPA | −2.0 | coatomer protein complex, subunit alpha |
| 544 | SLC35F5 | −2.0 | solute carrier family 35, member F5 |
| 545 | AKAP11 | −2.0 | A kinase (PRKA) anchor protein 11 |
| 546 | SETD2 | −2.0 | SET domain containing 2 |
| 547 | SLC7A1 | −2.0 | solute carrier family 7 (cationic amino acid transporter, y+ system), member 1 |
| 548 | YME1L1 | −2.0 | YME1-like 1 (*S. cerevisiae*) |
| 549 | EIF2AK3 | −2.0 | eukaryotic translation initiation factor 2-alpha kinase 3 |
| 550 | TCERG1 | −2.0 | transcription elongation regulator 1 |

While certain of the particular embodiments of the present invention have been described and specifically exemplified above, it is not intended that the invention be limited to such embodiments. Various modifications may be made thereto without departing from the scope and spirit of the present invention, as set forth in the following claims.

REFERENCES

1. Weaver, C. T., Hatton, R. D., Mangan, P. R. & Harrington, L. E. IL-17 family cytokines and the expanding diversity of effector T cell lineages. *Annual review of immunology* 25, 821-852 (2007).
2. Bettelli, E., Korn, T. & Kuchroo, V. K. Th17: the third member of the effector T cell trilogy. *Current opinion in immunology* 19, 652-657 (2007).
3. Stockinger, B. & Veldhoen, M. Differentiation and function of Th17 T cells. *Current opinion in immunology* 19, 281-286 (2007).
4. Acosta-Rodriguez, E. V. et al. Surface phenotype and antigenic specificity of human interleukin 17-producing T helper memory cells. *Nature immunology* 8, 639-646 (2007).
5. Annunziato, F. et al. Phenotypic and functional features of human Th17 cells. *J Exp Med* 204, 1849-1861 (2007).
6. Lock, C. et al. Gene-microarray analysis of multiple sclerosis lesions yields new targets validated in autoimmune encephalomyelitis. *Nat Med* 8, 500-508 (2002).
7. Matusevicius, D. et al. Interleukin-17 mRNA expression in blood and CSF mononuclear cells is augmented in multiple sclerosis. *Mult Scler* 5, 101-104 (1999).
8. Tzartos, J. S. et al. Interleukin-17 production in central nervous system-infiltrating T cells and glial cells is associated with active disease in multiple sclerosis. *Am J Pathol* 172, 146-155 (2008).
9. Kebir, H. et al. Human T(H)17 lymphocytes promote blood-brain barrier disruption and central nervous system inflammation. *Nat Med* 13, 1173-1175 (2007).
10. Chabaud, M. et al. Human interleukin-17: A T cell-derived proinflammatory cytokine produced by the rheumatoid synovium. *Arthritis Rheum* 42, 963-970 (1999).
11. Attur, M. G., Patel, R. N., Abramson, S. B. & Amin, A. R. Interleukin-17 up-regulation of nitric oxide production in human osteoarthritis cartilage. *Arthritis Rheum* 40, 1050-1053 (1997).
12. Fossiez, F. et al. T cell interleukin-17 induces stromal cells to produce proinflammatory and hematopoietic cytokines. *J Exp Med* 183, 2593-2603 (1996).
13. Homey, B. et al. Up-regulation of macrophage inflammatory protein-3 alpha/CCL20 and CC chemokine receptor 6 in psoriasis. *J Immunol* 164, 6621-6632 (2000).
14. Zheng, Y. et al. Interleukin-22, a T(H)17 cytokine, mediates IL-23-induced dermal inflammation and acanthosis. *Nature* 445, 648-651 (2007).
15. Wilson, N. J. et al. Development, cytokine profile and function of human interleukin 17-producing helper T cells. *Nature immunology* 8, 950-957 (2007).
16. Annunziato, F. et al. Phenotypic and functional features of human Th17 cells. *J Exp Med* 204, 1849-1861 (2007).
17. Becker, C. et al. Constitutive p40 promoter activation and IL-23 production in the terminal ileum mediated by dendritic cells. *The Journal of clinical investigation* 112, 693-706 (2003).
18. McGeachy, M. J. et al. TGF-beta and IL-6 drive the production of IL-17 and IL-10 by T cells and restrain T(H)-17 cell-mediated pathology. *Nature immunology* 8, 1390-1397 (2007).
19. Duerr, R. H. et al. A genome-wide association study identifies IL23R as an inflammatory bowel disease gene. *Science* 314, 1461-1463 (2006).
20. Ivanov, I I, Zhou, L. & Littman, D. R. Transcriptional regulation of Th17 cell differentiation. *Semin Immunol* (2007).
21. Ivanov, I I et al. The orphan nuclear receptor RORgammat directs the differentiation program of proinflammatory IL-17+ T helper cells. *Cell* 126, 1121-1133 (2006).
22. Veldhoen, M., Hocking, R. J., Atkins, C. J., Locksley, R. M. & Stockinger, B. TGFbeta in the context of an inflammatory cytokine milieu supports de novo differentiation of IL-17-producing T cells. *Immunity* 24, 179-189 (2006).
23. Bettelli, E. et al. Reciprocal developmental pathways for the generation of pathogenic effector TH17 and regulatory T cells. *Nature* 441, 235-238 (2006).
24. Mangan, P. R. et al. Transforming growth factor-beta induces development of the T(H)17 lineage. *Nature* 441, 231-234 (2006).
25. Korn, T. et al. IL-21 initiates an alternative pathway to induce proinflammatory T(H)17 cells. *Nature* 448, 484-487 (2007).
26. Nurieva, R. et al. Essential autocrine regulation by IL-21 in the generation of inflammatory T cells. *Nature* 448, 480-483 (2007).
27. Zhou, L. et al. IL-6 programs T(H)-17 cell differentiation by promoting sequential engagement of the IL-21 and IL-23 pathways. *Nature immunology* 8, 967-974 (2007).

28. Chen, Z., Tato, C. M., Muul, L., Laurence, A. & O'Shea, J. J. Distinct regulation of interleukin-17 in human T helper lymphocytes. *Arthritis Rheum* 56, 2936-2946 (2007).
29. Acosta-Rodriguez, E. V., Napolitani, G., Lanzavecchia, A. & Sallusto, F. Interleukins 1beta and 6 but not transforming growth factor-beta are essential for the differentiation of interleukin 17-producing human T helper cells. *Nature immunology* 8, 942-949 (2007).
30. van Beelen, A. J. et al. Stimulation of the intracellular bacterial sensor NOD2 programs dendritic cells to promote interleukin-17 production in human memory T cells. *Immunity* 27, 660-669 (2007).
31. Evans, H. G., Suddason, T., Jackson, I., Taams, L. S. & Lord, G. M. Optimal induction of T helper 17 cells in humans requires T cell receptor ligation in the context of Toll-like receptor-activated monocytes. *Proc Natl Acad Sci USA* 104, 17034-17039 (2007).
32. Stockinger, B., Veldhoen, M. & Martin, B. Th17 T cells: Linking innate and adaptive immunity. *Semin Immunol* (2007).
33. De Rosa, S. C., Herzenberg, L. A., Herzenberg, L. A. & Roederer, M. 11-color, 13-parameter flow cytometry: identification of human naive T cells by phenotype, function, and T-cell receptor diversity. *Nat Med* 7, 245-248 (2001).
34. Laurence, A. & O'Shea, J. J. TH-17 differentiation: of mice and men. *Nature immunology* 8, 903-905 (2007).
35. Igawa, D., Sakai, M. & Savan, R. An unexpected discovery of two interferon gamma-like genes along with interleukin (IL)-22 and -26 from teleost: IL-22 and -26 genes have been described for the first time outside mammals. *Mol Immunol* 43, 999-1009 (2006).
36. Sato, W., Aranami, T. & Yamamura, T. Cutting edge: Human Th17 cells are identified as bearing CCR2+CCR5− phenotype. *J Immunol* 178, 7525-7529 (2007).
37. Kyrtsonis, M. C. et al. Serum transforming growth factor-beta 1 is related to the degree of immunoparesis in patients with multiple myeloma. *Med Oncol* 15, 124-128 (1998).
38. Wight, M. TGF-beta1 in bovine serum. *Art. Sci* 19, 1-3 (2001).
39. Tran, D. Q., Ramsey, H. & Shevach, E. M. Induction of FOXP3 expression in naive human CD4+FOXP3 T cells by T-cell receptor stimulation is transforming growth factor-{beta} dependent but does not confer a regulatory phenotype. *Blood* 110, 2983-2990 (2007).
40. Laurence, A. et al. Interleukin-2 signaling via STAT5 constrains T helper 17 cell generation. *Immunity* 26, 371-381 (2007).
41. Kryczek, I. et al. Cutting edge: opposite effects of IL-1 and IL-2 on the regulation of IL-17+ T cell pool IL-1 subverts IL-2-mediated suppression. *J Immunol* 179, 1423-1426 (2007).
42. Mucida, D. et al. Reciprocal TH17 and regulatory T cell differentiation mediated by retinoic acid. *Science* 317, 256-260 (2007).
43. Zhou, L. et al. TGF-beta-induced Foxp3 inhibits Th17 cell differentiation by antagonizing RORgammat function. *Nature* Accepted (2008).
44. Wei, L., Laurence, A., Elias, K. M. & O'Shea, J. J. IL-21 is produced by Th17 cells and drives IL-17 production in a STAT3-dependent manner. *J Biol Chem* 282, 34605-34610 (2007).
45. Parham, C. et al. A receptor for the heterodimeric cytokine IL-23 is composed of IL-12Rbeta1 and a novel cytokine receptor subunit, IL-23R. *J Immunol* 168, 5699-5708 (2002).
46. Habib, T., Senadheera, S., Weinberg, K. & Kaushansky, K. The common gamma chain (gamma c) is a required signaling component of the IL-21 receptor and supports IL-21-induced cell proliferation via JAK3. *Biochemistry* 41, 8725-8731 (2002).
47. Asao, H. et al. Cutting edge: the common gamma-chain is an indispensable subunit of the IL-21 receptor complex. *J Immunol* 167, 1-5 (2001).
48. Gerhartz, C. et al. Differential activation of acute phase response factor/STAT3 and STAT1 via the cytoplasmic domain of the interleukin 6 signal transducer gp130. I. Definition of a novel phosphotyrosine motif mediating STAT1 activation. *J Biol Chem* 271, 12991-12998 (1996).
49. Stahl, N. et al. Choice of STATs and other substrates specified by modular tyrosine-based motifs in cytokine receptors. *Science* 267, 1349-1353 (1995).
50. Muzio, M., Ni, J., Feng, P. & Dixit, V. M. IRAK (Pelle) family member IRAK-2 and MyD88 as proximal mediators of IL-1 signaling. *Science* 278, 1612-1615 (1997).
51. Wesche, H., Henzel, W. J., Shillinglaw, W., Li, S. & Cao, Z. MyD88: an adapter that recruits IRAK to the IL-1 receptor complex. *Immunity* 7, 837-847 (1997).
52. Cho, M. L. et al. STAT3 and NF-kappaB signal pathway is required for IL-23-mediated IL-17 production in spontaneous arthritis animal model IL-1 receptor antagonist-deficient mice. *J Immunol* 176, 5652-5661 (2006).
53. Sutton, C., Brereton, C., Keogh, B., Mills, K. H. & Lavelle, E. C. A crucial role for interleukin (IL)-1 in the induction of IL-17-producing T cells that mediate autoimmune encephalomyelitis. *J Exp Med* 203, 1685-1691 (2006).
54. Sporn, M. B. & Roberts, A. B. TGF-beta: problems and prospects. *Cell Regul* 1, 875-882 (1990).
55. Hor, S., Pirzer, H., Dumoutier, L., Bauer, F. & Wittmann, S. The T-cell Lymphokine Interleukin-26 Targets Epithelial Cells through the Interleukin-20 Receptor 1 . . . *Journal of Biological Chemistry* (2004).
56. Lim, H. W., Lee, J., Hillsamer, P. & Kim, C. H. Human Th17 cells share major trafficking receptors with both polarized effector T cells and FOXP3+ regulatory T cells. *J Immunol* 180, 122-129 (2008).
57. Sundrud, M. S. et al. Genetic reprogramming of primary human T cells reveals functional plasticity in Th cell differentiation. *J Immunol* 171, 3542-3549 (2003).
58. Yang, X. O. et al. T Helper 17 Lineage Differentiation Is Programmed by Orphan Nuclear Receptors RORalpha and RORgamma. *Immunity* (2007).
59. Kikly, K., Liu, L., Na, S. & Sedgwick, J. D. The IL-23/Th(17) axis: therapeutic targets for autoimmune inflammation. *Current opinion in immunology* 18, 670-675 (2006).
60. Dubinsky, M. C. et al. IL-23 receptor (IL-23R) gene protects against pediatric Crohn's disease. *Inflamm Bowel Dis* 13, 511-515 (2007).
61. Oliver, J., Rueda, B., Lopez-Nevot, M. A., Gomez-Garcia, M. & Martin, J. Replication of an association between IL23R gene polymorphism with inflammatory bowel disease. *Clin Gastroenterol Hepatol* 5, 977-981, 981 e971-972 (2007).
62. Smith, R. L. et al. Polymorphisms in the IL-12beta and IL-23R Genes Are Associated with Psoriasis of Early Onset in a UK Cohort. *J Invest Dermatol* (2007).
63. Baldassano, R. N. et al. Association of variants of the interleukin-23 receptor gene with susceptibility to pediatric Crohn's disease. *Clin Gastroenterol Hepatol* 5, 972-976 (2007).
64. Glas, J. et al. rs1004819 is the main disease-associated IL23R variant in German Crohn's disease patients: combined analysis of IL23R, CARD15, and OCTN1/2 variants. *PLoS ONE* 2, e819 (2007).
65. Unutmaz, D., KewalRamani, V. N., Marmon, S. & Littman, D. R. Cytokine signals are sufficient for HIV-1 infection of resting human T lymphocytes. *J Exp Med* 189, 1735-1746 (1999).

Sequence Information

Genbank Accession No.: NM_005060 The following is the
human RORgamma mRNA sequence. The nucleotides unique for RORgamma
are underlined.
>gi|48255916: 109-1665 *Homo sapiens* RAR-related orphan receptor C
(RORC), transcript variant 1, mRNA (SEQ ID NO: 29)

<u>ATGGACAGGGCCCCACAGAGACAGCACCGAGCCTCACGGGAGCTGCTGGCTGCAAAGAAGACCCACACCT</u>
CACAAATTGAAGTGATCCCTTGCAAAATCTGTGGGGACAAGTCGTCTGGGATCCACTACGGGGTTATCAC
CTGTGAGGGGTGCAAGGGCTTCTTCCGCCGGAGCCAGCGCTGTAACGCGGCCTACTCCTGCACCCGTCAG
CAGAACTGCCCCATCGACCGCACCAGCCGAAACCGATGCCAGCACTGCCGCCTGCAGAAATGCCTGGCGC
TGGGCATGTCCCGAGATGCTGTCAAGTTCGGCCGCATGTCCAAGAAGCAGAGGGACAGCCTGCATGCAGA
AGTGCAGAAACAGCTGCAGCAGCGGCAACAGCAGCAACAGGAACCAGTGGTCAAGACCCCTCCAGCAGGG
GCCCAAGGAGCAGATACCCTCACCTACACCTTGGGGCTCCCAGACGGGCAGCTGCCCCTGGGCTCCTCGC
CTGACCTGCCTGAGGCTTCTGCCTGTCCCCCTGGCCTCCTGAAAGCCTCAGGCTCTGGGCCCTCATATTC
CAACAACTTGGCCAAGGCAGGGCTCAATGGGCCTCATGCCACCTTGAATACAGCCCTGAGCGGGGCAAG
GCTGAGGGCAGAGAGAGCTTCTATAGCACAGGCAGCCAGCTGACCCCTGACCGATGTGGACTTCGTTTTG
AGGAACACAGGCATCCTGGGCTTGGGGAACTGGGACAGGGCCCAGACAGCTACGGCAGCCCCAGTTTCCG
CAGCACACCGGAGGCACCCTATGCCTCCCTGACAGAGATAGAGCACCTGGTGCAGAGCGTCTGCAAGTCC
TACAGGGAGACATGCCAGCTGCGGCTGGAGGACCTGCTGCGGCAGCGCTCCAACATCTTCTCCCGGGAGG
AAGTGACTGGCTACCAGAGGAAGTCCATGTGGGAGATGTGGGAACGGTGTGCCCACCACCTCACCGAGGC
CATTCAGTACGTGGTGGAGTTCGCCAAGAGGCTCTCAGGCTTTATGGAGCTCTGCCAGAATGACCAGATT
GTGCTTCTCAAAGCAGGAGCAATGGAAGTGGTGCTGGTTAGGATGTGCCGGGCCTACAATGCTGACAACC
GCACGGTCTTTTTTGAAGGCAAATACGGTGGCATGGAGCTGTTCCGAGCCTTGGGCTGCAGCGAGCTCAT
CAGCTCCATCTTTGACTTCTCCCACTCCCTAAGTGCCTTGCACTTTTCCGAGGATGAGATTGCCCTCTAC
ACAGCCCTTGTTCTCATCAATGCCCATCGGCCAGGGCTCCAAGAGAAAAGGAAAGTAGAACAGCTGCAGT
ACAATCTGGAGCTGGCCTTTCATCATCATCTCTGCAAGACTCATCGCCAAAGCATCCTGGCAAAGCTGCC
ACCCAAGGGGAAGCTTCGGAGCCTGTGTAGCCAGCATGTGGAAAGGCTGCAGATCTTCCAGCACCTCCAC
CCCATCGTGGTCCAAGCCGCTTTCCCTCCACTCTACAAGGAGCTCTTCAGCACTGAAACCGAGTCACCTG
TGGGGCTGTCCAAGTGA

Genbank Accession No.: NP_005051 The following is the human
RORgamma protein sequence. The amino acids unique for RORgamma are underlined.
The AF2 domain is indicated using underlining and bold font.

>gi|19743909|ref|NP_005051.21 RAR-related orphan receptor C isoform
a [*Homo sapiens*]

(SEQ ID NO: 30)

<u>MDRAPQRQHRASRELLAAKKTHTSQ</u>IEVIPCKICGDKSSGIHYGVITCEGCKGFFRRSQRCNAAYSCTRQ
QNCPIDRTSRNRCQHCRLQKCLALGMSRDAVKFGRMSKKQRDSLHAEVQKQLQQRQQQQQEPVVKTPPAG
AQGADTLTYTLGLPDGQLPLGSSPDLPEASACPPGLLKASGSGPSYSNNLAKAGLNGASCHLEYSPERGK
AEGRESFYSTGSQLTPDRCGLRFEEHRHPGLGELGQGPDSYGSPSFRSTPEAPYASLTEIEHLVQSVCKS
YRETCQLRLEDLLRQRSNIFSREEVTGYQRKSMWEMWERCAHHLTEAIQYVVEFAKRLSGFMELCQNDQI
VLLKAGAMEVVLVRMCRAYNADNRTVFFEGKYGGMELFRALGCSELISSIFDFSHSLSALHFSEDEIALY
TALVLINAHRPGLQEKRKVEQLQYNLELAFHHHLCKTHRQSILAKLPPKGKLRSLCSQHVERLQIFQHLH
PIVVQAAFPP<u>LYKELF</u>STETESPVGLSK

Genbank Accession No.: NM_001001523 The following is the human
RORgammat mRNA sequence. The nucleotides unique for RORgamma are
underlined.

>gi|48255917: 142-1635 *Homo sapiens* RAR-related orphan receptor C
(RORC), transcript variant 2, mRNA (SEQ ID NO: 31)

<u>ATGAGAAC</u>ACAAATTGAAGTGATCCCTTGCAAAATCTGTGGGGACAAGTCGTCTGGGATCCACTACGGGG
TTATCACCTGTGAGGGGTGCAAGGGCTTCTTCCGCCGGAGCCAGCGCTGTAACGCGGCCTACTCCTGCAC
CCGTCAGCAGAACTGCCCCATCGACCGCACCAGCCGAAACCGATGCCAGCACTGCCGCCTGCAGAAATGC
CTGGCGCTGGGCATGTCCCGAGATGCTGTCAAGTTCGGCCGCATGTCCAAGAAGCAGAGGGACAGCCTGC
ATGCAGAAGTGCAGAAACAGCTGCAGCAGCGGCAACAGCAGCAACAGGAACCAGTGGTCAAGACCCCTCC
AGCAGGGGCCCAAGGAGCAGATACCCTCACCTACACCTTGGGGCTCCCAGACGGGCAGCTGCCCCTGGGC
TCCTCGCCTGACCTGCCTGAGGCTTCTGCCTGTCCCCCTGGCCTCCTGAAAGCCTCAGGCTCTGGGCCCT
CATATTCCAACAACTTGGCCAAGGCAGGGCTCAATGGGCCTCATGCCACCTTGAATACAGCCCTGAGCG
GGGCAAGGCTGAGGGCAGAGAGAGCTTCTATAGCACAGGCAGCCAGCTGACCCCTGACCGATGTGGACTT
CGTTTTGAGGAACACAGGCATCCTGGGCTTGGGGAACTGGGACAGGGCCCAGACAGCTACGGCAGCCCCA
GTTTCCGCAGCACACCGGAGGCACCCTATGCCTCCCTGACAGAGATAGAGCACCTGGTGCAGAGCGTCTG
CAAGTCCTACAGGGAGACATGCCAGCTGCGGCTGGAGGACCTGCTGCGGCAGCGCTCCAACATCTTCTCC
CGGGAGGAAGTGACTGGCTACCAGAGGAAGTCCATGTGGGAGATGTGGGAACGGTGTGCCCACCACCTCA
CCGAGGCCATTCAGTACGTGGTGGAGTTCGCCAAGAGGCTCTCAGGCTTTATGGAGCTCTGCCAGAATGA
CCAGATTGTGCTTCTCAAAGCAGGAGCAATGGAAGTGGTGCTGGTTAGGATGTGCCGGGCCTACAATGCT
GACAACCGCACGGTCTTTTTTGAAGGCAAATACGGTGGCATGGAGCTGTTCCGAGCCTTGGGCTGCAGCG
AGCTCATCAGCTCCATCTTTGACTTCTCCCACTCCCTAAGTGCCTTGCACTTTTCCGAGGATGAGATTGC
CCTCTACACAGCCCTTGTTCTCATCAATGCCCATCGGCCAGGGCTCCAAGAGAAAAGGAAAGTAGAACAG
CTGCAGTACAATCTGGAGCTGGCCTTTCATCATCATCTCTGCAAGACTCATCGCCAAAGCATCCTGGCAA
AGCTGCCACCCAAGGGGAAGCTTCGGAGCCTGTGTAGCCAGCATGTGGAAAGGCTGCAGATCTTCCAGCA
CCTCCACCCCATCGTGGTCCAAGCCGCTTTCCCTCCACTCTACAAGGAGCTCTTCAGCACTGAAACCGAG
TCACCTGTGGGGCTGTCCAAGTGA

-continued

Sequence Information

Genbank Accession No.: NP_001001523 The following is the human RORgammat protein sequence. The amino acids unique for RORgammat are underlined. The AF2 domain is indicated using underlining and bold font.

>gi|48255918|ref|NP_001001523.1| RAR-related orphan receptor C isoform b [Homo sapiens]

(SEQ ID NO: 32)

MRTQIEVIPCKICGDKSSGIHYGVITCEGCKGFFRRSQRCNAAYSCTRQQNCPIDRTSRNRCQHCRLQKC
LALGMSRDAVKFGRMSKKQRDSLHAEVQKQLQQRQQQQEPVVKTPPAGAQGADTLTYTLGLPDGQLPLG
SSPDLPEASACPPGLLKASGSGPSYSNNLAKAGLNGASCHLEYSPERGKAEGRESFYSTGSQLTPDRCGL
RFEEHRHPGLGELGQGPDSYGSPSFRSTPEAPYASLTEIEHLVQSVCKSYRETCQLRLEDLLRQRSNIFS
REEVTGYQRKSMWEMWERCAHHLTEAIQYVVEFAKRLSGFMELCQNDQIVLLKAGAMEVVLVRMCRAYNA
DNRTVFFEGKYGGMELFRALGCSELISSIFDFSHSLSALHFSEDEIALYTALVLINAHRPGLQEKRKVEQ
LQYNLELAFHHHLCKTHRQSILAKLPPKGKLRSLCSQHVERLQIFQHLHPIVVQAAFPPLYKELFSTETE
SPVGLSK

Genbank Accession No.: NM_011281 The following is the mRNA sequence for mouse RORgamma. The underlined sequences are specific for mouse RORgamma.

>gi|6755343: 107-1657 Mus musculus RAR-related orphan receptor gamma (Rorc), mRNA (SEQ ID NO: 33)

ATGGACAGGGCCCCACAGAGACACCACCGGACATCTCGGGAGCTGCTGGCTGCAAAGAAGACCCACACCT
CACAAATTGAAGTGATCCCTTGCAAGATCTGTGGGGACAAGTCATCTGGGATCCACTACGGGGTTATCAC
CTGTGAGGGGTGCAAGGGCTTCTTCCGCCGCAGCCAGCAGTGTAATGTGGCCTACTCCTGCACGCGTCAG
CAGAACTGCCCCATTGACCGAACCAGCCGCAACCGATGCCAGCATTGCCGCCTGCAGAAGTGCCTGGCTC
TGGGCATGTCCCGAGATGCTGTCAAGTTTGGCCGAATGTCCAAGAAGCAGAGGGACAGTCTACATGCAGA
AGTGCAGAAACAACTGCAACAGCAGCAGCAACAGGAACAAGTGGCCAAGACTCCTCCAGCTGGGAGCCGC
GGAGCAGACACACTTACATACACTTTAGGGCTCTCAGATGGGCAGCTACCACTGGGCGCCTCACCTGACC
TACCCGAGGCCTCTGCTTGTCCCCCTGGCCTCCTGAGAGCCTCAGGCTCTGGCCCACCATATTCCAATAC
CTTGGCCAAAACAGAGGTCCAGGGGGCCTCCTGCCACCTTGAGTATAGTCCAGAACGAGGCAAAGCTGAA
GGCAGAGACAGCATCTATAGCACTGACGGCCAACTTACTCTTGGAAGATGTGGACTTCGTTTTGAGGAAA
CCAGGCATCCTGAACTTGGGGAACCAGAACAGGGTCCAGACAGCCACTGCATTCCCAGTTTCTGCAGTGC
CCCAGAGGTACCATATGCCTCTCTGACAGACATAGAGTACCTGGTACAGAATGTCTGCAAGTCCTTCCGA
GAGACATGCCAGCTGCGACTGGAGGACCTTCTACGGCAGCGCACCAACCTCTTTTCACGGGAGGAGGTGA
CCAGCTACCAGAGGAAGTCAATGTGGGAGATGTGGGAGCGCTGTGCCCACCACCTCACTGAGGCCATTCA
GTATGTGGTGGAGTTTGCCAAGCGGCTTTCAGGCTTCATGGAGCTCTGCCAGAATGACCAGATCATACTA
CTGACAGCAGGAGCAATGGAAGTCGTCCTAGTCAGAATGTGCAGGGCCTACAATGCCAACAACCACACAG
TCTTTTTTGAAGGCAAATACGGTGGTGTGGAGCTGTTTCGAGCCTTGGGCTGCAGCGAGCTCATCAGCTC
CATATTTGACTTTTCCCACTTCCTCAGCGCCCTGTGTTTTTCTGAGGATGAGATTGCCCTCTACACGGCC
CTGGTTCTCATCAATGCCAACCGTCCTGGGCTCCAAGAGAAGAGGAGAGTGGAACATCTGCAATACAATT
TGGAACTGGCTTTCCATCATCATCTCTGCAAGACTCATCGACAAGGCCTCCTAGCCAAGCTGCCACCCAA
AGGAAAACTCCGGAGCCTGTGCAGCCAACATGTGGAAAAGCTGCAGATCTTCCAGCACCTCCACCCCATC
GTGGTCCAAGCCGCCTTCCCGCCACTCTATAAGGAACTCTTCAGCACTGATGTTGAATCCCCTGAGGGGC
TGTCAAAGTGA

Genbank Accession No.: NP_035411 The following is the amino acid sequence for mouse RORgamma. The underlined amino acids are specific for mouse RORgamma. The AF2 domain is indicated using underlining and bold font.

>gi|6755344|ref|NP_035411.1| RAR-related orphan receptor gamma [Mus musculus]

(SEQ ID NO: 34)

MDRAPQRHHRTSRELLAAKKTHTSQIEVIPCKICGDKSSGIHYGVITCEGCKGFFRRSQQCNVAYSCTRQ
QNCPIDRTSRNRCQHCRLQKCLALGMSRDAVKFGRMSKKQRDSLHAEVQKQLQQQQQEQVAKTPPAGSR
GADTLTYTLGLSDGQLPLGASPDLPEASACPPGLLRASGSGPPYSNTLAKTEVQGASCHLEYSPERGKAE
GRDSIYSTDGQLTLGRCGLRFEETRHPELGEPEQGPDSHCIPSFCSAPEVPYASLTDIEYLVQNVCKSFR
ETCQLRLEDLLRQRTNLFSREEVTSYQRKSMWEMWERCAHHLTEAIQYVVEFAKRLSGFMELCQNDQIIL
LTAGAMEVVLVRMCRAYNANNHTVFFEGKYGGVELFRALGCSELISSIFDFSHFLSALCFSEDEIALYTA
LVLINANRPGLQEKRRVEHLQYNLELAFHHHLCKTHRQGLLAKLPPKGKLRSLCSQHVEKLQIFQHLHPI
VVQAAFPPLYKELFSTDVESPEGLSK

Genbank Accession No.: AF163668 The following is the mRNA sequence for mouse RORgammat. The underlined nucleotides are specific for mouse RORgammat >gi|5679306: 93-1580 Mus musculus RORgamma t mRNA, complete cds (SEQ ID NO: 35)

ATGAGAACACAAATTGAAGTGATCCCTTGCAAGATCTGTGGGGACAAGTCATCTGGGATCCACTACGGGG
TTATCACCTGTGAGGGGTGCAAGGGCTTCTTCCGCCGCAGCCAGCAGTGTAATGTGGCCTACTCCTGCAC
GCGTCAGCAGAACTGCCCCATTGACCGAACCAGCCGCAACCGATGCCAGCATTGCCGCCTGCAGAAGTGC
CTGGCTCTGGGCATGTCCCGAGATGCTGTCAAGTTTGGCCGAATGTCCAAGAAGCAGAGGGACAGTCTAC
ATGCAGAAGTGCAGAAACAACTGCAACAGCAGCAGCAACAGGAACAAGTGGCCAAGACTCCTCCAGCTGG

-continued

Sequence Information

```
GAGCCGCGGAGCAGACACACTTACATACACTTTAGGGCTCTCAGATGGGCAGCTACCACTGGGCGCCTCA
CCTGACCTACCCGAGGCCTCTGCTTGTCCCCCTGGCCTCCTGAGAGCCTCAGGCTCTGGCCCACCATATT
CCAATACCTTGGCCAAAACAGAGGTCCAGGGGGCCTCCTGCCACCTTGAGTATAGTCCAGAACGAGGCAA
AGCTGAAGGCAGAGACAGCATCTATAGCACTGACGGCCAACTTACTCTTGGAAGATGTGGACTTCGTTTT
GAGGAAACCAGGCATCCTGAACTTGGGGAACCAGAACAGGGTCCAGACAGCCACTGCATTCCCAGTTTCT
GCAGTGCCCCAGAGGTACCATATGCCTCTCTGACAGACATAGAGTACCTGGTACAGAATGTCTGCAAGTC
CTTCCGAGAGACATGCCAGCTGCGACTGGAGGACCTTCTACGGCAGCGCACCAACCTCTTTTCACGGGAG
GAGGTGACCAGCTACCAGAGGAAGTCAATGTGGGAGATGTGGGAGCGCTGTGCCCACCACCTCACTGAGG
CCATTCAGTATGTGGTGGAGTTTGCCAAGCGGCTTTCAGGCTTCATGGAGCTCTGCCAGAATGACCAGAT
CATACTACTGAAAGCAGGAGCAATGGAAGTCGTCCTAGTCAGAATGTGCAGGGCCTACAATGCCAACAAC
CACACAGTCTTTTTTGAAGGCAAATACGGTGGTGTGGAGCTGTTTCGAGCCTTGGGCTGCAGCGAGCTCA
TCAGCTCCATATTTGACTTTTCCCACTTCCTCAGCGCCCTGTGTTTTTCTGAGGATGAGATTGCCCTCTA
CACGGCCCTGGTTCTCATCAATGCCAACCGTCCTGGGCTCCAAGAGAAGAGGAGAGTGGAACATCTGCAA
TACAATTTGGAACTGGCTTTCCATCATCATCTCTGCAAGACTCATCGACAAGGCCTCCTAGCCAAGCTGC
CACCCAAAGGAAAACTCCGGAGCCTGTGCAGCCAACATGTGGAAAAGCTGCAGATCTTCCAGCACCTCCA
CCCCATCGTGGTCCAAGCCGCCTTCCCTCCACTCTATAAGGAACTCTTCAGCACTGATGTTGAATCCCCT
GAGGGGCTGTCAAAGTGA
```

Genbank Accession No.: AAD46913 The following is the amino acid
sequence for mouse RORgammat. The underlined amino acids are specific
or mouse RORgammat. The AF2 domain is indicated using underlining and
bold font.

>gi|5679307|gb|AAD46913.1|AF163668_1 RORgamma t [Mus musculus]
(SEQ ID NO: 36)

<u>MRT</u>QIEVIPCKICGDKSSGIHYGVITCEGCKGFFRRSQQCNVAYSCTRQQNCPIDRTSRNRCQHCRLQKC
LALGMSRDAVKFGRMSKKQRDSLHAEVQKQLQQQQQQEQVAKTPPAGSRGADTLTYTLGLSDGQLPLGAS
PDLPEASACPPGLLRASGSGPPYSNTLAKTEVQGASCHLEYSPERGKAEGRDSIYSTDGQLTLGRCGLRF
EETRHPELGEPEQGPDSHCIPSFCSAPEVPYASLTDIEYLVQNVCKSFRETCQLRLEDLLRQRTNLFSRE
EVTSYQRKSMWEMWERCAHHLTEAIQYVVEFAKRLSGFMELCQNDQIILLKAGAMEVVLVRMCRAYNANN
HTVFFEGKYGGVELFRALGCSELISSIFDFSHFLSALCFSEDEIALYTALVLINANRPGLQEKRRVEHLQ
YNLELAFHHHLCKTHRQGLLAKLPPKGKLRSLCSQHVEKLQIFQHLHPIVVQAAFPP<u>LYKELF</u>STDVESP
EGLSK

Genbank Accession No.: NM_134262.1 The following is the mRNA sequence
for human RORalpha isoform d.

>gi|19743904|ref|NM_134262.1| Homo sapiens RAR-related orphan receptor
A (RORA), transcript variant 4, mRNA
(SEQ ID NO: 37)

```
TGTGGCTCGGGCGGCGGCGCGGCGGCGGCAGAGGGGCTCCGGGGTCGGACCATCCGCTCTCCCTGC
GCTCTCCGCACCGCGCTTAAATGATGTATTTTGTGATCGCAGCGATGAAAGCTCAAATTGAAATTATTCC
ATGCAAGATCTGTGGAGACAAATCATCAGGAATCCATTATGGTGTCATTACATGTGAAGGCTGCAAGGGC
TTTTTCAGGAGAAGTCAGCAAAGCAATGCCACCTACTCCTGTCCTCGTCAGAAGAACTGTTTGATTGATC
GAACCAGTAGAAACCGCTGCCAACACTGTCGATTACAGAAATGCCTTGCCGTAGGGATGTCTCGAGATGC
TGTAAAATTTGGCCGAATGTCAAAAAAGCAGAGAGACAGCTTGTATGCAGAAGTACAGAAACACCGGATG
CAGCAGCAGCAGCGCGACCACCAGCAGCAGCCTGGAGAGGCTGAGCCGCTGACGCCCACCTACAACATCT
CGGCCAACGGGCTGACGGAACTTCACGACGACCTCAGTAACTACATTGACGGGCACACCCCTGAGGGGAG
TAAGGCAGACTCCGCCGTCAGCAGCTTCTACCTGGACATACAGCCTTCCCCAGACCAGTCAGGTCTTGAT
ATCAATGGAATCAAACCAGAACCAATATGTGACTACACACCAGCATCAGGCTTCTTTCCCTACTGTTCGT
TCACCAACGGCGAGACTTCCCCAACTGTGTCCATGGCAGAATTAGAACACCTTGCACAGAATATATCTAA
ATCGCATCTGGAAACCTGCCAATACTTGAGAGAAGAGCTCCAGCAGATAACGTGGCAGACCTTTTTACAG
GAAGAAATTGAGAACTATCAAAACAAGCAGCGGGAGGTGATGTGGCAATTGTGTGCCATCAAAATTACAG
AAGCTATACAGTATGTGGTGGAGTTTGCCAAACGCATTGATGGATTTATGGAACTGTGTCAAAATGATCA
AATTGTGCTTCTAAAAGCAGGTTCTCTAGAGGTGGTGTTTATCAGAATGTGCCGTGCCTTTGACTCTCAG
AACAACACCGTGTACTTTGATGGGAAGTATGCCAGCCCCGACGTCTTCAAATCCTTAGGTTGTGAAGACT
TTATTAGCTTTGTGTTTGAATTTGGAAAGAGTTTATGTTCTATGCACCTGACTGAAGATGAAATTGCATT
ATTTTCTGCATTTGTACTGATGTCAGCAGATCGCTCATGGCTGCAAGAAAAGGTAAAAATTGAAAAACTG
CAACAGAAAATTCAGCTAGCTCTTCAACACGTCCTACAGAAGAATCACCGAGAAGATGGAATACTAACAA
AGTTAATATGCAAGGTGTCTACATTAAGAGCCTTATGTGGACGACATACAGAAAAGCTAATGGCATTTAA
AGCAATATACCCAGACATTGTGCGACTTCATTTTCCTCCATTATACAAGGAGTTGTTCACTTCAGAATTT
GAGCCAGCAATGCAAATTGATGGGTAAATGTTATCACCTAAGCACTTCTAGAATGTCTGAAGTACAAACA
TGAAAAACAAACAAAAAAATTAACCGAGACACTTTATATGGCCCTGCACAGACCTGGAGCGCCACACACT
GCACATCTTTTGGTGATCGGGGTCAGGCAAAGGAGGGGAAACAATGAAAACAAATAAAGTTGAACTTGTT
TTTCTCA
```

Genbank Accession No.: NP_599024.1 The following is the amino acid
sequence for human RORalpha isoform d.

>gi|19743905|ref|NP_599024.1| RAR-related orphan receptor A isoform d
[Homo sapiens]
(SEQ ID NO: 38)

MMYFVIAAMKAQIEIIPCKICGDKSSGIHYGVITCEGCKGFFRRSQQSNATYSCPRQKNCLIDRTSRNRC
QHCRLQKCLAVGMSRDAVKFGRMSKKQRDSLYAEVQKHRMQQQQRDHQQQPGEAEPLTPTYNISANGLTE
LHDDLSNYIDGHTPEGSKADSAVSSFYLDIQPSPDQSGLDINGIKPEPICDYTPASGFFPYCSFTNGETS
PTVSMAELEHLAQNISKSHLETCQYLREELQQITWQTFLQEEIENYQNKQREVMWQLCAIKITEAIQYVV
EFAKRIDGFMELCQNDQIVLLKAGSLEVVFIRMCRAFDSQNNTVYFDGKYASPDVFKSLGCEDFISFVFE

-continued

Sequence Information

FGKSLCSMHLTEDEIALFSAFVLMSADRSWLQEKVKIEKLQQKIQLALQHVLQKNHREDGILTKLICKVS
TLRALCGRHTEKLMAFKAIYPDIVRLHFPPLYKELFTSEFEPAMQIDG

Genbank Accession No.: NM_006914.3 The following is the mRNA sequence
for human RORbeta.

>gi|62865658|ref|NM_006914.3| Homo sapiens RAR-related orphan receptor
B (RORB), mRNA (SEQ ID NO: 39)

```
TCTCTCCCCTCTCTTTCTCTCGCTGCTCCCTTCCTCCCTGTAACTGAACAGTGAAAATTCACATTGTG
GATCCGCTAACAGGCACAGATGTCATGTGAAAACGCACATGCTCTGCCATCCACACCGCCTTTCTTTCTT
TTCTTTCTGTTTCCTTTTTTCCCCCTTGTTCCTTCTCCCTCTTCTTTGTAACTAACAAAACCACCACCAA
CTCCTCCTCCTGCTGCTGCCCTTCCTCCTCCTCCTCAGTCCAAGTGATCACAAAAGAAATCTTCTGAGCC
GGAGGCGGTGGCATTTTTTAAAAAGCAAGCACATTGGAGAGAAAGAAAAAGAAAAACAAAACCAAAACAA
AACCCAGGCACCAGACAGCCAGAACATTTTTTTTTCACCCTTCCTGAAAACAAACAAACAAACAAACAAT
CATCAAAACAGTCACCACCAACATCAAAACTGTTAACATAGCGGCGGCGGCGGCAAACGTCACCCTGCAG
CCACGGCGTCCGCCTAAAGGGATGGTTTTCTCGGCAGAGCAGCTCTTCGCCGACCACCTTCTTCACTCGT
GCTGAGCGGGATTTTTGGGCTCTCCGGGGTTCGGGCTGGGAGCAGCTTCATGACTACGCGGAGCGGGAGA
GCGGCCACACCATGCGAGCACAAATTGAAGTGATACCATGCAAAATTTGTGGCGATAAGTCCTCTGGGAT
CCACTACGGAGTCATCACATGTGAAGGCTGCAAGGGATTCTTTAGGAGGAGCCAGCAGAACAATGCTTCT
TATTCCTGCCCAAGGCAGAGAACTGTTTAATTGACAGAACGAACAGAAACCGTTGCCAACACTGCCGAC
TGCAGAAGTGTCTTGCCCTAGGAATGTCAAGAGATGCTGTGAAGTTTGGGAGGATGTCCAAGAAGCAAAG
GGACAGCCTGTATGCTGAGGTGCAGAAGCACCAGCAGCGGCTGCAGGAACAGCGGCAGCAGAGAGTGGG
GAGGCAGAAGCCCTTGCCAGGGTGTACAGCAGCAGCATTAGCAACGGCCTGAGCAACCTGAACAACGAGA
CCAGCGGCACTTATGCCAACGGGCACGTCATTGACCTGCCCAAGTCTGAGGGTTATTACAACGTCGATTC
CGGTCAGCCGTCCCCTGATCAGTCAGGACTTGACATGACTGGAATCAAACAGATAAAGCAAGAACCTATC
TATGACCTCACATCCGTACCCAACTTGTTTACCTATAGCTCTTTCAACAATGGGCAGTTAGCACCAGGGA
TAACCATGACTGAAATCGACCGAATTGCACAGAACATCATTAAGTCCCATTTGGAGACATGTCAATACAC
CATGGAAGAGCTGCACCAGCTGGCGTGGCAGACCCACACCTATGAAGAAATTAAAGCATATCAAAGCAAG
TCCAGGGAAGCACTGTGGCAACAATGTGCCATCCAGATCACTCACGCCATCCAATACGTGGTGGAGTTTG
CAAAGCGGATAACAGGCTTCATGGAGCTCTGTCAAAATGATCAAATTCTACTTCTGAAGTCAGGTTGCTT
GGAAGTGGTTTTAGTGAGAATGTGCCGTGCCTTCAACCCATTAAACAACACTGTTCTGTTTGAAGGAAAA
TATGGAGGAATGCAAATGTTCAAAGCCTTAGGTTCTGATGACCTAGTGAATGAAGCATTTGACTTTGCAA
AGAATTTGTGTTCCTTGCAGCTGACCGAGGAGGAGATCGCTTTGTTCTCATCTGCTGTTCTGATATCTCC
AGACCGAGCCTGGCTTATAGAACCAAGGAAAGTCCAGAAGCTTCAGGAAAAAATTTATTTTGCACTTCAA
CATGTGATTCAGAAGAATCACCTGGATGATGAGACCTTGGCAAAGTTAATAGCCAAGATACCAACCATCA
CGGCAGTTTGCAACTTGCACGGGGAGAAGCTGCAGGTATTTAAGCAATCTCATCCAGAGATAGTGAATAC
ACTGTTTCCTCCGTTATACAAGGAGCTCTTTAATCCTGACTGTGCCACCGGCTGCAAATGAAGGGGACAA
GAGAACTGTCTCATAGTCATGGAATGCATCACCATTAAGACAAAAGCAATGTGTTCATGAAGACTTAAGA
AAAATGTCACTACTGCAACATTAGGAATGTCCTGCACTTAATAGAATTATTTTTCACCGCTACAGTTTGA
AGAATGTAAATATGCACCTGAGTGGGGCTCTTTTATTTGTTTGTTGTTTTGAAATGACCATAAATATA
CAAATATAGGACACTGGGTGTTATCCTTTTTTAATTTTATTCGGGTATGTTTGGGAGACAACTGTTTA
TAGAATTTTATTGTAGATATATACAAGAAAAGAGCGGTACTTTACATGATTACTTTTCCTGTTGATTGTT
CAAATATAATTTAAGAAAATTCCACTTAATAGGCTTACCTATTTCTATGTTTTTAGGTAGTTGATGCATG
TGTAAATTTGTAGCTGTCTTGGAAAGTACTGTGCATGTATGTAATAAGTATATAATATGTGAGAATATTA
TATATGACTATTACTTATACATGCACATGCACTGTGGCTTAAATACCATACCTACTAGCAATGGAGGTTC
AGTCAGGCTCTCTTCTATGATTTACCTTCTGTGTTATATGTTACCTTTATGTTAGACAATCAGGATTTTG
TTTTCCCAGCCAGAGTTTTCATCTATAGTCAATGGCAGGACGGTACCAACTCAGAGTTAAGTCTACAAAG
GAATAAACATAATGTGTGGCCTCTATATACAAACTCTATTTCTGTCAATGACATCAAAGCCTTGTCAAGA
TGGTTCATATTGGGAAGGAGACAGTATTTTAAGCCATTTTCCTGTTTCAAGAATTAGGCCACAGATAACA
TTGCAAGGTCCAAGACTTTTTTGACCAAACAGTAGATATTTTCTATTTTTCACCAGAACACATAAAAACA
CTTTTTTCTTTTGGATTTCTGGTTGTGAAACAAGCTTGATTTCAGTGCTTATTGTGTCTTCAACTGAAA
AATACAATCTGTGGATTATGACTACCAGCAATTTTTTCTAGGAAAGTTAAAAGAATAAATCAGAACCCA
GGGCAACAATGCCATTTCATGTAAACATTTTCTCTCTCACCATGTTTTGGCAAGAAAAGGTAGAAAGAGA
AGACCCAGAGTGAAGAAGTAATTCTTTATATTCCTTTCTTTAATGTATTTGTTAGGAAAAGTGGCAATAA
AGGGGGAGGCATATTATAAAATGCTATAATATAAAAATGTAGCAAAAACTTGACAGACTAGAAAAAAAAA
GATCTGTGTTATTCTAGGGAACTAATGTACCCCAAAGCCAAAACTAATTCCTGTGAAGTTTACAGTTACA
TCATCCATTTACCCTAGAATTATTTTTTAGCAACTTTTAGAAATAAAGAATACAACTGTGACATTAGGA
TCAGAGATTTTAGCTTCCTTGTACAAATTCTCACTTCTCCACCTGCTCACCAATGAAATTAATCATAAG
AAAAGCATATATTCCAAGAAATTTGTTCTGCCTGTGTCCTGGAGGCCTATACCTCTGTTATTTTCTGATA
CAAAATAAAACTTAAAAAAAAGAAAACAAGCTAA
```

Genbank Accession No.: NP_008845.2 The following is the amino acid
sequence for human RORbeta.

>gi|19743907|ref|NP_008845.2| RAR-related orphan receptor B
[Homo sapiens]

(SEQ ID NO: 40)

MRAQIEVIPCKICGDKSSGIHYGVITCEGCKGFFRRSQQNNASYSCPRQRNCLIDRTNRNRCQHCRLQKC
LALGMSRDAVKFGRMSKKQRDSLYAEVQKHQQRLQEQRQQQSGEAEALARVYSSSISNGLSNLNNETSGT
YANGHVIDLPKSEGYYNVDSGQPSPDQSGLDMTGIKQIKQEPIYDLTSVPNLFTYSSFNNGQLAPGITMT
EIDRIAQNIIKSHLETCQYTMEELHQLAWQTHTYEEIKAYQSKSREALWQQCAIQITHAIQYVVEFAKRI
TGFMELCQNDQILLLKSGCLEVVLVRMCRAFNPLNNTVLFEGKYGGMQMFKALGSDDLVNEAFDFAKNLC
SLQLTEEEIALFSSAVLISPDRAWLIEPRKVQKLQEKIYFALQHVIQKNHLDDETLAKLIAKIPTITAVC
NLHGEKLQVFKQSHPEIVNTLFPPLYKELFNPDCATGCK

What is claimed is:

1. A method for screening to identify an agent that modulates human Th-IL17+ cell differentiation in vitro, the method comprising the steps of:
   a) isolating a population of CD4+T cells from a human wherein said CD4+ T cells are isolated from cord blood, buffy coats of adult humans, cell that express CD34 (CD34+ cells) or human embryonic stem cells and dividing the population into at least a first and second sub-population of CD4+ T cells;
   b) incubating a first sub-population of CD4+T cells in serum-free culture medium comprising TGF-β, IL-1β, and any one of IL-6, IL-21 or IL-23, wherein the incubating promotes differentiation of human Th-IL17+ cells;
   c) incubating a second sub-population of CD4+T cells in serum-free culture medium comprising TGF-β, IL-1β, any one of IL-6, IL-21 or IL-23, and an agent;
   d) detecting expression of IL17, IL17F, IL23R, RORC, IL26, or FOXP3 in each of said first and second sub-populations of CD4+T cells incubated without or with the agent;
   e) comparing the expression of IL17, IL17F, IL23R, RORC, IL26, or FOXP3 in each of said first and second sub-populations of CD4+T cells generated following incubation without or with the agent, wherein a change in expression of IL17, IL17F, IL23R, RORC, IL26, or FOXP3 following incubation with the agent relative to the expression of IL17, IL17F, IL23R, RORC, IL26, or FOXP3 following incubation without the agent indicates that the agent is a modulator of human Th-IL17+ cell differentiation in vitro.

2. The method of claim 1, wherein the serum-free culture medium further comprises IL-2.

3. The method of claim 1, wherein the change in expression of IL17, IL17F, IL23R, RORC or IL26 is a decrease or increase in expression of IL17, IL17F, IL23R, RORC or IL26 following incubation with the agent, wherein the decrease indicates that the agent is an inhibitor of human Th-IL17+ cell differentiation in vitro and the increase indicates that the agent is a promoter of human Th-IL17+ cell differentiation in vitro.

4. The method of claim 1, wherein the change in expression of FOXP3 is a decrease in expression of FOXP3 following incubation with the agent, wherein the decrease indicates that the agent is a promoter of human Th-IL17+ cell differentiation in vitro or the change in expression of FOXP3 is an increase in expression of FOXP3 following incubation with the agent, wherein the increase indicates that the agent is an inhibitor of human Th-IL17+ cell differentiation in vitro.

5. The method of claim 1, wherein the agent is a small molecule; polypeptide; azole-containing compounds; cholesterol derivative compounds; retinoid derivative compounds; shRNA/siRNA; neutralizing/blocking antibodies; tryptophan derivative compounds; Vitamin D derivatives; or molecules known to inhibit of fever, inflammation, or regulatory T (Treg) cell differentiation.

* * * * *

UNITED STATES PATENT AND TRADEMARK OFFICE
CERTIFICATE OF CORRECTION

PATENT NO. : 8,404,482 B2
APPLICATION NO. : 13/473980
DATED : March 26, 2013
INVENTOR(S) : Nicolas Manel et al.

Page 1 of 1

It is certified that error appears in the above-identified patent and that said Letters Patent is hereby corrected as shown below:

In the Claims

Column 129, claim 1, line 29 after "adult humans," delete "cell" and insert --cells--.

Signed and Sealed this
Fourth Day of June, 2013

Teresa Stanek Rea
*Acting Director of the United States Patent and Trademark Office*

SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
tctgcaagac tcatcgccaa a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
cgaggatgag attgccctct a                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
ggacttcgag caagagatgg                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
agcactgtgt tggcgtacag                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ctcttccagc cttccttcct                                                20

<210> SEQ ID NO 6
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 6
cggtgccttt gactctcaga acaacaccg                                      29

<210> SEQ ID NO 7
<211> LENGTH: 24
<212> TYPE: DNA

```
<213> ORGANISM: Artificial Sequence
<220> FEATURE:
<223> OTHER INFORMATION: Synthetic oligonucleotide

<400> SEQUENCE: 7
tctttccaaa ttcaaacaca aagc                                          24

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ttgatgggaa gtatgccagc                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
ttttccgagg atgagattgc                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
ctttccacat gctggctaca                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
aagactcatc gccaaagcat                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
catgacttgc acctggaatg                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
gcttggaccc aaaccaagta                                               20
```

```
<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
tgattcatta caaggtggca a                                             21

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tgaagcttga cattggcatc                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
ttccttgagc attgatgcag                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
acctcccact ggaattacac                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
accaatccca aaaggtcctc                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ggggacagag ttcatgtggt                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 20
gcaatgagga ccctgagaga                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
tgcaaggctg caagaaaata                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ccagttcact gatggctttg                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
ggcagaaatt gagccactgt                                          20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
aaagaggcac tggcagaaaa                                          20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tttcaccagg caagtctcct                                          20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
ttctgccagc tccagaagat                                          20

<210> SEQ ID NO 27
<211> LENGTH: 20
<212> TYPE: DNA

<213> ORGANISM: Artificial Sequence
<220> FEATURE:
<223> OTHER INFORMATION: Synthetic oligonucleotide

<400> SEQUENCE: 27
ttgtggaagg tggtttcctc                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
tggtcagctt tttcctgctt                                          20

<210> SEQ ID NO 29
<211> LENGTH: 1557
<212> TYPE: DNA
<213> ORGANISM: Homo sapiens

<400> SEQUENCE: 29
atggacaggg ccccacagag acagcaccga gcctcacggg agctgctggc tgcaaagaag    60
acccacacct cacaaattga agtgatccct tgcaaaatct gtggggacaa gtcgtctggg   120
atccactacg gggttatcac ctgtgagggg tgcaagggct tcttccgccg gagccagcgc   180
tgtaacgcgg cctactcctg cacccgtcag cagaactgcc ccatcgaccg caccagccga   240
aaccgatgcc agcactgccg cctgcagaaa tgcctggcgc tgggcatgtc ccgagatgct   300
gtcaagttcg gccgcatgtc caagaagcag agggacagcc tgcatgcaga agtgcagaaa   360
cagctgcagc agcggcaaca gcagcaacag gaaccagtgg tcaagacccc tccagcaggg   420
gcccaaggag cagataccct cacctacacc ttggggctcc agacgggca gctgccctg   480 ggctcctcgc ctgacctgcc tgaggcttct gcctgtcccc ctggcctcct gaaagcctca   540
ggctctgggc cctcatattc caacaacttg gccaaggcag ggctcaatgg ggcctcatgc   600 cacctt gaat acagccctga gcggggcaag gctgagggca gagagagctt ctatagcaca   660
ggcagccagc tgaccccctga ccgatgtgga cttcgttttg aggaacacag gcatcctggg   720
cttggggaac tgggacaggg cccagacagc tacggcagcc ccagtttccg cagcacaccg   780
gaggcaccct atgcctccct gacagagata gagcacctgg tgcagagcgt ctgcaagtcc   840
tacagggaga catgccagct gcggctggag gacctgctgc ggcagcgctc caacatcttc   900
tcccgggagg aagtgactgg ctaccagagg aagtccatgt gggagatgtg ggaacggtgt   960
gcccaccacc tcaccgaggc cattcagtac gtggtggagt cgccaagag gctctcaggc  1020 tttatggagc tctgccagaa tgaccagatt gtgcttctca agcaggagc aatggaagtg  1080 gtgctggtta ggatgtgccg ggcctacaat gctgacaacc gcacggtctt ttttgaaggc  1140
aaatacggtg gcatggagct gttccgagcc ttgggctgca gcgagctcat cagctccatc  1200
tttgacttct cccactccct aagtgccttg cacttttccg aggatgagat tgccctctac  1260
acagcccttg ttctcatcaa tgcccatcgg ccagggctcc aagagaaaag gaaagtagaa  1320
cagctgcagt acaatctgga gctggccttt catcatcatc tctgcaagac tcatcgccaa  1380
agcatcctgg caaagctgcc acccaagggg aagcttcgga gcctgtgtag ccagcatgtg  1440
gaaaggctgc agatcttcca gcacctccac cccatcgtgg tccaagccgc tttccctcca  1500
ctctacaagg agctcttcag cactgaaacc gagtcacctg tggggctgtc caagtga     1557

-continued

<210> SEQ ID NO 30
<211> LENGTH: 518
<212> TYPE: PRT
<213> ORGANISM: Homo sapiens

<400> SEQUENCE: 30

```
Met Asp Arg Ala Pro Gln Arg His Arg Ala Ser Arg Glu Leu Leu
 1               5                  10                  15

Ala Ala Lys Lys Thr His Thr Ser Gln Ile Glu Val Ile Pro Cys Lys
            20                  25                  30

Ile Cys Gly Asp Lys Ser Ser Gly Ile His Tyr Gly Val Ile Thr Cys
                35                  40                  45

Glu Gly Cys Lys Gly Phe Phe Arg Arg Ser Gln Arg Cys Asn Ala Ala
        50                  55                  60

Tyr Ser Cys Thr Arg Gln Gln Asn Cys Pro Ile Asp Arg Thr Ser Arg
 65                 70                  75                  80

Asn Arg Cys Gln His Cys Arg Leu Gln Lys Cys Leu Ala Leu Gly Met
                85                  90                  95

Ser Arg Asp Ala Val Lys Phe Gly Arg Met Ser Lys Lys Gln Arg Asp
            100                 105                 110

Ser Leu His Ala Glu Val Gln Lys Gln Leu Gln Gln Arg Gln Gln Gln
        115                 120                 125

Gln Gln Glu Pro Val Val Lys Thr Pro Pro Ala Gly Ala Gln Gly Ala
130                 135                 140

Asp Thr Leu Thr Tyr Thr Leu Gly Leu Pro Asp Gly Gln Leu Pro Leu
145                 150                 155                 160

Gly Ser Ser Pro Asp Leu Pro Glu Ala Ser Ala Cys Pro Pro Gly Leu
                165                 170                 175

Leu Lys Ala Ser Gly Ser Gly Pro Ser Tyr Ser Asn Asn Leu Ala Lys
            180                 185                 190

Ala Gly Leu Asn Gly Ala Ser Cys His Leu Glu Tyr Ser Pro Glu Arg
        195                 200                 205

Gly Lys Ala Glu Gly Arg Glu Ser Phe Tyr Ser Thr Gly Ser Gln Leu
    210                 215                 220

Thr Pro Asp Arg Cys Gly Leu Arg Phe Glu Glu His Arg His Pro Gly
225                 230                 235                 240

Leu Gly Glu Leu Gly Gln Gly Pro Asp Ser Tyr Gly Ser Pro Ser Phe
                245                 250                 255

Arg Ser Thr Pro Glu Ala Pro Tyr Ala Ser Leu Thr Glu Ile Glu His
            260                 265                 270

Leu Val Gln Ser Val Cys Lys Ser Tyr Arg Glu Thr Cys Gln Leu Arg
        275                 280                 285

Leu Glu Asp Leu Leu Arg Gln Arg Ser Asn Ile Phe Ser Arg Glu Glu
    290                 295                 300

Val Thr Gly Tyr Gln Arg Lys Ser Met Trp Glu Met Trp Glu Arg Cys
305                 310                 315                 320

Ala His His Leu Thr Glu Ala Ile Gln Tyr Val Val Glu Phe Ala Lys
                325                 330                 335

Arg Leu Ser Gly Phe Met Glu Leu Cys Gln Asn Asp Gln Ile Val Leu
            340                 345                 350

Leu Lys Ala Gly Ala Met Glu Val Val Leu Val Arg Met Cys Arg Ala
        355                 360                 365

Tyr Asn Ala Asp Asn Arg Thr Val Phe Phe Glu Gly Lys Tyr Gly Gly
    370                 375                 380
```

```
Met Glu Leu Phe Arg Ala Leu Gly Cys Ser Glu Leu Ile Ser Ser Ile
385                 390                 395                 400

Phe Asp Phe Ser His Ser Leu Ser Ala Leu His Phe Ser Glu Asp Glu
            405                 410                 415

Ile Ala Leu Tyr Thr Ala Leu Val Leu Ile Asn Ala His Arg Pro Gly
                420                 425                 430

Leu Gln Glu Lys Arg Lys Val Glu Gln Leu Gln Tyr Asn Leu Glu Leu
            435                 440                 445

Ala Phe His His His Leu Cys Lys Thr His Arg Gln Ser Ile Leu Ala
            450                 455                 460

Lys Leu Pro Pro Lys Gly Lys Leu Arg Ser Leu Cys Ser Gln His Val
465                 470                 475                 480

Glu Arg Leu Gln Ile Phe Gln His Leu His Pro Ile Val Val Gln Ala
                485                 490                 495

Ala Phe Pro Pro Leu Tyr Lys Glu Leu Phe Ser Thr Glu Thr Glu Ser
                500                 505                 510

Pro Val Gly Leu Ser Lys
            515

<210> SEQ ID NO 31
<211> LENGTH: 1494
<212> TYPE: DNA
<213> ORGANISM: Homo sapiens

<400> SEQUENCE: 31
atgagaacac aaattgaagt gatcccttgc aaaatctgtg ggacaagtc gtctgggatc      60 cactacgggg ttatcacctg tgaggggtgc aagggcttct ccgccggag ccagcgctgt    120 aacgcggcct actcctgcac ccgtcagcag aactgcccca tcgaccgcac agccgaaac    180 cgatgccagc actgccgcct gcagaaatgc ctggcgctgg gcatgtcccg agatgctgtc    240
aagttcggcc gcatgtccaa gaagcagagg gacagcctgc atgcagaagt gcagaaacag    300
ctgcagcagc ggcaacagca gcaacaggaa ccagtggtca agacccctcc agcaggggcc    360
caaggagcag ataccctcac ctacaccttg gggctcccag acgggcagct gcccctgggc    420
tcctcgcctg acctgcctga ggcttctgcc tgtcccctg gcctcctgaa agcctcaggc    480
tctgggccct catattccaa caacttggcc aaggcagggc tcaatggggc tcatgccac    540 cttgaataca gccctgagcg gggcaaggct gagggcagag agagcttcta tagcacaggc    600
agccagctga ccctgaccg atgtggactt cgttttgagg aacacaggca tcctgggctt    660
ggggaactgg acagggccc agacagctac ggcagcccca gtttccgcag cacaccggag    720
gcaccctatg cctccctgac agagatagag cacctggtgc agagcgtctg caagtcctac    780
agggagacat gccagctgcg gctggaggac ctgctgcggc agcgctccaa catcttctcc    840
cgggaggaag tgactggcta ccagaggaag tccatgtggg agatgtggga acggtgtgcc    900
caccacctca ccgaggccat tcagtacgtg gtggagttcg ccaagaggct ctcaggcttt    960
atggagctct gccagaatga ccagattgtg cttctcaaag caggagcaat ggaagtggtg   1020
ctggttagga tgtgccgggc ctacaatgct gacaaccgca cggtcttttt tgaaggcaaa   1080
tacggtggca tggagctgtt ccgagccttg ggctgcagcg agctcatcag ctccatcttt   1140
gacttctccc actccctaag tgccttgcac ttttccgagg atgagattgc cctctacaca   1200
gcccttgttc tcatcaatgc ccatcggcca gggctccaag agaaaaggaa agtagaacag   1260
ctgcagtaca tctgagct ggccttcat catcatctct gcaagactca tcgccaaagc    1320
atcctggcaa agctgccacc caaggggaag cttcggagcc tgtgtagcca gcatgtggaa   1380
```

```
aggctgcaga tcttccagca cctccacccc atcgtggtcc aagccgcttt ccctccactc      1440
tacaaggagc tcttcagcac tgaaaccgag tcacctgtgg ggctgtccaa gtga            1494
```

<210> SEQ ID NO 32
<211> LENGTH: 497
<212> TYPE: PRT
<213> ORGANISM: Homo sapiens

<400> SEQUENCE: 32

```
Met Arg Thr Gln Ile Glu Val Ile Pro Cys Lys Ile Cys Gly Asp Lys
 1               5                  10                  15

Ser Ser Gly Ile His Tyr Gly Val Ile Thr Cys Glu Gly Cys Lys Gly
            20                  25                  30

Phe Phe Arg Arg Ser Gln Arg Cys Asn Ala Ala Tyr Ser Cys Thr Arg
        35                  40                  45

Gln Gln Asn Cys Pro Ile Asp Arg Thr Ser Arg Asn Arg Cys Gln His
    50                  55                  60

Cys Arg Leu Gln Lys Cys Leu Ala Leu Gly Met Ser Arg Asp Ala Val
65                  70                  75                  80

Lys Phe Gly Arg Met Ser Lys Lys Gln Arg Asp Ser Leu His Ala Glu
                85                  90                  95

Val Gln Lys Gln Leu Gln Gln Arg Gln Gln Gln Gln Glu Pro Val
            100                 105                 110

Val Lys Thr Pro Pro Ala Gly Ala Gln Gly Ala Asp Thr Leu Thr Tyr
        115                 120                 125

Thr Leu Gly Leu Pro Asp Gly Gln Leu Pro Leu Gly Ser Ser Pro Asp
    130                 135                 140

Leu Pro Glu Ala Ser Ala Cys Pro Pro Gly Leu Leu Lys Ala Ser Gly
145                 150                 155                 160

Ser Gly Pro Ser Tyr Ser Asn Asn Leu Ala Lys Ala Gly Leu Asn Gly
                165                 170                 175

Ala Ser Cys His Leu Glu Tyr Ser Pro Glu Arg Gly Lys Ala Glu Gly
            180                 185                 190

Arg Glu Ser Phe Tyr Ser Thr Gly Ser Gln Leu Thr Pro Asp Arg Cys
        195                 200                 205

Gly Leu Arg Phe Glu Glu His Arg His Pro Gly Leu Gly Glu Leu Gly
    210                 215                 220

Gln Gly Pro Asp Ser Tyr Gly Ser Pro Ser Phe Arg Ser Thr Pro Glu
225                 230                 235                 240

Ala Pro Tyr Ala Ser Leu Thr Glu Ile Glu His Leu Val Gln Ser Val
                245                 250                 255

Cys Lys Ser Tyr Arg Glu Thr Cys Gln Leu Arg Leu Glu Asp Leu Leu
            260                 265                 270

Arg Gln Arg Ser Asn Ile Phe Ser Arg Glu Glu Val Thr Gly Tyr Gln
        275                 280                 285

Arg Lys Ser Met Trp Glu Met Trp Glu Arg Cys Ala His His Leu Thr
    290                 295                 300

Glu Ala Ile Gln Tyr Val Val Glu Phe Ala Lys Arg Leu Ser Gly Phe
305                 310                 315                 320

Met Glu Leu Cys Gln Asn Asp Gln Ile Val Leu Leu Lys Ala Gly Ala
                325                 330                 335

Met Glu Val Val Leu Val Arg Met Cys Arg Ala Tyr Asn Ala Asp Asn
            340                 345                 350

Arg Thr Val Phe Phe Glu Gly Lys Tyr Gly Gly Met Glu Leu Phe Arg
```

| | | | | | | | | | | | |
|---|---|---|---|---|---|---|---|---|---|---|---|
| | | 355 | | | | 360 | | | | 365 | |
| Ala | Leu | Gly | Cys | Ser | Glu | Leu | Ile | Ser | Ser | Ile | Phe | Asp | Phe | Ser | His |
| | 370 | | | | | 375 | | | | | 380 | | | | |

Ala Leu Gly Cys Ser Glu Leu Ile Ser Ser Ile Phe Asp Phe Ser His
                370                     375                     380

Ser Leu Ser Ala Leu His Phe Ser Glu Asp Glu Ile Ala Leu Tyr Thr
385                     390                     395                     400

Ala Leu Val Leu Ile Asn Ala His Arg Pro Gly Leu Gln Glu Lys Arg
                    405                     410                     415

Lys Val Glu Gln Leu Gln Tyr Asn Leu Glu Leu Ala Phe His His
                420                     425                     430

Leu Cys Lys Thr His Arg Gln Ser Ile Leu Ala Lys Leu Pro Pro Lys
                435                     440                     445

Gly Lys Leu Arg Ser Leu Cys Ser Gln His Val Glu Arg Leu Gln Ile
        450                     455                     460

Phe Gln His Leu His Pro Ile Val Val Gln Ala Ala Phe Pro Pro Leu
465                     470                     475                     480

Tyr Lys Glu Leu Phe Ser Thr Glu Thr Glu Ser Pro Val Gly Leu Ser
                    485                     490                     495

Lys

<210> SEQ ID NO 33
<211> LENGTH: 1551
<212> TYPE: DNA
<213> ORGANISM: Mus musculus

<400> SEQUENCE: 33

```
atggacaggg ccccacagag acaccaccgg acatctcggg agctgctggc tgcaaagaag      60
acccacacct cacaaattga agtgatccct tgcaagatct gtggggacaa gtcatctggg     120
atccactacg gggttatcac ctgtgagggg tgcaaggggc tcttccgccg cagccagcag     180
tgtaatgtgg cctactcctg cacgcgtcag cagaactgcc ccattgaccg aaccagccgc     240
aaccgatgcc agcattgccg cctgcagaag tgcctggctc tgggcatgtc ccgagatgct     300
gtcaagtttg gccgaatgtc caagaagcag agggacagtc tacatgcaga agtgcagaaa     360
caactgcaac agcagcagca acaggaacaa gtggccaaga ctcctccagc tgggagccgc     420
ggagcagaca cacttacata cactttaggg ctctcagatg gcagctacc actgggcgcc      480
tcacctgacc tacccgaggc ctctgcttgt cccctggcc tcctgagagc tcaggctct      540
ggcccaccat attccaatac cttggccaaa acagaggtcc agggggcctc ctgccaccgtt    600
gagtatagtc cagaacgagg caaagctgaa ggcagagaca gcatctatag cactgacggc     660
caacttactc ttggaagatg tggacttcgt tttgaggaaa ccaggcatcc tgaacttggg     720
gaaccagaac agggtccaga cagccactgc attcccagtt ctgcagtgc cccagaggta      780
ccatatgcct ctctgacaga catagagtac ctggtacaga atgtctgcaa gtccttccga     840
gagacatgcc agctgcgact ggaggaccct ctacggcagc gcaccaacct cttttcacgg     900
gaggaggtga ccagctacca gaggaagtca atgtgggaga tgtgggagcg ctgtgcccac     960
cacctcactg aggccattca gtatgtggtg gagtttgcca gcggctttc aggcttcatg     1020
gagctctgcc agaatgacca gatcatacta ctgacagcag gagcaatgga agtcgtccta    1080
gtcagaatgt gcagggccta caatgccaac aaccacacag tcttttttga aggcaaatac    1140
ggtggtgtgg agctgtttcg agccttgggc tgcagcgagc tcatcagctc catatttgac    1200
ttttccccact tcctcagcgc cctgtgtttt tctgaggatg agattgccct ctacacggcc   1260
ctggttctca tcaatgccaa ccgtcctggg ctccaagaga agaggagagt ggaacatctg    1320
```

```
caatacaatt tggaactggc tttccatcat catctctgca agactcatcg acaaggcctc    1380
ctagccaagc tgccacccaa aggaaaactc cggagcctgt gcagccaaca tgtggaaaag    1440
ctgcagatct tccagcacct ccaccccatc gtggtccaag ccgccttccc gccactctat    1500
aaggaactct tcagcactga tgttgaatcc cctgaggggc tgtcaaagtg a             1551
```

<210> SEQ ID NO 34
<211> LENGTH: 516
<212> TYPE: PRT
<213> ORGANISM: Mus musculus

<400> SEQUENCE: 34

```
Met Asp Arg Ala Pro Gln Arg His His Arg Thr Ser Arg Glu Leu Leu
 1               5                  10                  15

Ala Ala Lys Lys Thr His Thr Ser Gln Ile Glu Val Ile Pro Cys Lys
            20                  25                  30

Ile Cys Gly Asp Lys Ser Ser Gly Ile His Tyr Gly Val Ile Thr Cys
        35                  40                  45

Glu Gly Cys Lys Gly Phe Phe Arg Arg Ser Gln Gln Cys Asn Val Ala
    50                  55                  60

Tyr Ser Cys Thr Arg Gln Gln Asn Cys Pro Ile Asp Arg Thr Ser Arg
65                  70                  75                  80

Asn Arg Cys Gln His Cys Arg Leu Gln Lys Cys Leu Ala Leu Gly Met
                85                  90                  95

Ser Arg Asp Ala Val Lys Phe Gly Arg Met Ser Lys Lys Gln Arg Asp
            100                 105                 110

Ser Leu His Ala Glu Val Gln Lys Gln Leu Gln Gln Gln Gln Gln Gln
        115                 120                 125

Glu Gln Val Ala Lys Thr Pro Pro Ala Gly Ser Arg Gly Ala Asp Thr
    130                 135                 140

Leu Thr Tyr Thr Leu Gly Leu Ser Asp Gly Gln Leu Pro Leu Gly Ala
145                 150                 155                 160

Ser Pro Asp Leu Pro Glu Ala Ser Ala Cys Pro Pro Gly Leu Leu Arg
                165                 170                 175

Ala Ser Gly Ser Gly Pro Pro Tyr Ser Asn Thr Leu Ala Lys Thr Glu
            180                 185                 190

Val Gln Gly Ala Ser Cys His Leu Glu Tyr Ser Pro Gly Arg Gly Lys
        195                 200                 205

Ala Glu Gly Arg Asp Ser Ile Tyr Ser Thr Asp Gly Gln Leu Thr Leu
    210                 215                 220

Gly Arg Cys Gly Leu Arg Phe Glu Glu Thr Arg His Pro Glu Leu Gly
225                 230                 235                 240

Glu Pro Glu Gln Gly Pro Asp Ser His Cys Ile Pro Ser Phe Cys Ser
                245                 250                 255

Ala Pro Glu Val Pro Tyr Ala Ser Leu Thr Asp Ile Glu Tyr Leu Val
            260                 265                 270

Gln Asn Val Cys Lys Ser Phe Arg Glu Thr Cys Gln Leu Arg Leu Glu
        275                 280                 285

Asp Leu Leu Arg Gln Arg Thr Asn Leu Phe Ser Arg Glu Glu Val Thr
    290                 295                 300

Ser Tyr Gln Arg Lys Ser Met Trp Glu Met Trp Glu Arg Cys Ala His
305                 310                 315                 320

His Leu Thr Glu Ala Ile Gln Tyr Val Val Glu Phe Ala Lys Arg Leu
                325                 330                 335

Ser Gly Phe Met Glu Leu Cys Gln Asn Asp Gln Ile Ile Leu Leu Thr
```

```
                    340             345             350
Ala Gly Ala Met Glu Val Val Leu Val Arg Met Cys Arg Ala Tyr Asn
                355             360             365
Ala Asn Asn His Thr Val Phe Phe Glu Gly Lys Tyr Gly Gly Val Glu
            370             375             380
Leu Phe Arg Ala Leu Gly Cys Ser Glu Leu Ile Ser Ser Ile Phe Asp
385             390             395             400
Phe Ser His Phe Leu Ser Ala Leu Cys Phe Ser Glu Asp Glu Ile Ala
                405             410             415
Leu Tyr Thr Ala Leu Val Leu Ile Asn Ala Asn Arg Pro Gly Leu Gln
                420             425             430
Glu Lys Arg Arg Val Glu His Leu Gln Tyr Asn Leu Glu Leu Ala Phe
                435             440             445
His His His Leu Cys Lys Thr His Arg Gln Gly Leu Leu Ala Lys Leu
            450             455             460
Pro Pro Lys Gly Lys Leu Arg Ser Leu Cys Ser Gln His Val Glu Lys
465             470             475             480
Leu Gln Ile Phe Gln His Leu His Pro Ile Val Val Gln Ala Ala Phe
                485             490             495
Pro Pro Leu Tyr Lys Glu Leu Phe Ser Thr Asp Val Glu Ser Pro Glu
            500             505             510
Gly Leu Ser Lys
        515

<210> SEQ ID NO 35
<211> LENGTH: 1488
<212> TYPE: DNA
<213> ORGANISM: Mus musculus

<400> SEQUENCE: 35
atgagaacac aaattgaagt gatcccttgc aagatctgtg gggacaagtc atctgggatc      60
cactacgggg ttatcacctg tgaggggtgc aagggcttct tccgccgcag ccagcagtgt     120
aatgtggcct actcctgcac gcgtcagcag aactgcccca ttgaccgaac cagccgcaac     180
cgatgccagc attgccgcct gcagaagtgc ctggctctgg gcatgtcccg agatgctgtc     240
aagtttggcc gaatgtccaa gaagcagagg gacagtctac atgcagaagt gcagaaacaa     300
ctgcaacagc agcagcaaca ggaacaagtg gccaagactc tccagctgga gccgcggga     360 gcagacacac ttacatacac tttagggctc tcagatgggc agctaccact gggcgcctca     420
cctgacctac ccgaggcctc tgcttgtccc cctggcctcc tgagagcctc aggctctggc     480
ccaccatatt ccaatacctt ggccaaaaca gaggtccagg gggcctcctg ccaccttgag     540
tatagtccag aacgaggcaa agctgaaggc agagacagca tctatagcac tgacggccaa     600
cttactcttg gaagatgtgg acttcgtttt gaggaaacca ggcatcctga acttggggaa     660
ccagaacagg gtccagacag ccactgcatt cccagtttct gcagtgcccc agaggtacca     720
tatgcctctc tgacagacat agagtacctg gtacagaatg tctgcaagtc cttccgagag     780
acatgccagc tgcgactgga ggaccttcta cggcagcgca ccaacctctt tcacggggag     840
gaggtgacca gctaccagag gaagtcaatg tgggagatgt gggagcgctg tgcccaccac     900
ctcactgagg ccattcagta tgtggtggag tttgccaagc ggctttcagg cttcatggag     960
ctctgccaga tgaccagat catactactg aaagcaggag caatggaagt cgtcctagtc    1020
agaatgtgca gggcctacaa tgccaacaac cacacagtct tttttgaagg caaatacggt    1080
ggtgtggagc tgtttcgagc cttgggctgc agcgagctca tcagctccat atttgacttt    1140
```

```
tcccacttcc tcagcgccct gtgtttttct gaggatgaga ttgccctcta cacggccctg    1200
gttctcatca atgccaaccg tcctgggctc aagagaaga ggagagtgga acatctgcaa    1260
tacaatttgg aactggcttt ccatcatcat ctctgcaaga ctcatcgaca aggcctccta    1320
gccaagctgc cacccaaagg aaaactccgg agcctgtgca gccaacatgt ggaaaagctg    1380
cagatcttcc agcacctcca ccccatcgtg gtccaagccg ccttccctcc actctataag    1440
gaactcttca gcactgatgt tgaatcccct gagggctgt caaagtga                  1488

<210> SEQ ID NO 36
<211> LENGTH: 495
<212> TYPE: PRT
<213> ORGANISM: Mus musculus

<400> SEQUENCE: 36
```

Met Arg Thr Gln Ile Glu Val Ile Pro Cys Lys Ile Cys Gly Asp Lys
 1               5                  10                  15

Ser Ser Gly Ile His Tyr Gly Val Ile Thr Cys Glu Gly Cys Lys Gly
            20                  25                  30

Phe Phe Arg Arg Ser Gln Gln Cys Asn Val Ala Tyr Ser Cys Thr Arg
        35                  40                  45

Gln Gln Asn Cys Pro Ile Asp Arg Thr Ser Arg Asn Arg Cys Gln His
    50                  55                  60

Cys Arg Leu Gln Lys Cys Leu Ala Leu Gly Met Ser Arg Asp Ala Val
65                  70                  75                  80

Lys Phe Gly Arg Met Ser Lys Lys Gln Arg Asp Ser Leu His Ala Glu
                85                  90                  95

Val Gln Lys Gln Leu Gln Gln Gln Gln Gln Glu Gln Val Ala Lys
            100                 105                 110

Thr Pro Pro Ala Gly Ser Arg Gly Ala Asp Thr Leu Thr Tyr Thr Leu
        115                 120                 125

Gly Leu Ser Asp Gly Gln Leu Pro Leu Gly Ala Ser Pro Asp Leu Pro
    130                 135                 140

Glu Ala Ser Ala Cys Pro Pro Gly Leu Leu Arg Ala Ser Gly Ser Gly
145                 150                 155                 160

Pro Pro Tyr Ser Asn Thr Leu Ala Lys Thr Glu Val Gln Gly Ala Ser
                165                 170                 175

Cys His Leu Glu Tyr Ser Pro Glu Arg Gly Lys Ala Glu Gly Arg Asp
            180                 185                 190

Ser Ile Tyr Ser Thr Asp Gly Gln Leu Thr Leu Gly Arg Cys Gly Leu
        195                 200                 205

Arg Phe Glu Glu Thr Arg His Pro Glu Leu Gly Glu Pro Glu Gln Gly
    210                 215                 220

Pro Asp Ser His Cys Ile Pro Ser Phe Cys Ser Ala Pro Glu Val Pro
225                 230                 235                 240

Tyr Ala Ser Leu Thr Asp Ile Glu Tyr Leu Val Gln Asn Val Cys Lys
                245                 250                 255

Ser Phe Arg Glu Thr Cys Gln Leu Arg Leu Glu Asp Leu Leu Arg Gln
            260                 265                 270

Arg Thr Asn Leu Phe Ser Arg Glu Glu Val Thr Ser Tyr Gln Arg Lys
        275                 280                 285

Ser Met Trp Glu Met Trp Glu Arg Cys Ala His His Leu Thr Glu Ala
    290                 295                 300

Ile Gln Tyr Val Val Glu Phe Ala Lys Arg Leu Ser Gly Phe Met Glu
305                 310                 315                 320

```
Leu Cys Gln Asn Asp Gln Ile Ile Leu Leu Lys Ala Gly Ala Met Glu
            325                 330                 335

Val Val Leu Val Arg Met Cys Arg Ala Tyr Asn Ala Asn Asn His Thr
            340                 345                 350

Val Phe Phe Glu Gly Lys Tyr Gly Gly Val Glu Leu Phe Arg Ala Leu
            355                 360                 365

Gly Cys Ser Glu Leu Ile Ser Ser Ile Phe Asp Phe Ser His Phe Leu
    370                 375                 380

Ser Ala Leu Cys Phe Ser Glu Asp Glu Ile Ala Leu Tyr Thr Ala Leu
385                 390                 395                 400

Val Leu Ile Asn Ala Asn Arg Pro Gly Leu Gln Glu Lys Arg Arg Val
                405                 410                 415

Glu His Leu Gln Tyr Asn Leu Glu Leu Ala Phe His His His Leu Cys
            420                 425                 430

Lys Thr His Arg Gln Gly Leu Leu Ala Lys Leu Pro Pro Lys Gly Lys
            435                 440                 445

Leu Arg Ser Leu Cys Ser Gln His Val Glu Lys Leu Gln Ile Phe Gln
            450                 455                 460

His Leu His Pro Ile Val Val Gln Ala Ala Phe Pro Pro Leu Tyr Lys
465                 470                 475                 480

Glu Leu Phe Ser Thr Asp Val Glu Ser Pro Glu Gly Leu Ser Lys
                485                 490                 495

<210> SEQ ID NO 37
<211> LENGTH: 1687
<212> TYPE: DNA
<213> ORGANISM: Homo sapiens

<400> SEQUENCE: 37
tgtggctcgg gcggcggcgg cgcggcggcg gcagagggggg ctccggggtc ggaccatccg      60
ctctccctgc gctctccgca ccgcgcttaa atgatgtatt ttgtgatcgc agcgatgaaa     120
gctcaaattg aaattattcc atgcaagatc tgtggagaca atcatcagg aatccattat      180 ggtgtcatta catgtgaagg ctgcaagggc tttttcagga aagtcagca aagcaatgcc      240 acctactcct gtcctcgtca aagaactgtt tgattgatc gaaccagtag aaaccgctgc      300
caacactgtc gattacagaa atgccttgcc gtagggatgt ctcgagatgc tgtaaaattt      360
ggccgaatgt caaaaagca gagagacagc ttgtatgcag aagtacagaa acaccggatg      420
cagcagcagc agcgcgacca ccagcagcag cctggagagg ctgagccgct gacgccacc      480 tacaacatct cggccaacgg gctgacggaa cttcacgacg acctcagtaa ctacattgac     540
gggcacaccc ctgaggggag taaggcagac tccgccgtca gcagcttcta cctggacata     600
cagccttccc cagaccagtc aggtcttgat atcaatggaa tcaaaccaga accaatatgt     660
gactacacac cagcatcagg cttctttccc tactgttcgt tcaccaacgg cgagacttcc     720
ccaactgtgt ccatggcaga attagaacac cttgcacaga atatctaa atcgcatctg      780 gaaacctgcc aatacttgag agaagagctc cagcagataa cgtggcagac cttttttacag      840 gaagaaattg agaactatca aaacaagcag cgggaggtga tgtggcaatt gtgtgccatc      900
aaaattacag aagctataca gtatgtggtg gagtttgcca aacgcattga tggatttatg      960
gaactgtgtc aaaatgatca aattgtgctt ctaaaagcag gttctctaga ggtggtgttt     1020
atcagaatgt gccgtgcctt tgactctcag aacaacaccg tgtactttga tgggaagtat     1080
gccagccccg acgtcttcaa atccttaggt tgtgaagact ttattagctt tgtgtttgaa     1140
```

-continued

```
tttggaaaga gtttatgttc tatgcacctg actgaagatg aaattgcatt attttctgca    1200
tttgtactga tgtcagcaga tcgctcatgg ctgcaagaaa aggtaaaaat tgaaaaactg    1260
caacagaaaa ttcagctagc tcttcaacac gtcctacaga agaatcaccg agaagatgga    1320
atactaacaa agttaatatg caaggtgtct acattaagag ccttatgtgg acgacataca    1380
gaaaagctaa tggcatttaa agcaatatac ccagacattg tgcgacttca ttttcctcca    1440
ttatacaagg agttgttcac ttcagaattt gagccagcaa tgcaaattga tgggtaaatg    1500
ttatcaccta agcacttcta gaatgtctga agtacaaaca tgaaaacaa acaaaaaaat    1560 taaccgagac actttatatg gccctgcaca gacctggagc gccacacact gcacatcttt    1620
tggtgatcgg ggtcaggcaa aggagggggaa acaatgaaaa caaataaagt tgaacttgtt    1680
tttctca                                                              1687

<210> SEQ ID NO 38
<211> LENGTH: 468
<212> TYPE: PRT
<213> ORGANISM: Homo sapiens

<400> SEQUENCE: 38

Met Met Tyr Phe Val Ile Ala Ala Met Lys Ala Gln Ile Glu Ile Ile
 1               5                  10                  15

Pro Cys Lys Ile Cys Gly Asp Lys Ser Ser Gly Ile His Tyr Gly Val
            20                  25                  30

Ile Thr Cys Glu Gly Cys Lys Gly Phe Phe Arg Arg Ser Gln Gln Ser
        35                  40                  45

Asn Ala Thr Tyr Ser Cys Pro Arg Gln Lys Asn Cys Leu Ile Asp Arg
    50                  55                  60

Thr Ser Arg Asn Arg Cys Gln His Cys Arg Leu Gln Lys Cys Leu Ala
65                  70                  75                  80

Val Gly Met Ser Arg Asp Ala Val Lys Phe Gly Arg Met Ser Lys Lys
                85                  90                  95

Gln Arg Asp Ser Leu Tyr Ala Glu Val Gln Lys His Arg Met Gln Gln
            100                 105                 110

Gln Gln Arg Asp His Gln Gln Pro Gly Glu Ala Glu Pro Leu Thr
        115                 120                 125

Pro Thr Tyr Asn Ile Ser Ala Asn Gly Leu Thr Glu Leu His Asp Asp
    130                 135                 140

Leu Ser Asn Tyr Ile Asp Gly His Thr Pro Glu Gly Ser Lys Ala Asp
145                 150                 155                 160

Ser Ala Val Ser Ser Phe Tyr Leu Asp Ile Gln Pro Ser Pro Asp Gln
                165                 170                 175

Ser Gly Leu Asp Ile Asn Gly Ile Lys Pro Glu Pro Ile Cys Asp Tyr
            180                 185                 190

Thr Pro Ala Ser Gly Phe Phe Pro Tyr Cys Ser Phe Thr Asn Gly Glu
        195                 200                 205

Thr Ser Pro Thr Val Ser Met Ala Glu Leu Glu His Leu Ala Gln Asn
    210                 215                 220

Ile Ser Lys Ser His Leu Glu Thr Cys Gln Tyr Leu Arg Glu Glu Leu
225                 230                 235                 240

Gln Gln Ile Thr Trp Gln Thr Phe Leu Gln Glu Ile Glu Asn Tyr
                245                 250                 255

Gln Asn Lys Gln Arg Glu Val Met Trp Gln Leu Cys Ala Ile Lys Ile
            260                 265                 270

Thr Glu Ala Ile Gln Tyr Val Val Glu Phe Ala Lys Arg Ile Asp Gly
```

```
                 275                 280                 285
Phe Met Glu Leu Cys Gln Asn Asp Gln Ile Val Leu Leu Lys Ala Gly
    290                 295                 300

Ser Leu Glu Val Val Phe Ile Arg Met Cys Arg Ala Phe Asp Ser Gln
305                 310                 315                 320

Asn Asn Thr Val Tyr Phe Asp Gly Lys Tyr Ala Ser Pro Asp Val Phe
                325                 330                 335

Lys Ser Leu Gly Cys Glu Asp Phe Ile Ser Phe Val Phe Glu Phe Gly
            340                 345                 350

Lys Ser Leu Cys Ser Met His Leu Thr Glu Asp Glu Ile Ala Leu Phe
        355                 360                 365

Ser Ala Phe Val Leu Met Ser Ala Asp Arg Ser Trp Leu Gln Glu Lys
    370                 375                 380

Val Lys Ile Glu Lys Leu Gln Gln Lys Ile Gln Leu Ala Leu Gln His
385                 390                 395                 400

Val Leu Gln Lys Asn His Arg Glu Asp Gly Ile Leu Thr Lys Leu Ile
                405                 410                 415

Cys Lys Val Ser Thr Leu Arg Ala Leu Cys Gly Arg His Thr Glu Lys
            420                 425                 430

Leu Met Ala Phe Lys Ala Ile Tyr Pro Asp Ile Val Arg Leu His Phe
        435                 440                 445

Pro Pro Leu Tyr Lys Glu Leu Phe Thr Ser Glu Phe Glu Pro Ala Met
    450                 455                 460

Gln Ile Asp Gly
465

<210> SEQ ID NO 39
<211> LENGTH: 3604
<212> TYPE: DNA
<213> ORGANISM: Homo sapiens

<400> SEQUENCE: 39
tctctcccct ctctttctct ctcgctgctc ccttcctccc tgtaactgaa cagtgaaaat       60
tcacattgtg gatccgctaa caggcacaga tgtcatgtga aaacgcacat gctctgccat      120
ccacaccgcc tttctttctt ttctttctgt ttccttttt  ccccttgtt ccttctccct      180 cttctttgta actaacaaaa ccaccaccaa ctcctcctcc tgctgctgcc cttcctcctc      240
ctcctcagtc caagtgatca caaaagaaat cttctgagcc ggaggcggtg gcatttttta      300
aaaagcaagc acattggaga gaagaaaaa  gaaaacaaa  accaaacaa  acccaggca      360 ccagacagcc agaacatttt tttttcaccc ttcctgaaaa caaacaaaca aacaaacaat      420
catcaaaaca gtcaccacca acatcaaaac tgttaacata gcggcggcgg cggcaaacgt      480
caccctgcag ccacggcgtc cgcctaaagg gatggttttc tcggcagagc agctcttcgc      540
cgaccacctt cttcactcgt gctgagcggg attttgggc  tctccggggt tcgggctggg      600
agcagcttca tgactacgcg gagcgggaga gcggccacac catgcgagca caaattgaag      660
tgataccatg caaattgt  ggcgataagt cctctgggat ccactacgga gtcatcacat      720
gtgaaggctg caagggattc tttaggagga gccagcagaa caatgcttct tattcctgcc      780
caaggcagag aaaactgttta attgacgaa  cgaacgaaa  ccgttgccaa cactgccgac      840
tgcagaagtg tcttgcccta ggaatgtcaa gagatgctgt gaagtttggg aggatgtcca      900
agaagcaaag ggacagcctg tatgctgagg tgcagaagca ccagcagcgg ctgcaggaac      960
agcggcagca gcagagtggg gaggcagaag cccttgccag ggtgtacagc agcagcatta     1020
```

```
gcaacggcct gagcaacctg aacaacgaga ccagcggcac ttatgccaac gggcacgtca    1080
ttgacctgcc caagtctgag ggttattaca acgtcgattc cggtcagccg tccccCgatc    1140
agtcaggact tgacatgact ggaatcaaac agataaagca agaacctatc tatgacctca    1200
catccgtacc caacttgttt acctatagct ctttcaacaa tgggcagtta gcaccaggga    1260
taaccatgac tgaaatcgac cgaattgcac agaacatcat taagtcccat ttggagacat    1320
gtcaatacac catggaagag ctgcaccagc tggcgtggca gacccacacc tatgaagaaa    1380
ttaaagcata tcaaagcaag tccagggaag cactgtggca acaatgtgcc atccagatca    1440
ctcacgccat ccaatacgtg gtggagtttg caaagcggat aacaggcttc atggagctct    1500
gtcaaaatga tcaaattcta cttctgaagt caggttgctt ggaagtggtt ttagtgagaa    1560
tgtgccgtgc cttcaaccca ttaaacaaca ctgttctgtt tgaaggaaaa tatggaggaa    1620
tgcaaatgtt caaagcctta ggttctgatg acctagtgaa tgaagcattt gactttgcaa    1680
agaatttgtg ttccttgcag ctgaccgagg aggagatcgc tttgttctca tctgctgttc    1740
tgatatctcc agaccgagcc tggcttatag aaccaaggaa agtccagaag cttcaggaaa    1800
aaatttattt tgcacttcaa catgtgattc agaagaatca cctggatgat gagaccttgg    1860
caaagttaat agccaagata ccaaccatca cggcagtttg caacttgcac ggggagaagc    1920
tgcaggtatt taagcaatct catccagaga tagtgaatac actgtttcct ccgttataca    1980
aggagctctt taatcctgac tgtgccaccg gctgcaaatg aaggggacaa gagaactgtc    2040
tcatagtcat ggaatgcatc accattaaga caaaagcaat gtgttcatga agacttaaga    2100
aaaatgtcac tactgcaaca ttaggaatgt cctgcactta atagaattat ttttcaccgc    2160
tacagtttga agaatgtaaa tatgcacctg agtggggctc ttttatttgt ttgtttgttt    2220
ttgaaatgac cataaatata caaatatagg acactgggtg ttatccttt tttaattta    2280 ttcgggtatg ttttgggaga caactgttta tagaatttta ttgtagatat atacaagaaa    2340
agagcggtac tttacatgat tactttttcct gttgattgtt caaatataat ttaagaaaat    2400
tccacttaat aggcttacct atttctatgt ttttaggtag ttgatgcatg tgtaaatttg    2460
tagctgtctt ggaaagtact gtgcatgtat gtaataagta tataatatgt gagaatatta    2520
tatatgacta ttacttatac atgcacatgc actgtggctt aaataccata cctactagca    2580
atggaggttc agtcaggctc tcttctatga tttaccttct gtgttatatg ttacctttat    2640
gttagacaat caggattttg ttttcccagc cagagttttc atctatagtc aatggcagga    2700
cggtaccaac tcagagttaa gtctacaaag gaataaacat aatgtgtggc ctctatatac    2760
aaactctatt tctgtcaatg acatcaaagc cttgtcaaga tggttcatat tgggaaggag    2820
acagtatttt aagccatttt cctgtttcaa gaattaggcc acagataaca ttgcaaggtc    2880
caagactttt ttgaccaaac agtagatatt ttctattttt caccagaaca cataaaaaca    2940 cttttttct tttggatttc tggttgtgaa acaagcttga tttcagtgct tattgtgtct    3000
tcaactgaaa aatacaatct gtggattatg actaccagca attttttct aggaaagtta    3060 aaagaataaa tcagaaccca gggcaacaat gccatttcat gtaaacattt tctctctcac    3120
catgttttgg caagaaaagg tagaaagaga agacccagag tgaagaagta attctttata    3180
ttccttcctt taatgtattt gttaggaaaa gtggcaataa aggggaggc atattataaa    3240 atgctataat ataaaaatgt agcaaaaact tgacagacta gaaaaaaaaa gatctgtgtt    3300
attctaggga actaatgtac cccaaagcca aaactaattc ctgtgaagtt tacagttaca    3360
tcatccattt accctagaat tattttttta gcaacttttta gaaataaaga atacaactgt    3420
```

```
gacattagga tcagagattt tagacttcct tgtacaaatt ctcacttctc cacctgctca    3480
ccaatgaaat taatcataag aaaagcatat attccaagaa atttgttctg cctgtgtcct    3540
ggaggcctat acctctgtta ttttctgata caaataaaa cttaaaaaaa agaaaacaag    3600
ctaa                                                                  3604
```

<210> SEQ ID NO 40
<211> LENGTH: 459
<212> TYPE: PRT
<213> ORGANISM: Homo sapiens

<400> SEQUENCE: 40

```
Met Arg Ala Gln Ile Glu Val Ile Pro Cys Lys Ile Cys Gly Asp Lys
 1               5                  10                  15

Ser Ser Gly Ile His Tyr Gly Val Ile Thr Cys Glu Gly Cys Lys Gly
            20                  25                  30

Phe Phe Arg Arg Ser Gln Gln Asn Asn Ala Ser Tyr Ser Cys Pro Arg
        35                  40                  45

Gln Arg Asn Cys Leu Ile Asp Arg Thr Asn Arg Asn Arg Cys Gln His
    50                  55                  60

Cys Arg Leu Gln Lys Cys Leu Ala Leu Gly Met Ser Arg Asp Ala Val
65                  70                  75                  80

Lys Phe Gly Arg Met Ser Lys Lys Gln Arg Asp Ser Leu Tyr Ala Glu
                85                  90                  95

Val Gln Lys His Gln Gln Arg Leu Gln Glu Gln Arg Gln Gln Gln Ser
            100                 105                 110

Gly Glu Ala Glu Ala Leu Ala Arg Val Tyr Ser Ser Ser Ile Ser Asn
        115                 120                 125

Gly Leu Ser Asn Leu Asn Asn Glu Thr Ser Gly Thr Tyr Ala Asn Gly
    130                 135                 140

His Val Ile Asp Leu Pro Lys Ser Glu Gly Tyr Tyr Asn Val Asp Ser
145                 150                 155                 160

Gly Gln Pro Ser Pro Asp Gln Ser Gly Leu Asp Met Thr Gly Ile Lys
                165                 170                 175

Gln Ile Lys Gln Glu Pro Ile Tyr Asp Leu Thr Ser Val Pro Asn Leu
            180                 185                 190

Phe Thr Tyr Ser Ser Phe Asn Asn Gly Gln Leu Ala Pro Gly Ile Thr
        195                 200                 205

Met Thr Glu Ile Asp Arg Ile Ala Gln Asn Ile Ile Lys Ser His Leu
    210                 215                 220

Glu Thr Cys Gln Tyr Thr Met Glu Glu Leu His Gln Leu Ala Trp Gln
225                 230                 235                 240

Thr His Thr Tyr Glu Glu Ile Lys Ala Tyr Gln Ser Lys Ser Arg Glu
                245                 250                 255

Ala Leu Trp Gln Gln Cys Ala Ile Gln Ile Thr His Ala Ile Gln Tyr
            260                 265                 270

Val Val Glu Phe Ala Lys Arg Ile Thr Gly Phe Met Glu Leu Cys Gln
        275                 280                 285

Asn Asp Gln Ile Leu Leu Leu Lys Ser Gly Cys Leu Glu Val Val Leu
    290                 295                 300

Val Arg Met Cys Arg Ala Phe Asn Pro Leu Asn Asn Thr Val Leu Phe
305                 310                 315                 320

Glu Gly Lys Tyr Gly Gly Met Gln Met Phe Lys Ala Leu Gly Ser Asp
                325                 330                 335

Asp Leu Val Asn Glu Ala Phe Asp Phe Ala Lys Asn Leu Cys Ser Leu
```

-continued

```
            340                 345                 350
Gln Leu Thr Glu Glu Glu Ile Ala Leu Phe Ser Ser Ala Val Leu Ile
        355                 360                 365

Ser Pro Asp Arg Ala Trp Leu Ile Glu Pro Arg Lys Val Gln Lys Leu
        370                 375                 380

Gln Glu Lys Ile Tyr Phe Ala Leu Gln His Val Ile Gln Lys Asn His
385                     390                 395                 400

Leu Asp Asp Glu Thr Leu Ala Lys Leu Ile Ala Lys Ile Pro Thr Ile
                405                 410                 415

Thr Ala Val Cys Asn Leu His Gly Glu Lys Leu Gln Val Phe Lys Gln
                420                 425                 430

Ser His Pro Glu Ile Val Asn Thr Leu Phe Pro Pro Leu Tyr Lys Glu
            435                 440                 445

Leu Phe Asn Pro Asp Cys Ala Thr Gly Cys Lys
        450                 455
```